US006500844B1

(12) United States Patent
Finke et al.

(10) Patent No.: US 6,500,844 B1
(45) Date of Patent: Dec. 31, 2002

(54) CYCLOPENTYL MODULATORS OF CHEMOKINE RECEPTOR ACTIVITY

(75) Inventors: Paul E. Finke, Milltown; Kevin T. Chapman, Scotch Plains; Malcolm Maccoss, Freehold; Sander G. Mills, Scotch Plains, all of NJ (US); Bryan Oates, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/590,487

(22) Filed: Jun. 8, 2000

Related U.S. Application Data
(60) Provisional application No. 60/139,067, filed on Jun. 11, 1999.

(51) Int. Cl.$^7$ .................... A61K 31/445; C07D 401/00; C07D 409/00; C07D 211/56
(52) U.S. Cl. ........................ 514/317; 514/323; 546/208; 546/212; 546/224
(58) Field of Search ................................. 546/224, 210, 546/209, 208, 212; 514/317, 323, 321, 324

(56) References Cited

U.S. PATENT DOCUMENTS

| | | | |
|---|---|---|---|
| 424,271 A | * | 1/1890 | Cousse et al. |
| 3,647,804 A | * | 3/1972 | Rynbrandt et al. |
| 4,105,666 A | | 8/1978 | Ward |
| 4,281,132 A | | 7/1981 | Ward |
| 5,169,844 A | | 12/1992 | Commons et al. |
| 5,424,319 A | | 6/1995 | Hanson et al. |
| 5,712,279 A | | 1/1998 | Biller et al. |
| 5,750,549 A | | 5/1998 | Caldwell et al. |
| 5,935,974 A | | 8/1999 | Rae et al. |
| 6,054,468 A | | 4/2000 | Geerts et al. |

FOREIGN PATENT DOCUMENTS

| | | |
|---|---|---|
| WO | WO 98/25617 | 6/1998 |
| WO | WO 98/31364 | 7/1998 |
| WO | WO 99/04794 | 2/1999 |
| WO | WO 99/09984 | 3/1999 |

OTHER PUBLICATIONS

J. J. Gomez–Reino et al., "Association of Rheumatoid Arthritis with a Functional Chemokine Receptor, CCR5", Arthritis & Rheumatism, vol. 42, No. 5, May 1999, pp. 989–992.
T. J. Schall, "Biology of the Rantes/sis Cytokine Family", Cytokine, vol. 3, No. 3, May 1991, pp. 165–183.
P. M. Murphy, "The Molecular Biology of Leukocyte Chenoattractant Receptors", Annual Review of Immunology, vol. 12, 1994, pp. 593–633.
H. Deng et al., "Identification of a major co–receptor for primary isolates HIV–1", Nature, vol. 381, Jun. 1996, pp. 661–666.
R. Horuk, "Molecular properties of the chemokine receptor family", Trends Pharm. Science, vol. 15, 1994, pp. 159–165.
A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.
K. Neote et al., "Molecular Cloning, Functional Expression, and Signaling Characteristics of C–C Chemokine Receptor", Cell, vol. 72, Feb. 1993, pp. 415–425.
C. Combadiere et al., "Cloning and Functional Expression of a Human Eosinophil CC Chemokine Receptor", J. Biol. Chem., vol. 270, No. 27, Jul. 1995, pp. 16491–16494.
C. A. Power et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.
M. Samson et al., "Molecular Cloning and Functional Expression of a New Human CC–Chemokine Receptor Gene", Biochemistry, vol. 35, 1996, pp. 3362–3367.
A. Chaudhuri et al., "Expression of the Duffy Antigen in K562 Cells,", J. Biol. Chem., vol. 269, No. 11, Mar. 1994, pp. 7835–7838.
H. Kita et al., "Chemokines Active on Eosinophils: Potential Roles in Allergic Inflammation", J. Exp. Med., vol. 183, Jun. 1996, pp. 2421–2426.
D. Smith et al., "Blocking of HIV–1 Infectivity by a Soluble, Secreted Form of the CD4 Antigen", Science, vol. 238, 1987, pp. 1704–1707.
J. A. Levy, "Infection by Human Immunodeficiency Virus—CD4 is not Enough", N. Eng. J. Med., vol. 335, No. 20, Nov. 1996, pp. 1528–1530.
T. Dragic et al., "HIV–1 entry into CD4+ cells is mediated by the chemokine receptor CC–CKR5", Nature, vol. 381, Jun 1996, pp. 667–673.

(List continued on next page.)

Primary Examiner—Alan L. Rothman
Assistant Examiner—Binta Robinson
(74) Attorney, Agent, or Firm—Kenneth R. Walton; Melvin Winokur; J. Eric Thies

(57) ABSTRACT

The present invention is directed to compounds of the formula I:

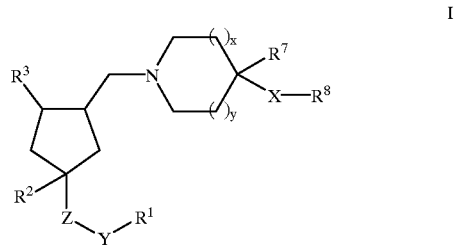

(wherein $R^1$, $R^2$, $R^3$, $R^7$, $R^8$, X, Y, Z, x and y are defined herein) which are useful as modulators of chemokine receptor activity. In particular, these compounds are useful as modulators of the chemokine receptors CCR-5 and/or CCR-3.

20 Claims, No Drawings

OTHER PUBLICATIONS

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistence to HIV–1 infection in caucasian individuals bearing mutant alleles of the CCR–5 cehmokine receptor gene", Nature, vol. 382, Aug. 1996, pp. 722–725.

C. M. Hill et al., "Natural resistence to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

Chemical Abstracts, 54:4542h, "Syntheses of analgesics—(XXIII) aminocyclopentane derivs.", Yakugaku Zasshi, 79—, 1087–91 (1959), Takahashi et al., vol. 54, 1960.*

Ko et al., "Preparation of N–ureidoalkyl–piperidines as modulators or chemokine receptor activiity", Chemical Abstracts No. 133:43441, Abstract of WO 00/35449.

* cited by examiner

CYCLOPENTYL MODULATORS OF CHEMOKINE RECEPTOR ACTIVITY

This application claims the benefit of U.S. Provisional Application No. 60/139,067, filed Jun. 11, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.* 12, 593–633 (1994)). There are two classes of chemokines, C—X—C (α) and C—C (β), depending on whether the first two cysteines are separated by a single amino acid (C—X—C) or are adjacent (C—C). The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/ "CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1α, RANTES, MCP-1] (Power, et al., *J. Biol. Chem.*, 270, 19495–19500 (1995)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the β-chemokines RANTES, MIP-1α and MIP-1β (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that β-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1α and MIP-1β (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

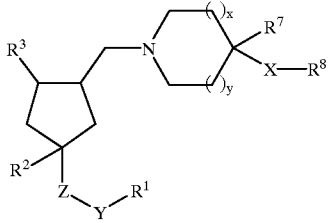

I wherein:
X is selected from:
—(CO)NR$^9$—, —NR$^9$(CO)—, —O(CO)NR$^9$—, —NR$^9$(CO)O—, and —NR$^9$(CO)NR$^{10}$—,
where R$^9$ is independently selected from: hydrogen, C$_{1-10}$ alkyl, C$_{3-8}$ cycloalkyl, C$_{1-6}$ alkyl-C$_{3-6}$ cycloalkyl, C$_{2-10}$ alkenyl, C$_{2-10}$ alkynyl, benzyl, phenyl, or naphthyl, which is unsubstituted or substituted with 1–3 substituents where the substituents are independently selected from: halo, hydroxy, C$_{1-6}$ alkyl, C$_{1-3}$ alkoxy, phenyl and trifluoromethyl,
and where R$^{10}$ is independently selected from: hydrogen, C$_{1-6}$ alkyl, benzyl, or phenyl, which is unsubstituted or substituted with 1–3 substituents where the substituents are independently selected from: halo, C$_{1-3}$ alkyl, C$_{1-3}$ alkoxy and trifluoromethyl,
or where R$^9$ and R$^{10}$ may be joined together to form a 5–8 membered ring which may be unsubstituted or substituted with halo, C$_{1-3}$ alkyl, and C$_{1-3}$ alkoxy;

Y is selected from:
a single bond, —(CO)—, —(CO)O—, —SO$_2$—, —SO$_2$NR$^9$—, —C$_{1-10}$ alkyl-, —(CO)NR$^9$—, and —(CS)NR$^9$—;

Z is selected from:
a single bond, —NR$^9$—, —O—, and —C$_{1-10}$ alkyl-;

R$^1$ is selected from:
phenyl, naphthyl, heterocycle other than tetrazolyl, C$_{1-10}$ alkyl, C$_{3-6}$ cycloalkyl, C$_{1-6}$ alkyl-C$_{3-6}$ cycloalkyl, C$_{2-10}$ alkenyl, C$_{2-10}$ alkynyl, C$_{1-4}$ alkyl-phenyl or C$_{1-4}$ alkyl-heterocycle, which is unsubstituted or substituted with 1–3 substituents where the substituents are independently selected from: halo, C$_{1-3}$ alkyl, C$_{1-3}$ alkoxy, trifluoromethoxy and trifluoromethyl,
or when Z is —NR$^9$—, then R$^9$ and R$^1$ may be joined together to form a 5–8 membered alkyl or heterocycle ring which may be unsubstituted or substituted with halo, C$_{1-3}$ alkyl, and C$_{1-3}$ alkoxy;

R$^2$ is selected from:
(1) hydrogen, and
(2) hydroxy, or R$^2$ and Z may be joined together to form a double bond;

R$^3$ is selected from the group consisting of:
phenyl and heterocycle, which is unsubstituted or substituted with 1–7 substituents where the substituents are independently selected from:
(a) halo,
(b) trifluoromethyl,
(c) hydroxy,
(d) C$_{1-3}$ alkyl,
(e) —O—C$_{1-3}$ alkyl,
(f) —CO$_2$R$^9$,
(g) —NR$^9$R$^{10}$, and
(h) —CONR$^9$R$^{10}$;

R$^7$ is selected from:
(1) hydrogen,
(2) C$_{1-6}$ alkyl, which is unsubstituted or substituted with 1–4 substituents where the substituents are independently selected from: hydroxy, cyano, and halo,
(3) hydroxy, and
(4) halo;

R$^8$ is selected from:
C$_{1-10}$ alkyl, C$_{3-6}$ cycloalkyl, C$_{2-10}$ alkenyl, C$_{2-10}$ alkynyl, phenyl, C$_{1-6}$ alkyl-phenyl, C$_{1-6}$ alkyl-C$_{3-6}$ cycloalkyl,
C$_{1-4}$ alkyl-O—C$_{0-4}$ alkyl-phenyl, naphthyl, biphenyl, and heterocycle, which is unsubstituted or substituted with 1–7 of R$^{12}$ where
R$^{12}$ is independently selected from:
(a) halo,
(b) cyano,
(c) hydroxy,
(d) C$_{1-6}$ alkyl, which is unsubstituted or substituted with 1–5 of R$^{13}$ where R$^{13}$ is independently selected from: halo, cyano, hydroxy, C$_{1-6}$ alkoxy, —CO$_2$H, —CO$_2$(C$_{1-6}$ alkyl), phenyl, trifluoromethyl, and —NR$^9$R$^{10}$, (e) —O—$C_{1-6}$alkyl, which is unsubstituted or substituted with 1–5 of $R^{13}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$,
(v) —$NR^9S(O)_2$—$NR^9R^{10}$,
(w) 1-naphthyl, and
(x) 2-naphthyl;

x is an integer selected from 0, 1 and 2, and y is an integer selected from 0, 1 and 2, with the proviso that the sum of x and y is 2;
and pharmaceutically acceptable salts thereof and individual diastereomers thereof.

One embodiment of the present invention is a compound of formula I,
wherein
X is selected from:

—(CO)$NR^9$—, —$NR^9$(CO)—, —O(CO)$NR^9$—, —$NR^9$(CO)O—, and —$NR^9$(CO)$NR^{10}$—,
where $R^9$ is independently selected from: hydrogen, $C_{1-10}$ alkyl, $C_{3-8}$ cycloalkyl, $C_{1-6}$ alkyl-$C_{3-6}$ cycloalkyl, $C_{2-10}$ alkenyl, C2-10 alkynyl, benzyl or phenyl, which is unsubstituted or substituted with 1–3 substituents where the substituents are independently selected from: halo, $C_{1-6}$ alkyl, $C_{1-3}$ alkoxy, phenyl and trifluoromethyl,
and where $R^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl,
or where $R^9$ and $R^{10}$ may be joined together to form a 5–8 membered ring which may be unsubstituted or substituted with halo, $C_{1-3}$ alkyl, and $C_{1-3}$ alkoxy;

Y is selected from:
a single bond, —(CO)—, —(CO)O—, —$SO_2$—, —$C_{1-10}$ alkyl-, —(CO)$NR^9$—, and —(CS)$NR^9$—;
Z is selected from:
a single bond, —$NR^9$—, —O—, and —$C_{1-10}$ alkyl-;
$R^1$ is selected from:
phenyl, heterocycle other than tetrazolyl, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, $C_{1-4}$ alkyl-phenyl or $C_{1-4}$ alkyl-heterocycle, which is unsubstituted or substituted with 1–3 substituents where the substituents are independently selected from: halo, $C_{1-3}$ alkyl, $C_{1-3}$ alkoxy, trifluoromethoxy and trifluoromethyl,
or when Z is —$NR^9$—, then $R^9$ and $R^1$ may be joined together to form a 5–8 membered alkyl or heterocycle ring which may be unsubstituted or substituted with halo, $C_{1-3}$ alkyl, and $C_{1-3}$ alkoxy;

and all other variables are as previously defined;
and pharmaceutically acceptable salts thereof and individual diastereomers thereof.

Another embodiment of the present invention is a compound of formula I, wherein Y is selected from a single bond, —(CO)—, —(CS)$NR^9$—, —(CO)O—, —$SO_2$—, and —(CO)$NR^9$—;
$R^9$ is independently selected from hydrogen and $C_{1-6}$ alkyl;
Z is selected from a single bond, —O—, and —$NR^9$—;
and all other variables are as defined in the preceding embodiment;
and pharmaceutically acceptable salts thereof and individual diastereomers thereof.

Preferred compounds of the present invention include those of formula Ia:

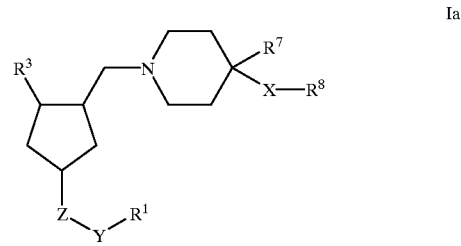

Ia wherein $R^1$, $R^3$, $R^7$, $R^8$, X, Y and Z are defined herein;
and pharmaceutically acceptable salts and individual diastereomers thereof.

More preferred compounds of the present invention include those of formula Ic:

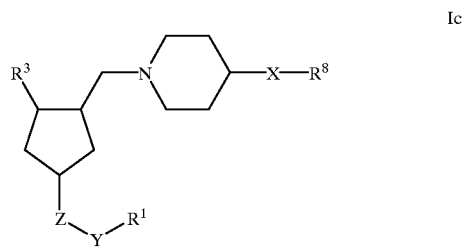

Ic wherein $R^1$, $R^3$, $R^8$, X, Y and Z are defined herein;
and pharmaceutically acceptable salts and individual diastereomers thereof.

Highly preferred compounds of the present invention include those of formula Id:

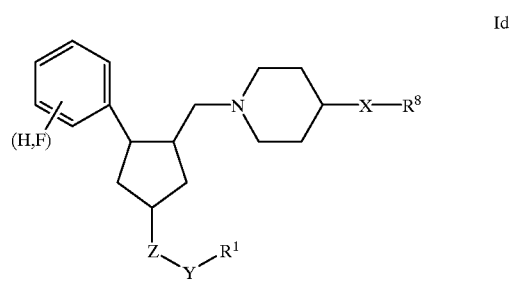

Id wherein $R^1$, $R^8$, X, Y and Z are defined herein;
and pharmaceutically acceptable salts and individual diastereomers thereof.

In the present invention it is preferred that X is selected from:

—(CO)NR$^9$—, —NR$^9$(CO)—, —NR$^9$(CO)O—, and —NR$^9$(CO)NR$^{10}$—,
- where R$^9$ is independently selected from: hydrogen, C$_{1-10}$ alkyl, C$_{3-6}$ cycloalkyl, C$_{1-6}$ alkyl-C$_{3-6}$ cycloalkyl, C$_{2-10}$ alkenyl, C$_{2-10}$ alkynyl, benzyl or phenyl, which is unsubstituted or substituted with 1–3 substituents where the substituents are independently selected from: halo, C$_{1-3}$ alkyl, C$_{1-3}$ alkoxy and trifluoromethyl,
- and where R$^{10}$ is independently selected from: hydrogen, C$_{1-6}$ alkyl, benzyl, or phenyl, which is unsubstituted or substituted with 1–3 substituents where the substituents are independently selected from: halo, C$_{1-3}$ alkyl, C$_{1-3}$ alkoxy and trifluoromethyl,
- or where R$^9$ and R$^{10}$ may be joined together to form a 5–8 membered ring which may be unsubstituted or substituted with halo, C$_{1-3}$ alkyl, and C$_{1-3}$ alkoxy;

In the present invention it is more preferred that X is selected from:
—NR$^9$(CO)O— and —NR$^9$(CO)NR$^{10}$—,
- where R$^9$ is independently selected from: hydrogen, C$_{1-10}$ alkyl, C$_{2-10}$ alkenyl, and C$_{1-6}$ alkyl-C$_{3-6}$ cycloalkyl,
- where R$^{10}$ is independently selected from: hydrogen and C$_{1-6}$ alkyl,
- or where R$^9$ and R$^{10}$ may be joined together to form a 5–8 membered ring which is unsubstituted.

In the present invention it is even more preferred that X is selected from:
—NR$^9$(CO)O— and —NR$^9$(CO)NR$^{10}$—,
- where R$^9$ is independently selected from: hydrogen, C$_{1-10}$ alkyl, C$_{2-10}$ alkenyl, and C$_{1-6}$ alkyl-C$_{3-6}$ cycloalkyl,
- where R$^{10}$ is independently selected from: hydrogen and C$_{1-6}$ alkyl,
- or where R$^9$ and R$^{10}$ may be joined together to form a 5–8 membered ring which is unsubstituted.

In the present invention it is still more preferred that X is selected from:
—NR$^9$(CO)O—, and —NR$^9$(CO)NH—,
where R$^9$ is independently selected from: methyl, ethyl, n-propyl, allyl, and —CH$_2$-cyclopropyl.

In the present invention it is preferred that Y is selected from:
a single bond, —(CO)—, —(CS)NR$^9$—, —(CO)O—, —SO$_2$—, and —(CO)NR$^9$—,
where R$^9$ is independently selected from hydrogen and C$_{1-6}$ alkyl.

In the present invention it is more preferred that Y is selected from:
a single bond, —(CO)—, —(CS)NR$^9$—, —(CO)O—, —SO$_2$—, and —(CO)NR$^9$—,
where R$^9$ is independently selected from hydrogen and methyl.

In the present invention it is preferred that Z is selected from:
a single bond, —O—, and —NR$^9$—,
- where R$^9$ is independently selected from hydrogen, C$_{1-6}$ alkyl, C$_{3-8}$ cycloalkyl, phenyl, and C$_{1-6}$ alkyl-phenyl, which is unsubstituted or substituted with 1–3 substituents where the substituents are independently selected from: halo, C$_{1-3}$ alkyl, C$_{1-3}$ alkoxy, phenyl and trifluoromethyl;

In the present invention it is more preferred that Z is selected from:
a single bond, —O—, and —NR$^9$—,
- where R$^9$ is independently selected from hydrogen, C$_{1-6}$ alkyl, C$_{3-8}$ cycloalkyl, phenyl, and C$_{1-6}$ alkyl-phenyl, which is unsubstituted or substituted with 1–3 substituents where the substituents are independently selected from: C$_{1-3}$ alkyl, phenyl and C$_{1-3}$ alkoxy;

In the present invention it is preferred that R$^1$ is selected from:
C$_{1-10}$ alkyl, cyclohexyl, C$_{0-2}$ alkyl-phenyl and CH$_2$-cyclohexyl,
which is unsubstituted or substituted with 1–3 substituents where the substituents are independently selected from: halo, C$_{1-3}$ alkyl, C$_{1-3}$ alkoxy, trifluoromethoxy and trifluoromethyl.

In the present invention it is more preferred that R$^1$ is selected from:
methyl, iso-butyl, tert-butyl, hexyl, cyclohexyl, CH$_2$-cyclohexyl, and
C$_{0-2}$ alkyl-phenyl wherein the phenyl is unsubstituted or substituted with 1–3 substituents where the substituents are independently selected from: chloro, fluoro, methyl, tert-butyl, trifluoromethoxy and trifluoromethyl.

In the present invention it is preferred that R$^2$ is hydrogen.

In the present invention it is preferred that R$^3$ is selected from the group consisting of:
phenyl and thienyl,
which may be unsubstituted or substituted with 1–5 substituents where the substituents are independently selected from:
(a) halo,
(b) trifluoromethyl,
(c) hydroxy,
(d) C$_{1-3}$ alkyl, and
(e) —O—C$_{1-3}$ alkyl.

In the present invention it is more preferred that R$^3$ is selected from the group consisting of:
phenyl and thienyl,
which may be unsubstituted or substituted with 1–5 substituents where the substituents are independently selected from:
(a) fluoro,
(b) chloro,
(c) trifluoromethyl,
(d) hydroxy, and
(e) C$_{1-3}$ alkyl.

In the present invention it is even more preferred that R$^3$ is selected from the group consisting of:
phenyl, which may be unsubstituted or substituted with 1–5 substituents where the substituents are independently selected from:
(a) fluoro, and
(b) chloro; and
unsubstituted thienyl.

In the present invention it is still more preferred that R$^3$ is unsubstituted phenyl, (3-fluoro)phenyl or 3-thienyl.

In the present invention it is preferred that R$^7$ is hydrogen, fluoro, hydroxy or C$_{1-6}$ alkyl.

In the present invention it is more preferred that R$^7$ is hydrogen or fluoro.

In the present invention it is even more preferred that R$^7$ is hydrogen.

In the present invention it is preferred that R$^8$ is selected from:
C$_{1-6}$ alkyl, C$_{3-6}$ cycloalkyl, phenyl, 1-naphthyl, 2-naphthyl, C$_{1-6}$ alkyl-phenyl, and C$_{1-6}$ alkyl-C$_{3-6}$ cycloalkyl, which is unsubstituted or substituted with 1–7 substituents where the substituents are independently selected from:
(a) halo,
(b) cyano,
(c) hydroxy,
(d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, phenyl, —$CO_2(C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;
(e) —O—$C_{1-6}$ alkyl, which is unsubstituted or substituted with 1–5 of $R^{13}$,
(f) —$CF_3$,
(g) —$CHF_2$,
(h) —$CH_2F$,
(i) —$NO_2$,
(j) phenyl, and
(k) —$CO_2R^9$.

In the present invention it is more preferred that $R^8$ is selected from:
$C_{1-6}$ alkyl, $C_{3-6}$ cycloalkyl, —$CH_2$-cyclohexyl, phenyl, and —$CH_2$-phenyl, wherein the phenyl is unsubstituted or substituted with 1–5 substituents where the substituents are independently selected from:
(a) halo,
(b) —$NO_2$,
(c) —$CF_3$,
(d) —$C_{1-6}$ alkyl, and
(e) phenyl.

In the present invention it is even more preferred that $R^8$ is selected from:
methyl, ethyl, n-butyl, tert-butyl, $CH_2$-cyclohexyl, phenyl and $CH_2$ phenyl, wherein the phenyl is unsubstituted or substituted with a substituent selected from:
(a) fluoro,
(b) chloro
(c) —$NO_2$,
(d) —$CF_3$,
(e) methyl,
(f) phenyl,
(g) 1-naphthyl, and
(n) 2-naphthyl.

In the present invention it is preferred that x is an integer which is 1 and y is an integer which is 1.

It is to be understood that embodiments of the present invention include, but are not limited to, compounds of formula I wherein $R^1$, $R^2$, $R^3$, $R^7$, $R^8$, X, Y, Z, x, and y are defined in accordance with one of the embodiments or aspects thereof as set forth above. Any and all possible combinations of preferred, more preferred, even more preferred, highly preferred, more highly preferred, and most preferred definitions of these variables in formulas I are within the scope of the present invention.

The compounds of the instant invention have at least two asymmetric centers at the ring junction of the substitutents bearing the piperidine and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

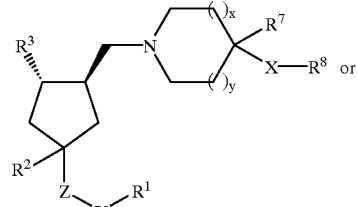

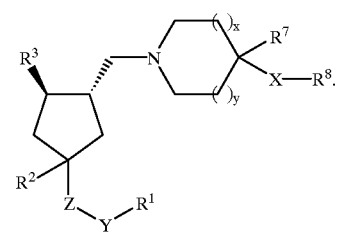

The relative configurations of the even more preferred compounds of this invention with respect to the configuration at the 1-position of the cyclopentane ring is 1,3-trans of the orientation as depicted:

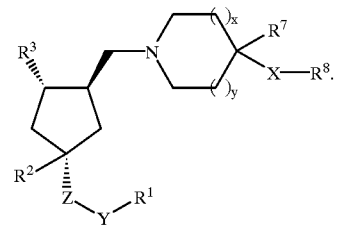

The independent syntheses of these diastereomer their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothipheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression " . . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1–3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri-substituted phenyl.

Exemplifying the invention is the use of the compounds disclosed in the Examples and herein.

Specific compounds within the present invention include a compound which is selected from the group consisting of:

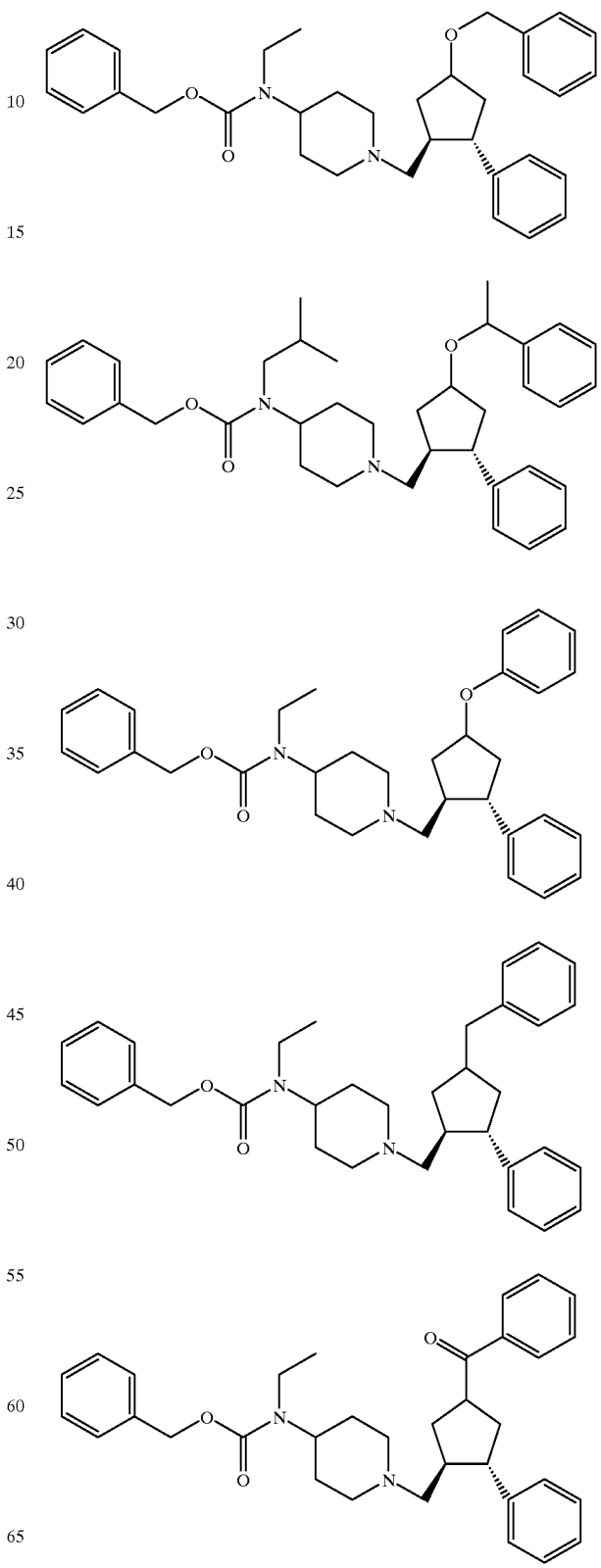

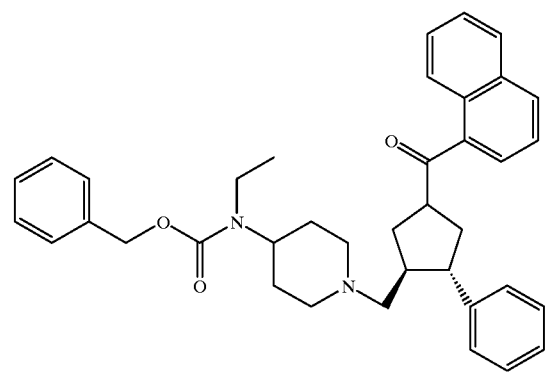
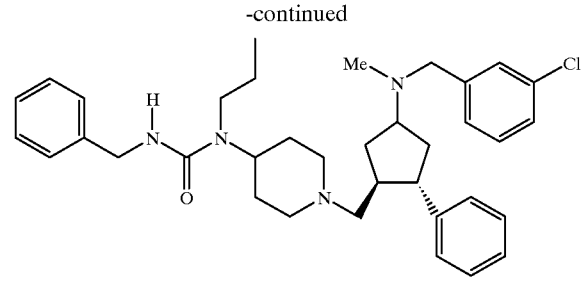
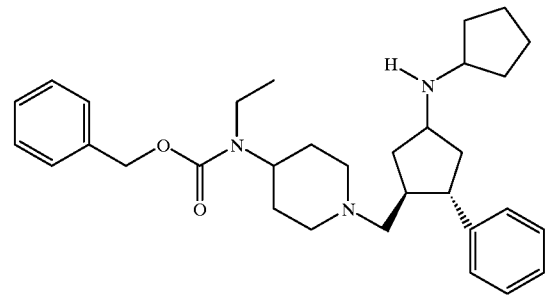
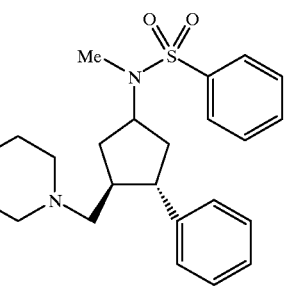
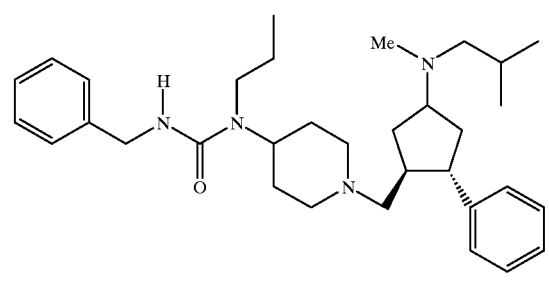
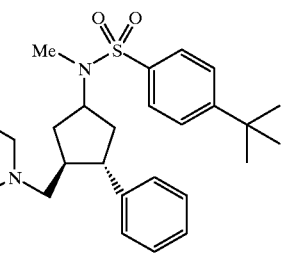
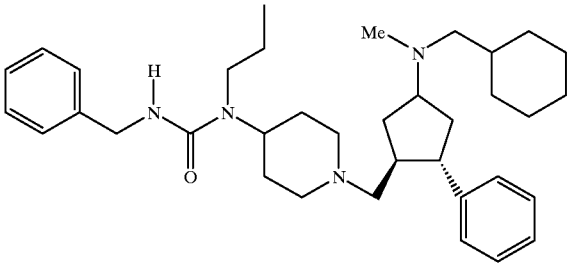
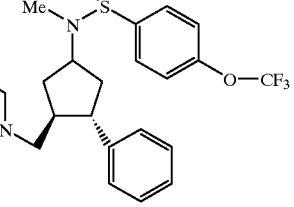
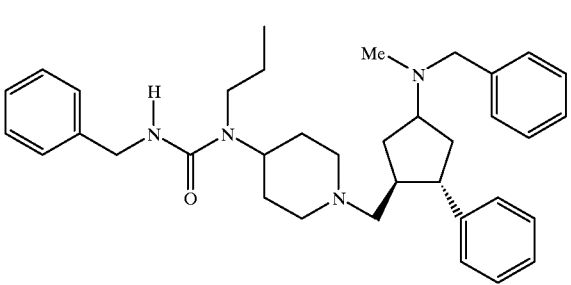
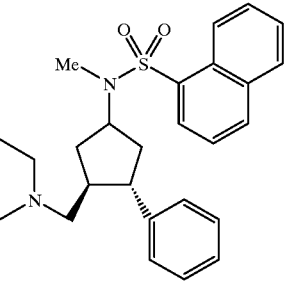
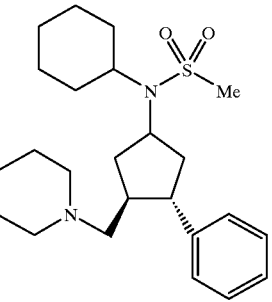

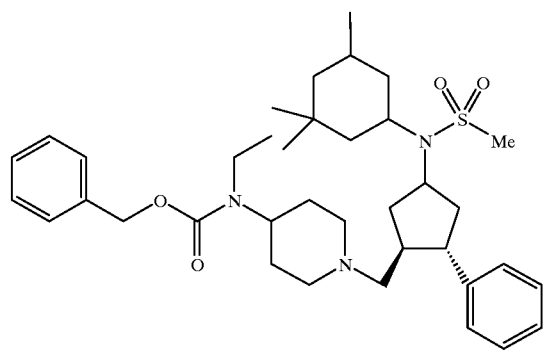
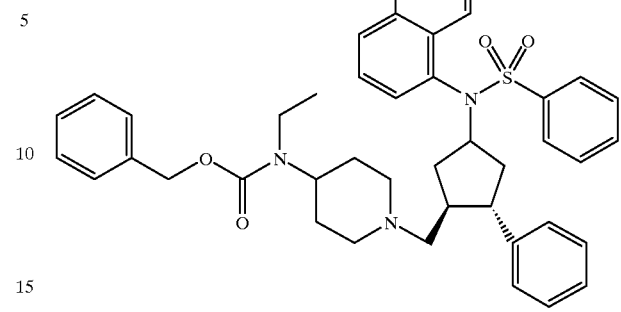
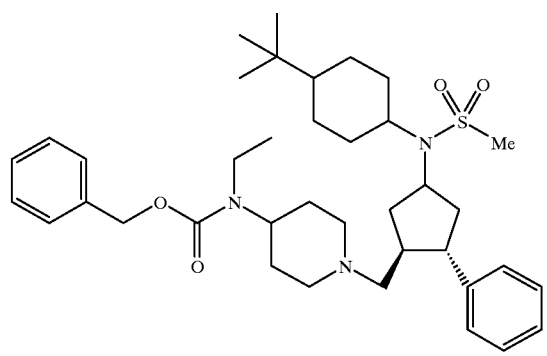
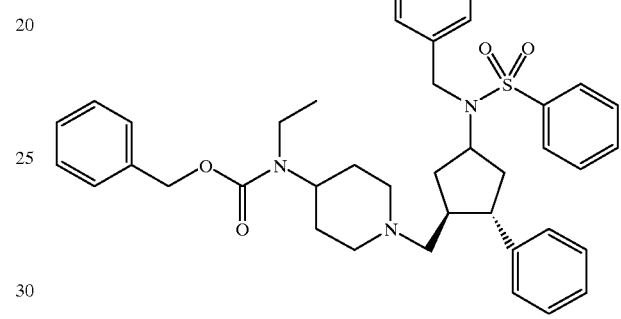
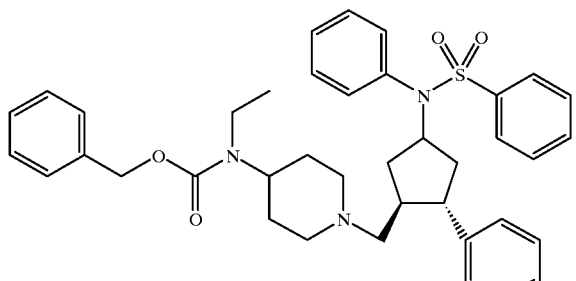
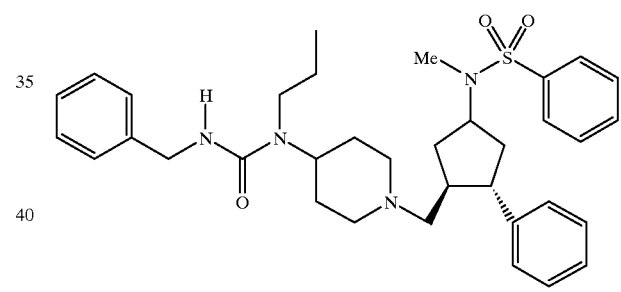
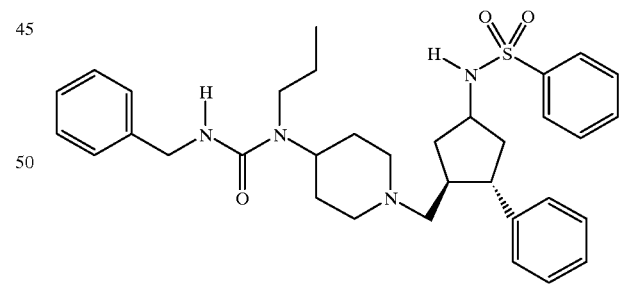
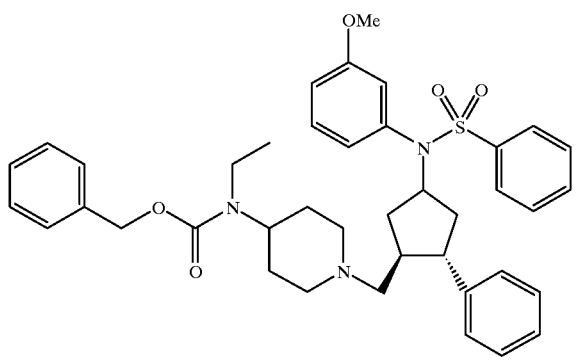
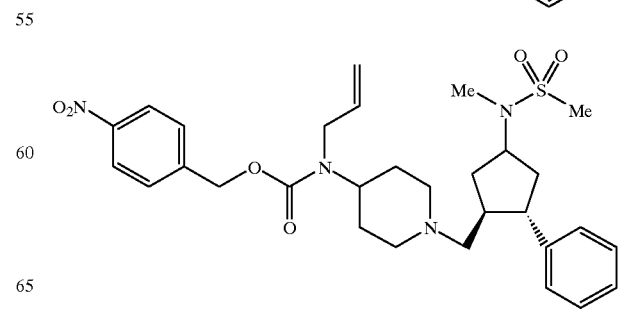

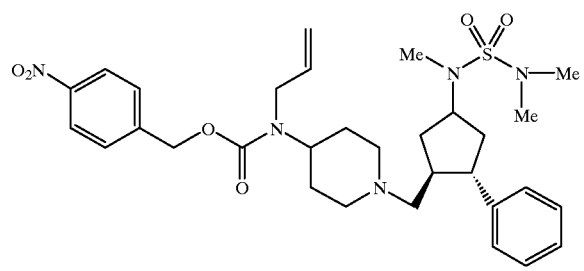
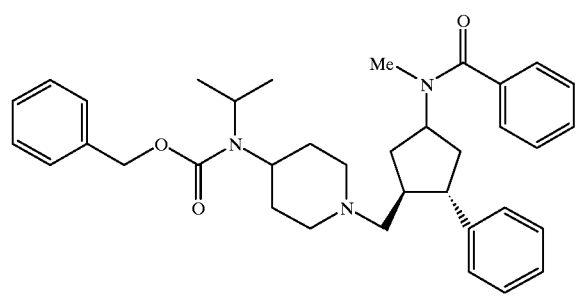
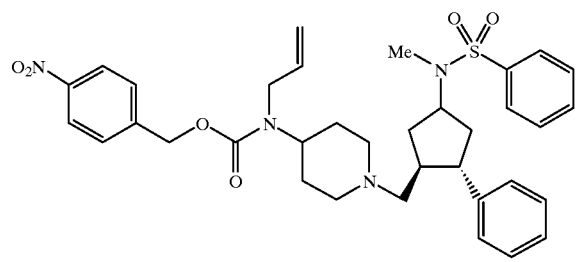
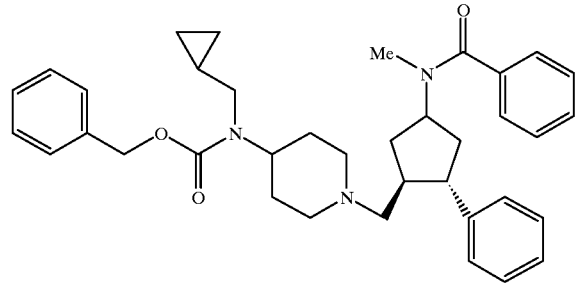
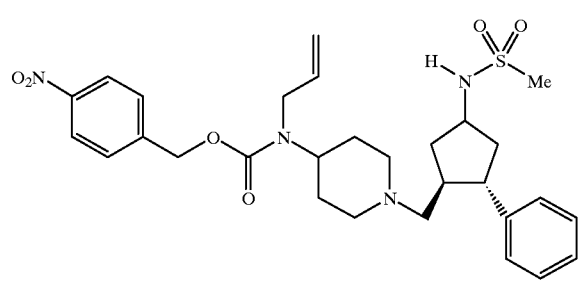
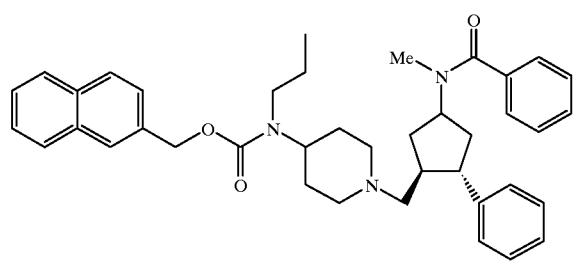
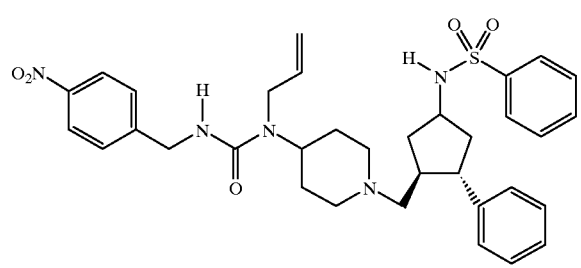
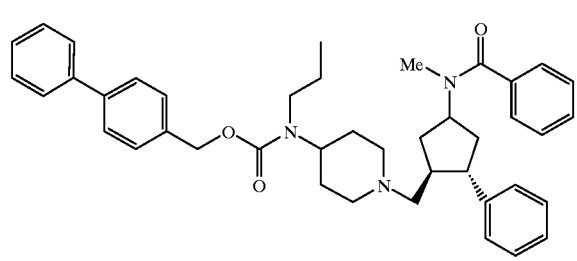
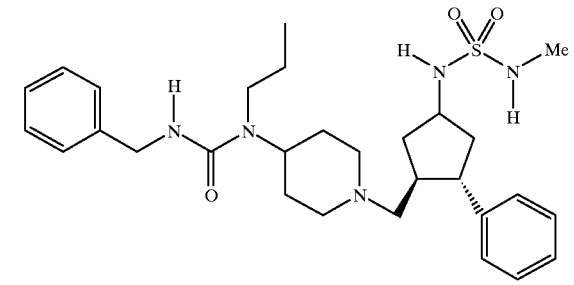
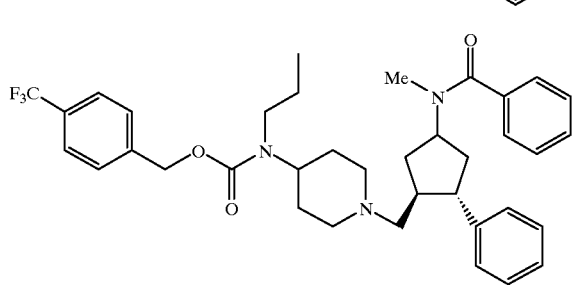
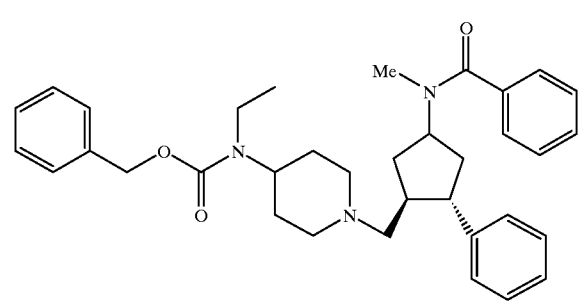
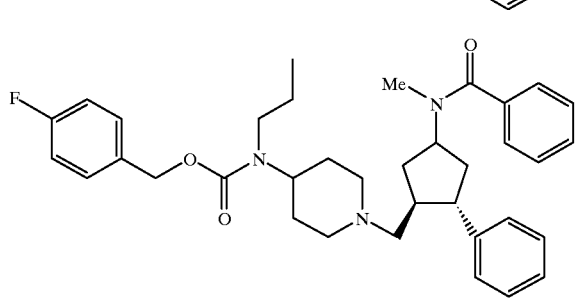

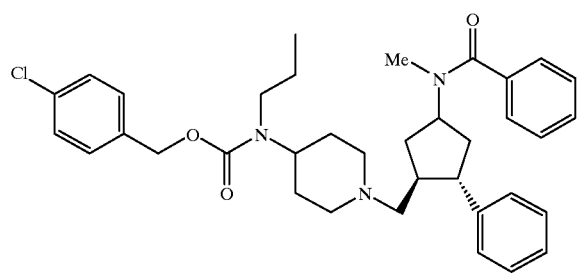
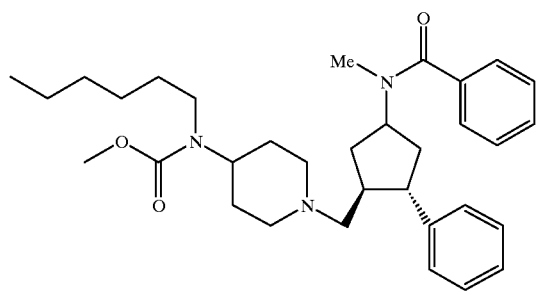
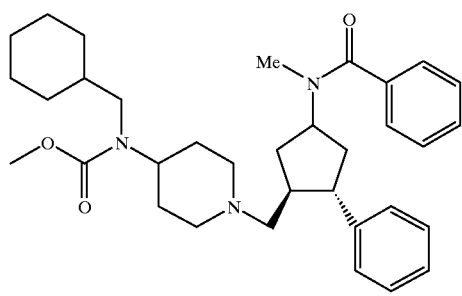
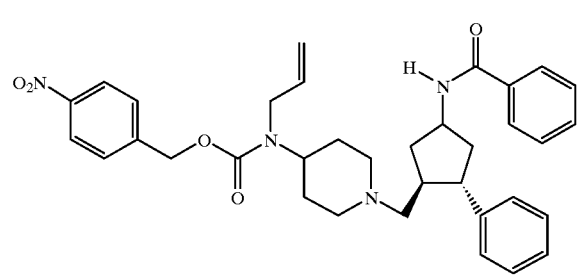
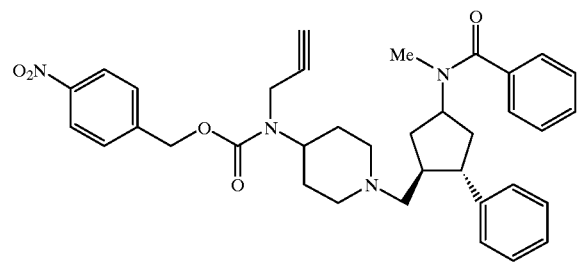
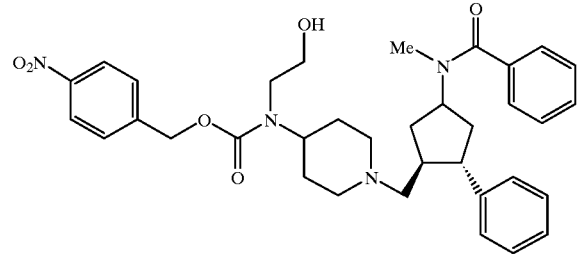
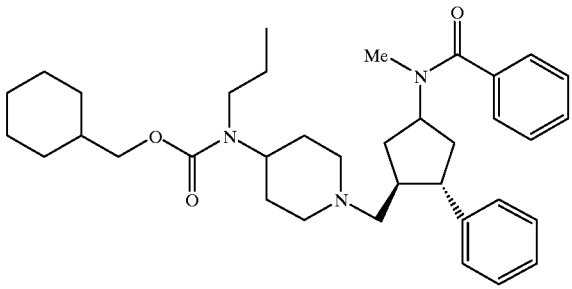
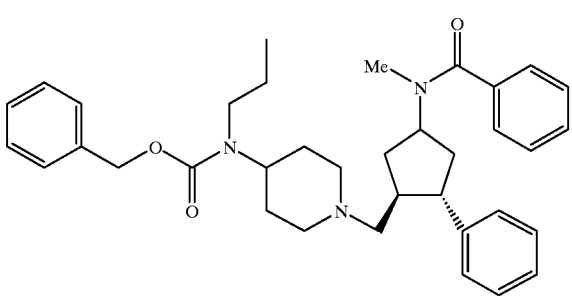
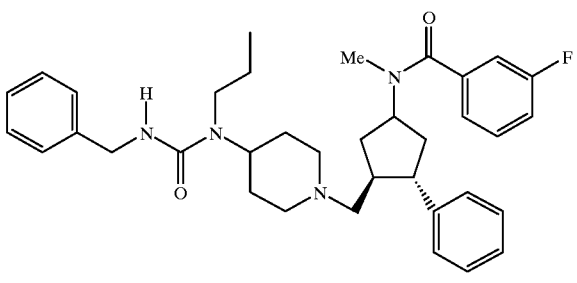
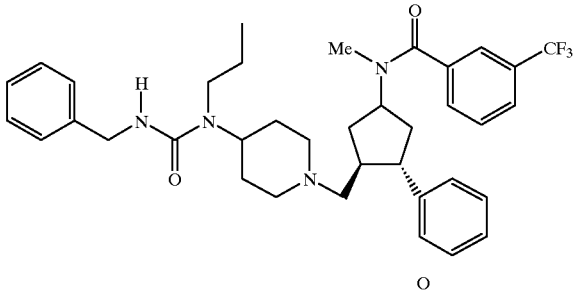
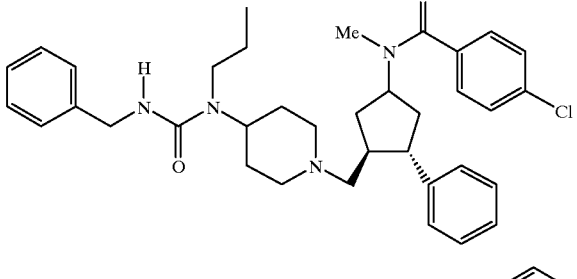
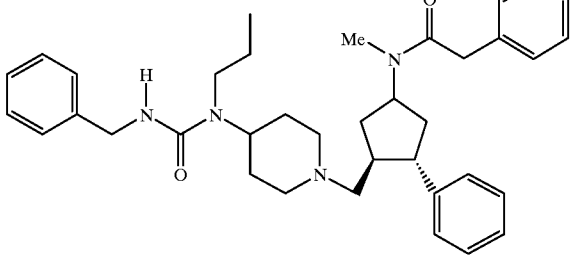

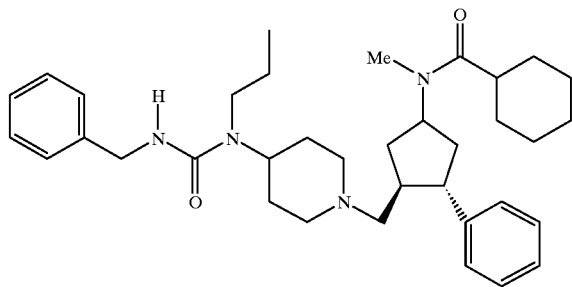
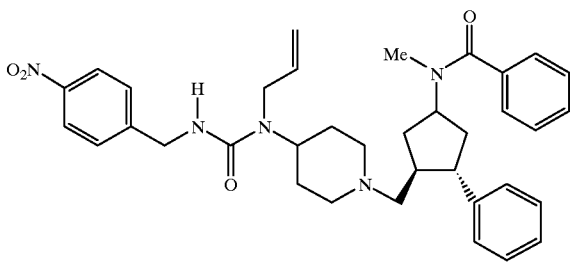
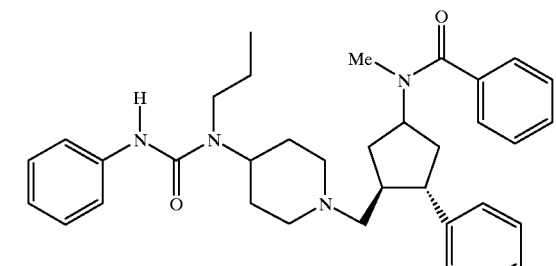
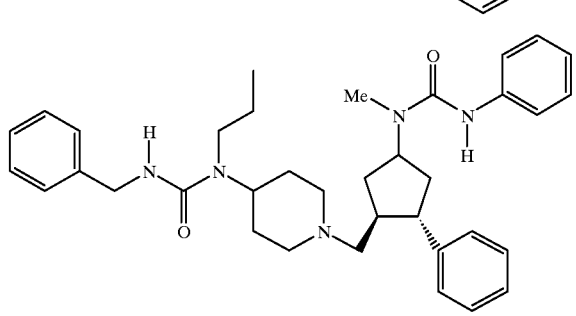
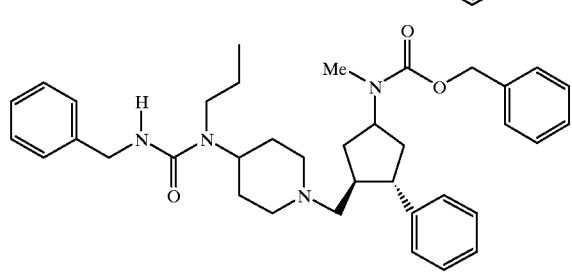
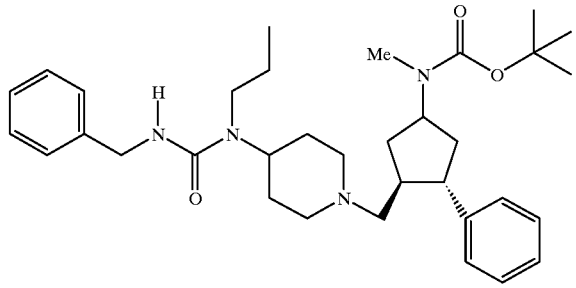
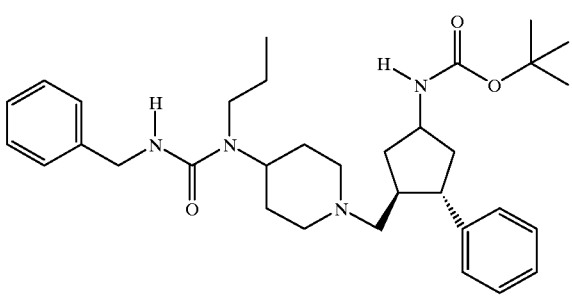
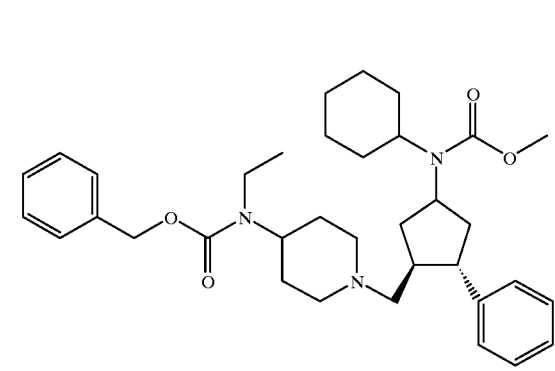
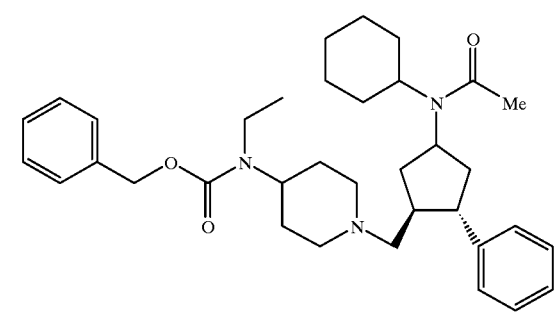
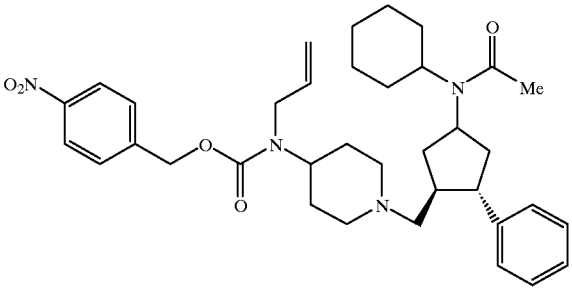
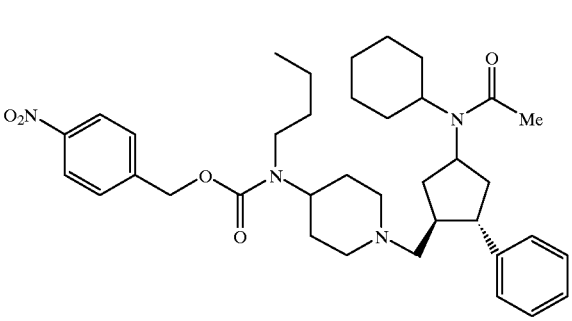

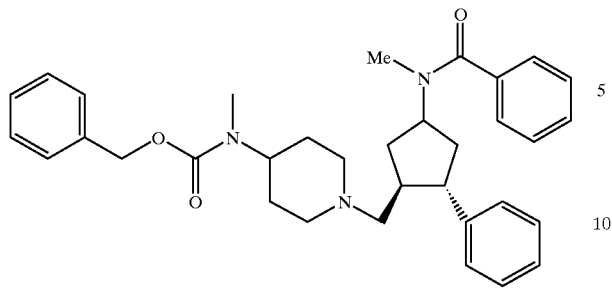
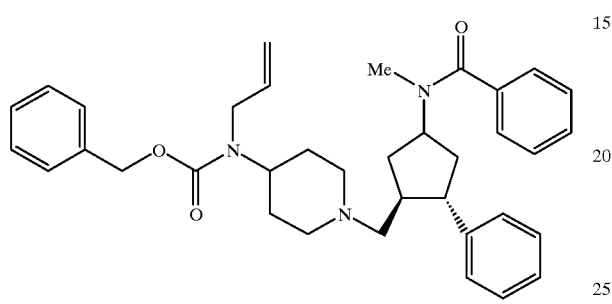
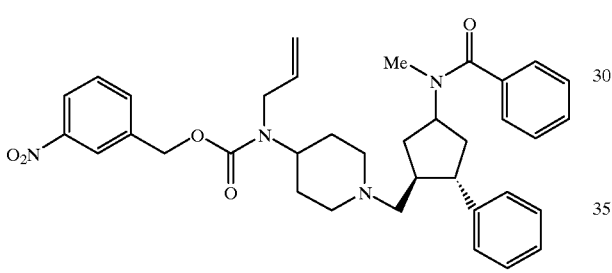
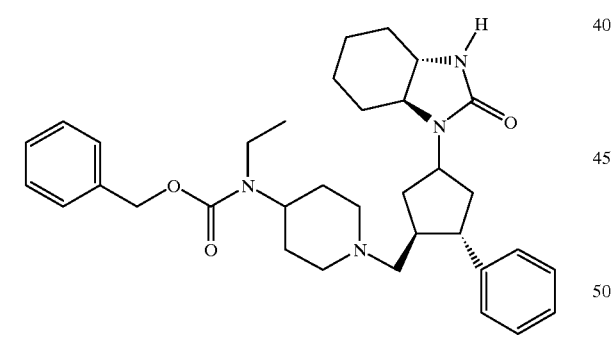
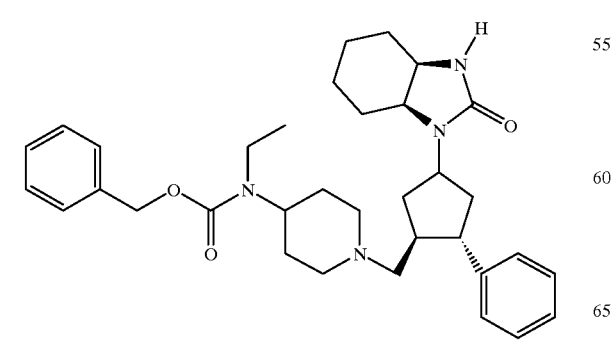
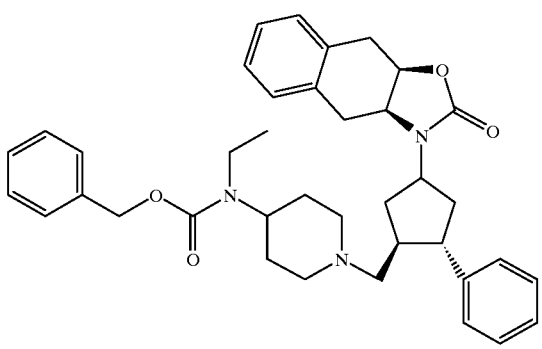
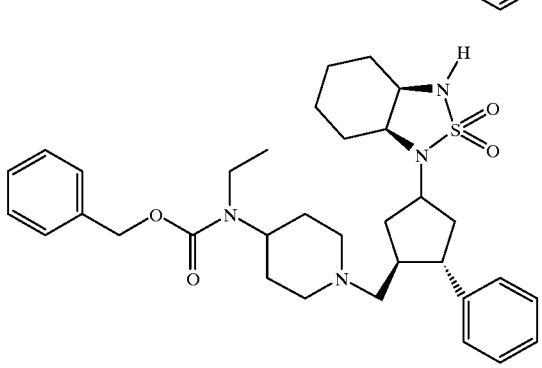
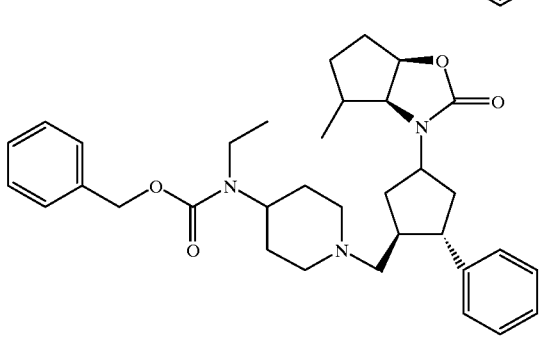
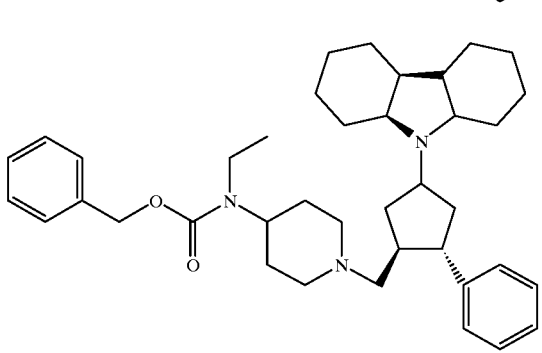
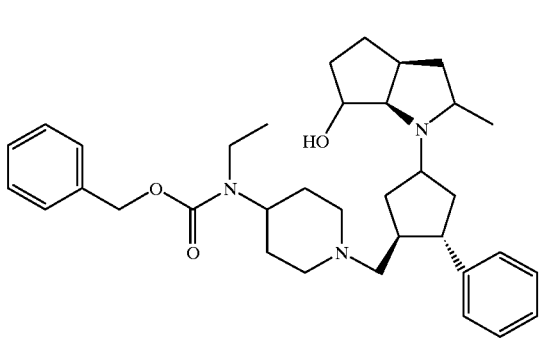

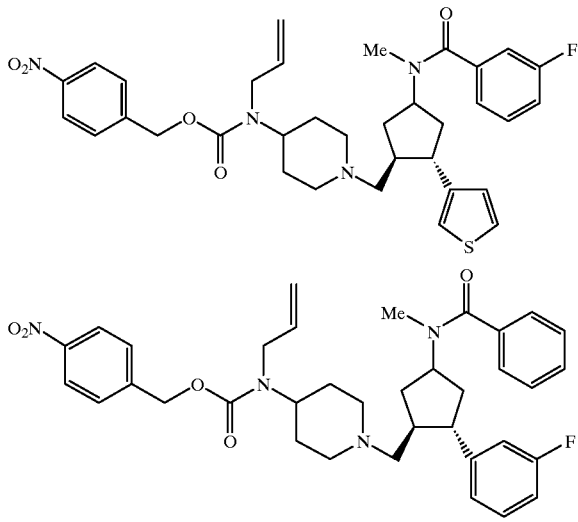

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciutis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, *Taeniasis saginata,* Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxyephedrine; an antuitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/4078 1, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

| Drug Name | Manufacturer | Indication |
|---|---|---|
| ANTIVIRALS | | |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fludro-ddA | Nat'l Cancer Institute | AIDS-associated diseases |
| (-) 6-Chloro-4(S)-cyclopropyl-ethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |

-continued

| Drug Name | Manufacturer | Indication |
|---|---|---|
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| EL10 | Elan Corp, PLC (Gainesville, GA) | HIV infection |
| Efavirenz (DMP 266) (-) 6-Chloro-4(S)-cyclopropyl-ethynyl-4(S)-trifluoromethyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX478 | Vertex | HIV infection, AIDS, ARC |
| Zalcitabine | Hoffmann-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/ AG1776 | Agouron | HIV infection, AIDS, ARC (protease inhibitor) |
| T-20 | Trimeris | HIV infection, AIDS, ARC (fusion inhibitor) |
| T-1249 | | |
| BMS 232632 | Bristol-Myers-Squibb | HIV infection, AIDS, ARC (protease inhibitor) |
| IMMUNO-MODULATORS | | |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederie Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Rouss Immunex | AIDS |

-continued

| Drug Name | Manufacturer | Indication |
|---|---|---|
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |
| ANTI-INFECTIVES | | |
| Clindamycin with Primaquine | Pharmacia Upjohn | PCP |
| Fluconazole | Pfizer | cryptococcal meningitis, candidiasis prevention of oral candidiasis |
| Pastille Nystatin Pastille | Squibb Corp. | |
| Ornidyl Eflornithine | Merrell Dow | PCP |
| Pentamidine Isethionate (IM & IV) | LyphoMed (Rosemont, IL) | PCP treatment |

-continued

| Drug Name | Manufacturer | Indication |
|---|---|---|
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |
| OTHER | | |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/ADS |
| Soluble CD4 Protein and Derivatives | — | HIV infection |
| Testosterone | Alza, Smith Kline | AIDS-related wasting |
| Total Enteral Nutrition related to AIDS | Norwich Eaton Pharmaceuticals | diarrhea and malabsorption |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−)6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−)6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycenrdes. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are either commercially available, are made from known procedures or are prepared as illustrated.

SCHEME 1

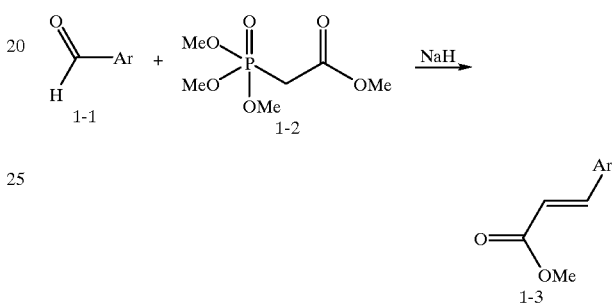

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

SCHEME 2

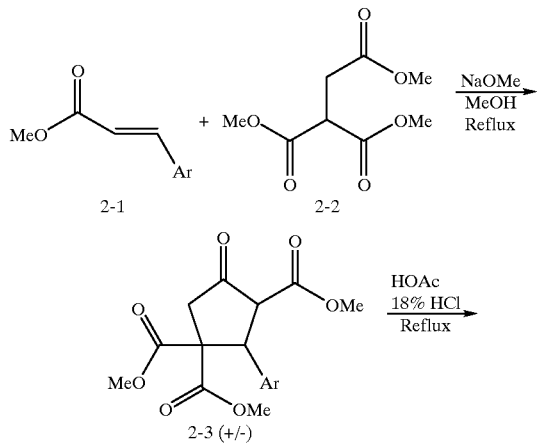

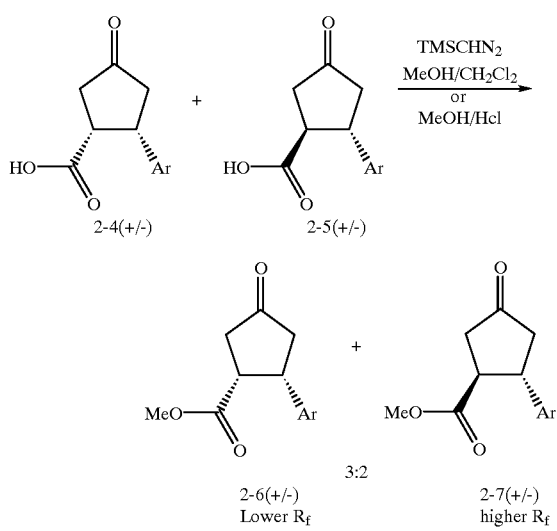

The preparation cyclopentane intermediates having a C-4-aryl substituent within the scope of the instant invention is detailed in Scheme 2 and as described by von A. W. Frahm, *Liebigs Ann. Chem.*, 1969, 728, 21. Treatment of a trans-cinnamic ester such as 2-1 (from Scheme 1) with trimethyl 1,1,2-ethanetricarboxylate (2-2) in the presence of an equivalent of an alkoxide base such as sodium methoxide in refluxing methanol gives the racemic cyclopentane keto-triester 2-3. Hydrolysis of the esters with HCl in acetic acid at reflux with concurrent double decarboxylation affords a mixture of the cis and trans keto-acids 2-4 and 2-5. The predominant initial product is the cis isomer 2-4, however, a better cis:trans ratio of products can be obtained with longer refluxing times. Thus, for example, after 72 h a 3:2 cis:trans ratio is achieved. Esterification of the mixture of acids can be done in a variety of ways, such as with trimethylsilyldiazomethane or acid catalyzed esterification in methanol. The isomers can readily be separated by chromatography and the cis/trans assignment for each is based on literatrure NMR data for 2-6 and 2-7.

SCHEME 3

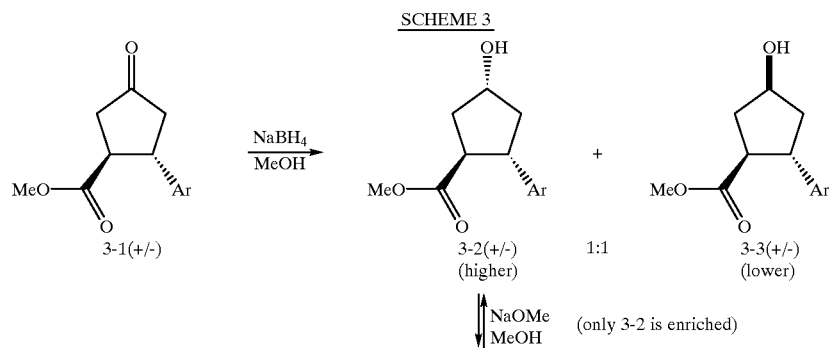

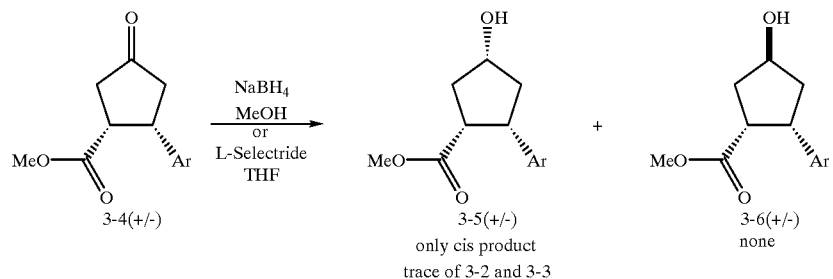

The preparation of further cyclopentane intermediates having a C-4 aryl substituent within the scope of the instant invention is detailed in Scheme 3. The trans ketone 3-1 (from Scheme 2) is reduced with sodium borohydride to a near 1:1 mixture of alcohols 3-2 and 3-3, while the cis ketone 3-4 (from Scheme 2) afforded a single cis product after reduction by either sodium borohydride or L-Selectride in THF. The structure 3-5 for the cis reduction product is based on the well established reduction of the cyclopentanones from the least hindered face. The assignment of the trans reduction products was then established by equilibra-

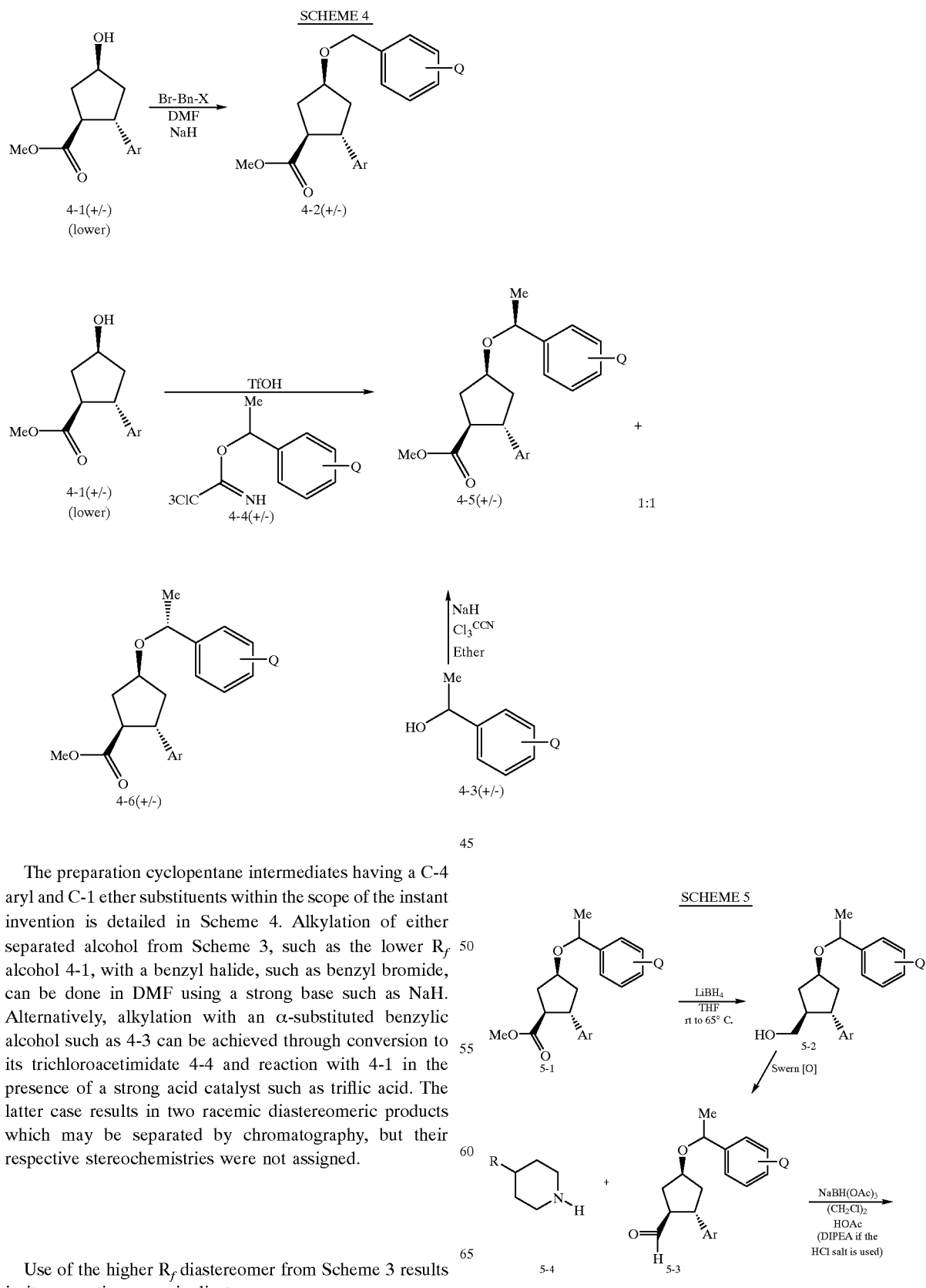

The preparation cyclopentane intermediates having a C-4 aryl and C-1 ether substituents within the scope of the instant invention is detailed in Scheme 4. Alkylation of either separated alcohol from Scheme 3, such as the lower $R_f$ alcohol 4-1, with a benzyl halide, such as benzyl bromide, can be done in DMF using a strong base such as NaH. Alternatively, alkylation with an α-substituted benzylic alcohol such as 4-3 can be achieved through conversion to its trichloroacetimidate 4-4 and reaction with 4-1 in the presence of a strong acid catalyst such as triflic acid. The latter case results in two racemic diastereomeric products which may be separated by chromatography, but their respective stereochemistries were not assigned.

Use of the higher $R_f$ diastereomer from Scheme 3 results in its respective racemic diastereomers.

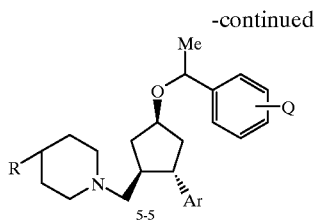

Preparation of some 1,3,4-trisubstituted cyclopentanes within the scope of the instant invention is given in Scheme 5. Reduction of ester 5-1 (from Scheme 4), for example, with lithium borohydride, diusobutylaluminum hydride, lithium aluminium hydride, or sodium bis(2-methoxyethoxy)aluminum hydride provides the primary alcohol 5-2. Oxidation to the aldehyde 5-3 can be carried out under numerous conditions, such with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 5-4 (see Schemes 12 and 13), using for example sodium triacetoxyborohydride or sodium cyanoborohydride in a suitable solvent such as methylene chloride, 1,2-dichloroethane, THF, acetonitrile or methanol, then provides a 3-((4-substitutedpiperidin-1-yl)methyl)cyclopentane derivative 5-5 which can itself be a chemokine receptor modulator or can be further modified as detailed below in Scheme 14.

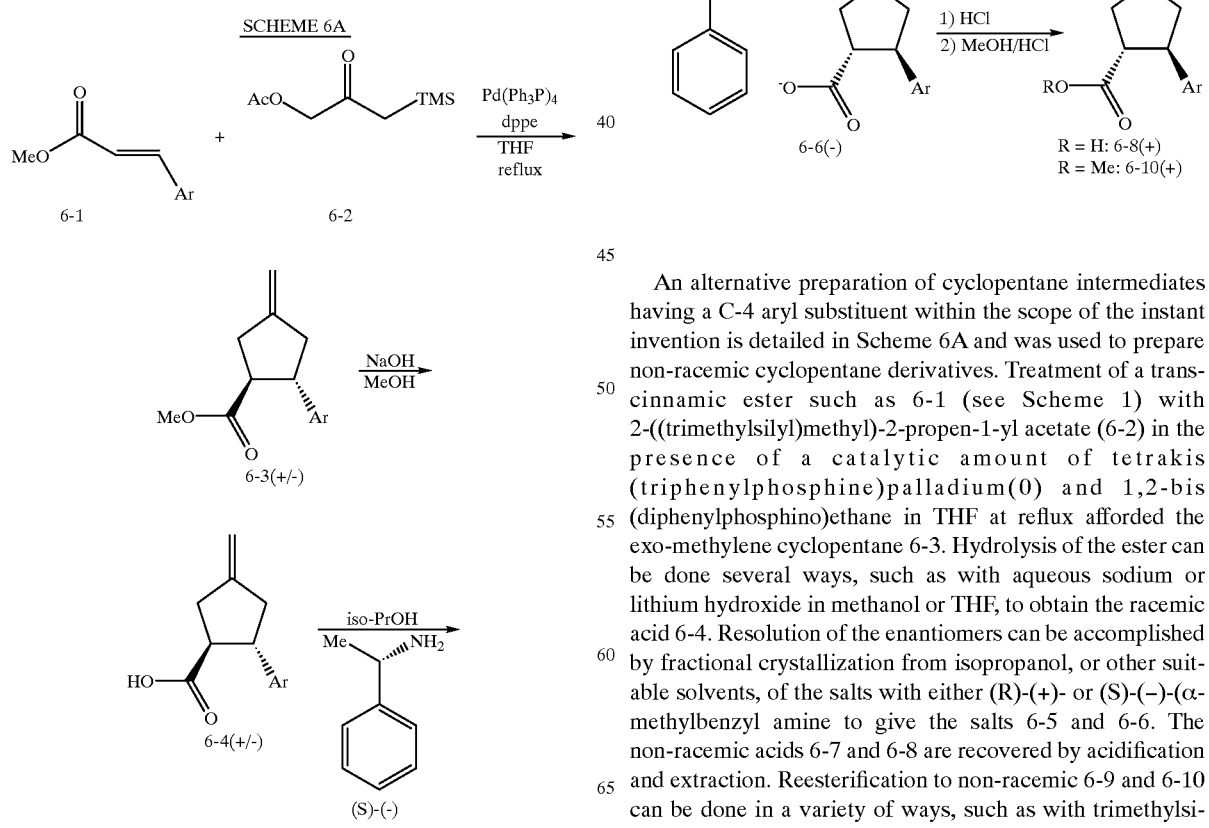

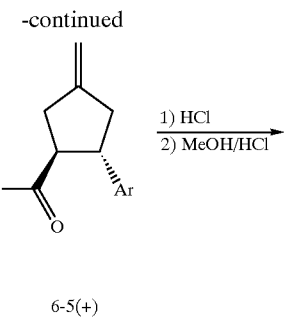

An alternative preparation of cyclopentane intermediates having a C-4 aryl substituent within the scope of the instant invention is detailed in Scheme 6A and was used to prepare non-racemic cyclopentane derivatives. Treatment of a trans-cinnamic ester such as 6-1 (see Scheme 1) with 2-((trimethylsilyl)methyl)-2-propen-1-yl acetate (6-2) in the presence of a catalytic amount of tetrakis(triphenylphosphine)palladium(0) and 1,2-bis(diphenylphosphino)ethane in THF at reflux afforded the exo-methylene cyclopentane 6-3. Hydrolysis of the ester can be done several ways, such as with aqueous sodium or lithium hydroxide in methanol or THF, to obtain the racemic acid 6-4. Resolution of the enantiomers can be accomplished by fractional crystallization from isopropanol, or other suitable solvents, of the salts with either (R)-(+)- or (S)-(−)-(α-methylbenzyl amine to give the salts 6-5 and 6-6. The non-racemic acids 6-7 and 6-8 are recovered by acidification and extraction. Reesterification to non-racemic 6-9 and 6-10 can be done in a variety of ways, such as with trimethylsilyldiazomethane or acid catalyzed esterification in methanol.

SCHEME 6B

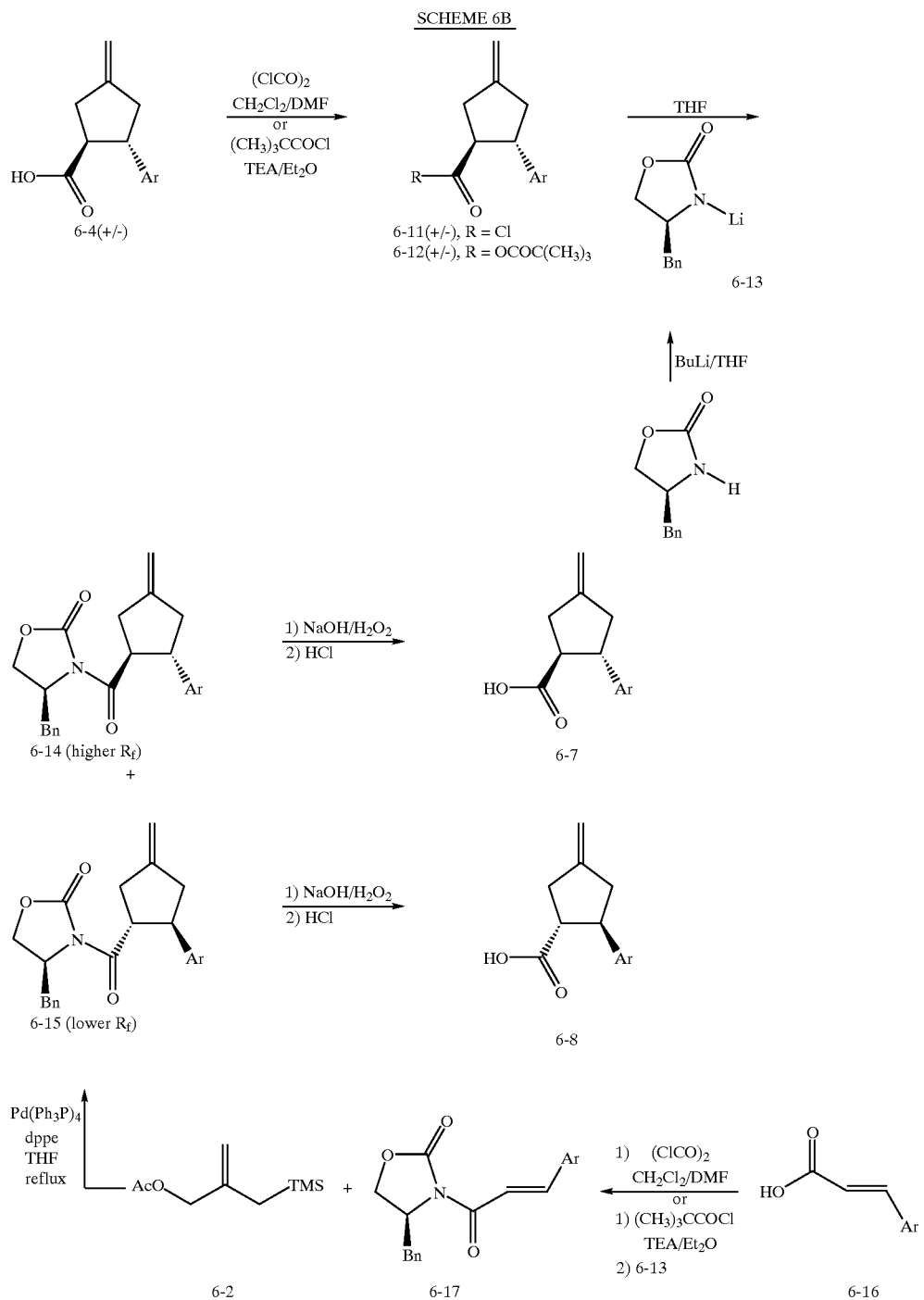

An alternative preparation of non-racemic cyclopentane intermediates having a C-4 aryl substituent within the scope of the instant invention is detailed in Scheme 6B. Conversion of the cyclopentane acid 6-4 (from Scheme 6A) to the acid chloride 6-11 under standard conditions, such as with oxalyl chloride in methylene chloride with a catalytic amount of DMF, or to the mixed anhydride 6-12, prepared in situ with trimethylacetyl chloride in ether with TEA as base, followed by reaction with the preformed lithium salt of (S)-(−)-4-benzyl-2-oxazolidinone 6-13, afforded the two non-racemic diastereomeric products 6-14 and 6-15, which are then separable by chromatography. Hydrolysis of each diastereomer under standard conditions, such as with lithium hydroxide and hydrogen peroxide, affords the two non-racemic acids 6-7 and 6-8. Alternatively, in order to obtain an enhanced amount of the desired diastereomer 6-14 before separation, similar conversion of the starting trans-cinnamic acid 6-16 (Scheme 1) to the chiral trans-cinnamate 6-17 followed by the ring formation reaction with 2-((trimethylsilyl)methyl)-2-propen-1-yl acetate (6-2) as detailed in Scheme 6A affords a 60:40 product mixture of 6-14:6-15.

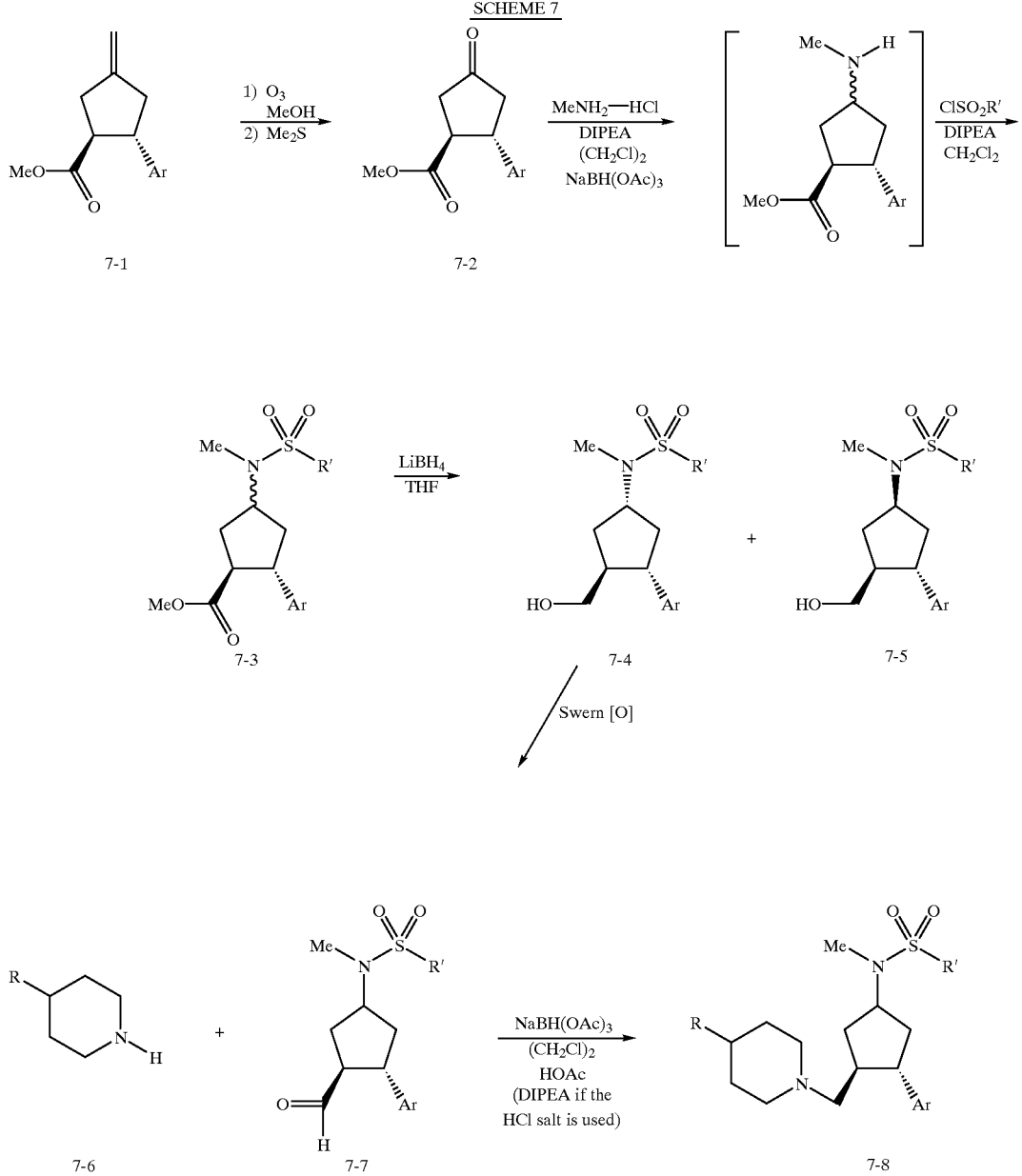

SCHEME 7

An alternative route for the preparation of some 1,3,4-trisubstituted cyclopentanes within the scope of the instant invention is given in Scheme 7. Oxidation of 7-1 (from Scheme 6A, either racemic or non-racemic) with ozone at −73° C. in an alcoholic solvent, such as methanol, followed by treatment with dimethyl sulfide affords the ketone 7-2 (same as racemic 2-7 in Scheme 2). Reductive alkylation of methylamine with 7-2, using for example sodium triacetoxyborohydride or sodium cyanoborohydride, followed by acylation with a sulfonyl chloride (or other acylation or sulfonylation reagent as detailed in Scheme 10) gives the sulfonamide 7-3 as a mixture of isomers. Reduction of the ester mixture, for example with lithium borohydride at rt to 65° C., provides the primary alcohol which is separated by chromatography into the two diastereomers at C-1, 7-4 and 7-5. Oxidation to the aldehyde(s) 7-7 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 7-6 (see Schemes 12 and 13), using for example sodium triacetoxyborohydride or sodium cyanoborohydride, then provides a 3-((4-substitutedpiperidin-1-yl)methyl)cyclopentane derivative 7-8 which can itself be a chemokine receptor modulator or can be further modified as detailed below in Scheme 14.

SCHEME 8

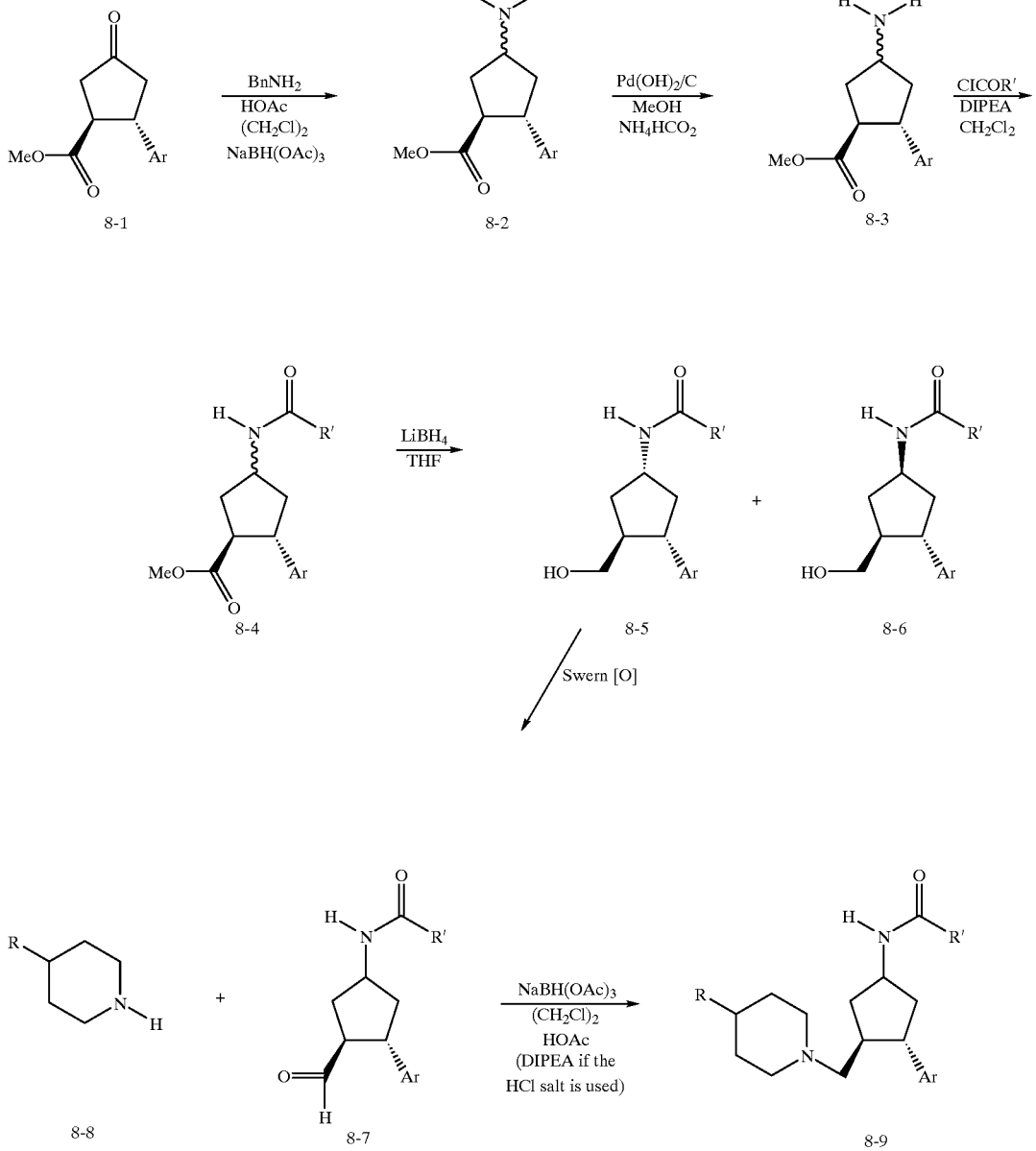

An alternative route for the preparation of some 1,3,4-trisubstituted cyclopentanes within the scope of the instant invention is given in Scheme 8. Reductive alkylation of benzylamine with 8-1 (from Scheme 2 or 6), using for example sodium triacetoxyborohydride or sodium cyanoborohydride, gives 8-2 which can be hydrogenated under standard conditions, such as in methanol in the presence of a palladium catalyst, for example Pd/C or Pearlman's catalyst, and using either hydrogen under pressure or ammonium formate at reflux, to afford the primary amine 8-3. Acylation with an acyl chloride (or other acylation or sulfonylation reagent as detailed in Scheme 10) gives the amide 8-4 as a mixture of isomers. Reduction of the ester mixture, for example with lithium borohydride at rt to 65° C., provides the primary alcohol which may be separated into the two diastereomers at C-1, 8-5 and 8-6. Oxidation to the aldehyde(s) 8-7 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 8-8 (see Schemes 12 and 13), using for example sodium triacetoxyborohydride or sodium cyanoborohydride, then provides a 3-((4-substitutedpiperidin-1-yl)methyl)cyclopentane derivative 8-9 which may itself be a chemokine receptor modulator or may be further modified as detailed below in Scheme 14.

SCHEME 9

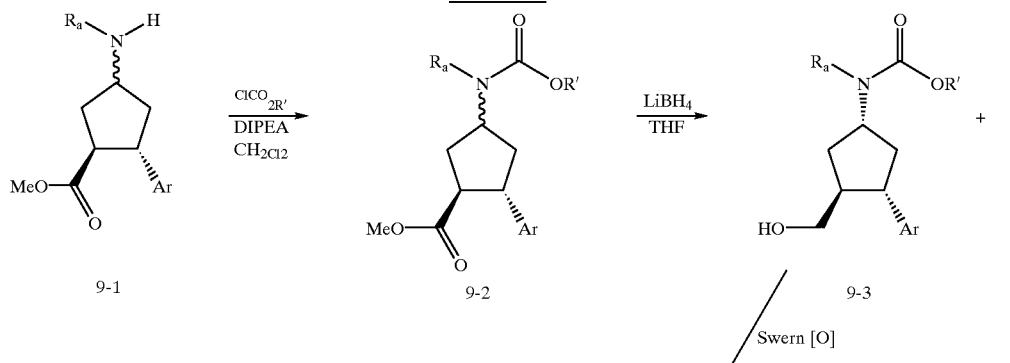

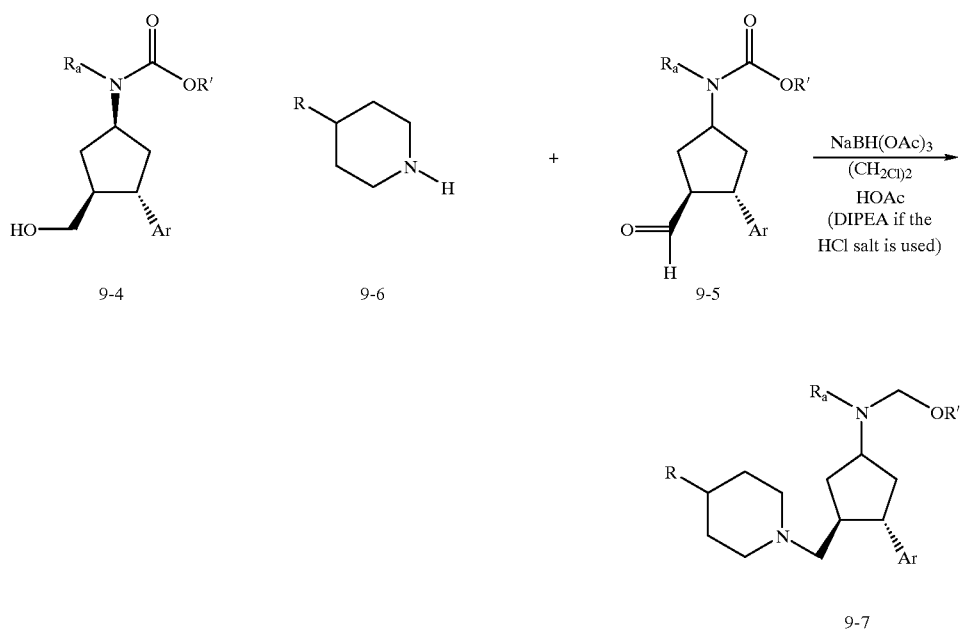

An alternative route for the preparation of some 1,3,4-trisubstituted cyclopentanes within the scope of the instant invention is given in Scheme 9. Acylation of the amine 9-1, usually as a mixture of isomers (from Scheme 7 or 8), with a chloroformate gives the carbamate 9-2. Reduction of the ester mixture, for example with lithium borohydride at rt to 65° C., provides the primary alcohol which may be separated into the two diastereomers at C-1, 9-3 and 9-4, if 9-1 started as a mixture. Oxidation to the aldehyde 9-5 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive amination with a cyclic amine, such as piperidine 9-6 (see Schemes 12 and 13), using for example sodium triacetoxyborohydride or sodium cyanoborohydride, then provides a 3-((4-substitutedpiperidin-1-yl)methyl)cyclopentane derivative 9-7 which may itself be a chemokine receptor modulator or may be further modified as detailed below in Scheme 14.

SCHEME 10

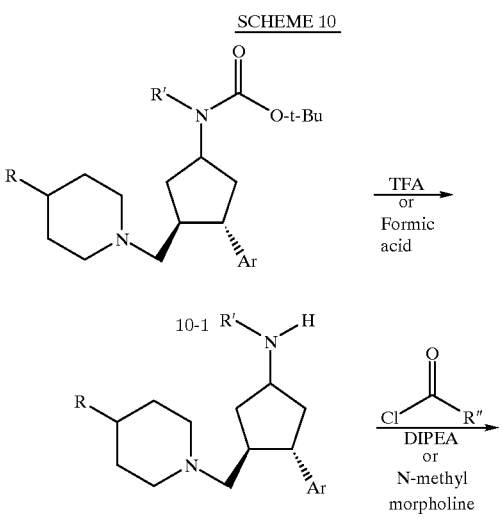

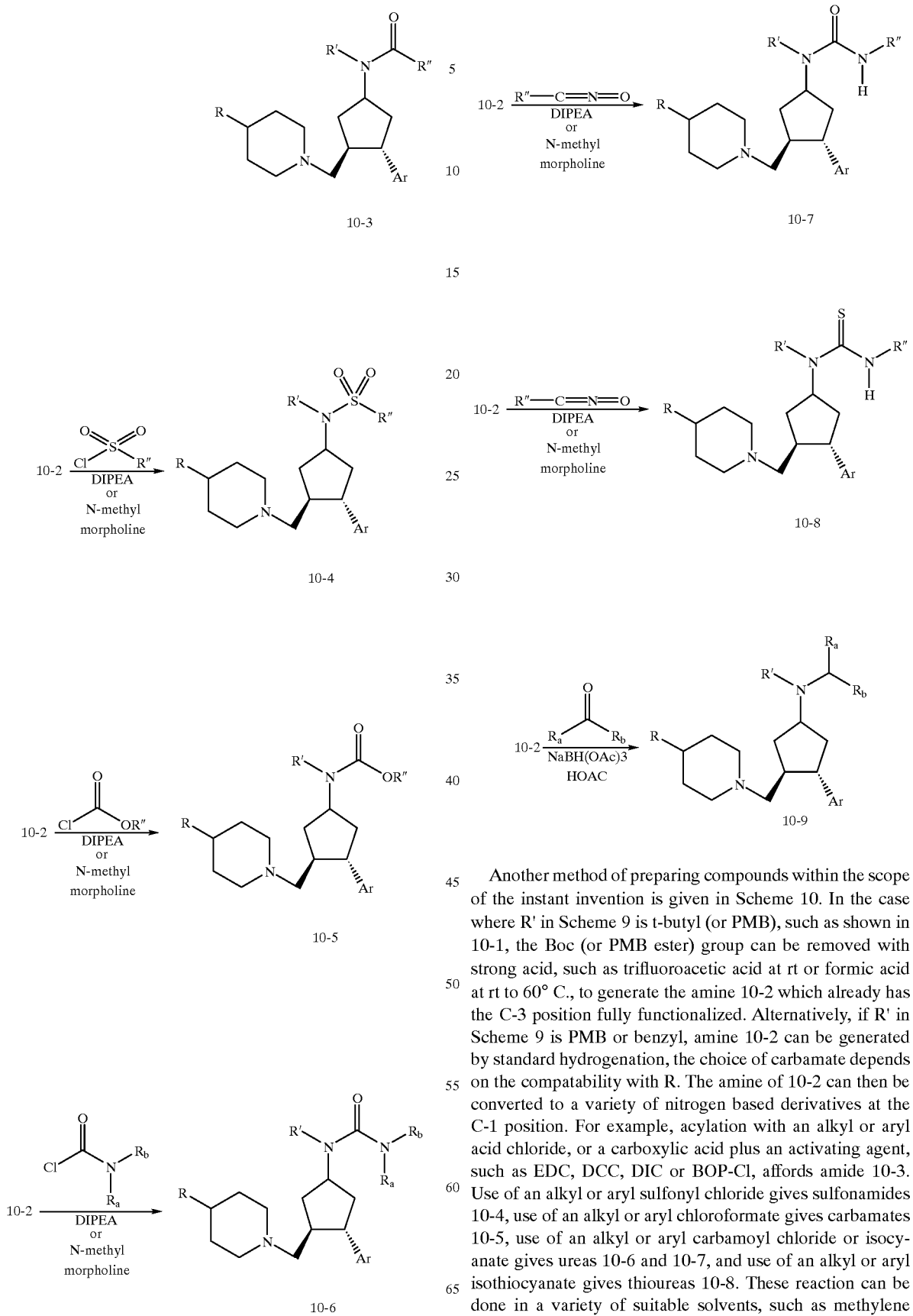

Another method of preparing compounds within the scope of the instant invention is given in Scheme 10. In the case where R' in Scheme 9 is t-butyl (or PMB), such as shown in 10-1, the Boc (or PMB ester) group can be removed with strong acid, such as trifluoroacetic acid at rt or formic acid at rt to 60° C., to generate the amine 10-2 which already has the C-3 position fully functionalized. Alternatively, if R' in Scheme 9 is PMB or benzyl, amine 10-2 can be generated by standard hydrogenation, the choice of carbamate depends on the compatability with R. The amine of 10-2 can then be converted to a variety of nitrogen based derivatives at the C-1 position. For example, acylation with an alkyl or aryl acid chloride, or a carboxylic acid plus an activating agent, such as EDC, DCC, DIC or BOP-Cl, affords amide 10-3. Use of an alkyl or aryl sulfonyl chloride gives sulfonamides 10-4, use of an alkyl or aryl chloroformate gives carbamates 10-5, use of an alkyl or aryl carbamoyl chloride or isocyanate gives ureas 10-6 and 10-7, and use of an alkyl or aryl isothiocyanate gives thioureas 10-8. These reaction can be done in a variety of suitable solvents, such as methylene chloride, dichloroethane, THF or methanol. For each of these reactions, an amine base is employed, such as TEA, DIPEA, n-methyl morpholine, pyridine or 2,6-lutidine. Alternatively, reductive alkylation with an aldehyde or ketone with a suitable reducing agent, such as sodium cyanoborohydride or sodium triacetoxyborohydride, in a suitable solvent, such as methylene chloride or dichloroethane, can afford the di-basic amine derivative 10-9.

amine, such as piperidine 11-5 (see Schemes 12 and 13) with 11-4, using for example sodium triacetoxyborohydride or sodium cyanoborohydride, then provides a 3-((4-substitutedpiperidin-1-yl)methyl)cyclopentane derivative 11-6. Oxidation of the exo-methylene of 11-6 to a ketone 11-7 can be done on the hydrochloride salt of 11-6 in methanol with ozone at −73° C. followed by dimethyl sulfide work-up. Reductive alkylation of a primary or sec-

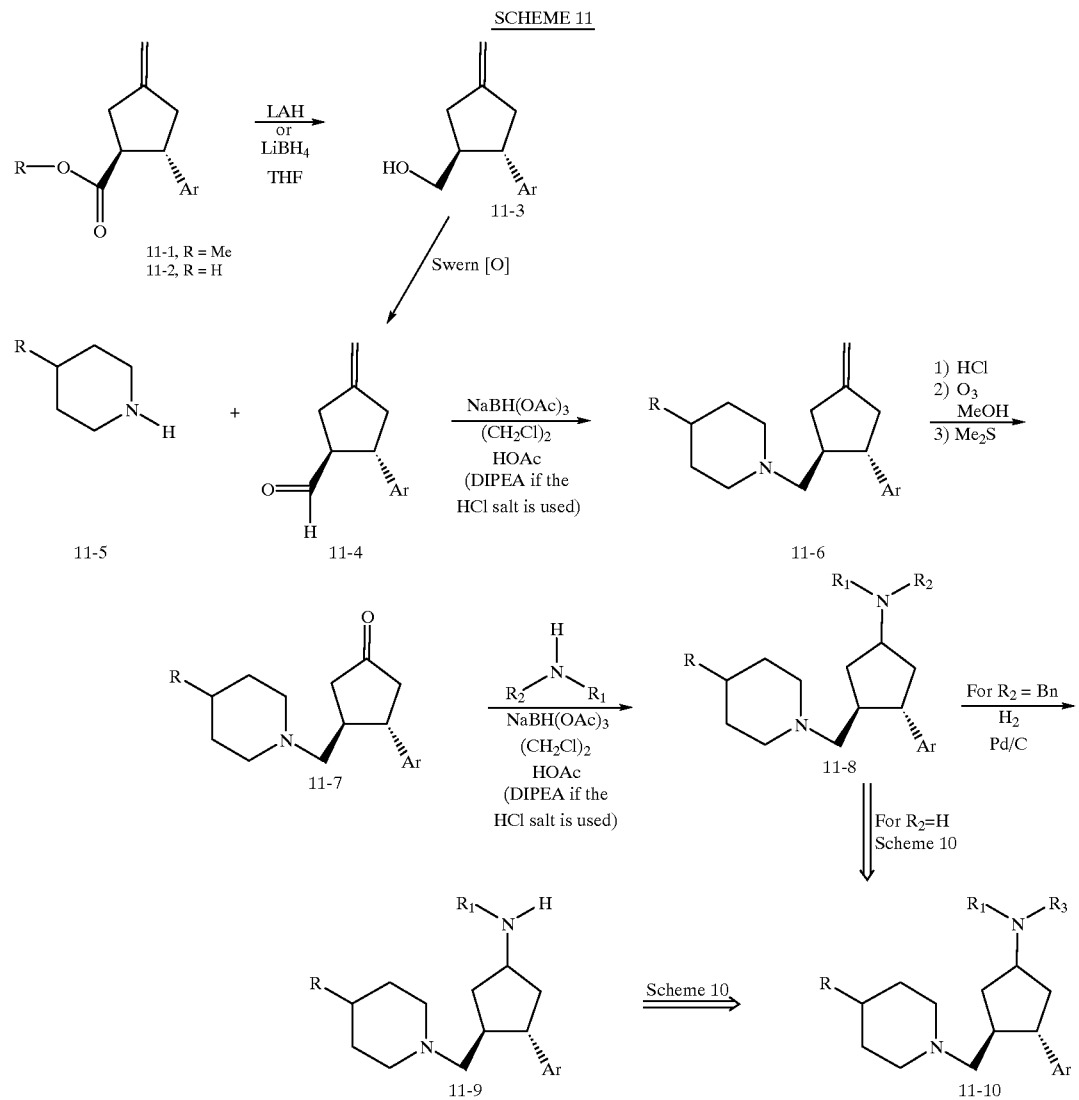

Another method of preparing compounds within the scope of the instant invention is given in Scheme 11. Reduction of either ester 11-1 with lithium aluminum hydride or lithium borohydride or acid 11-2 with lithium aluminum hydride affords the exo-methylene alcohol 11-3. Oxidation 11-3 to the aldehyde 11-4 can be carried out under numerous conditions, such as with DMSO and oxalyl chloride at low temperature, followed by triethylamine (Swern oxidation), with the Dess-Martin periodinane, or with various chromium trioxide-based reagents (see March J. "Advanced Organic Chemistry", 4th ed., John Wiley & Sons, New York, pp. 1167–1171 (1992)). Reductive alkylation of a cyclic ondary amine with 11-7 using for example sodium triacetoxyborohydride or sodium cyanoborohydride affords the amine 11-8 which itself can be a chemokine receptor modulator or can be further modified as already detailed in Schemes 7-10. Thus, if $R_2$ of 11-8 is H, further functionalization of 11-8 as detailed in Scheme 10 can afford 11-10 as other examples of chemokine receptor modulators. Alternatively, if $R_2$ is benzyl or some other amine protecting group, and the piperidine substituent R is stable to hydrogenation or other means for removing the $R_2$ group to give 11-9, then further functionalization to 11-10 is also possible.

SCHEME 12

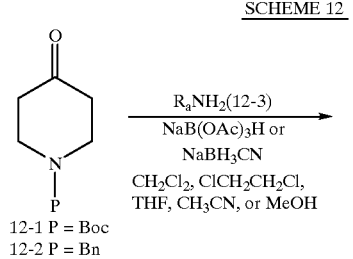

12-1 P = Boc
12-2 P = Bn

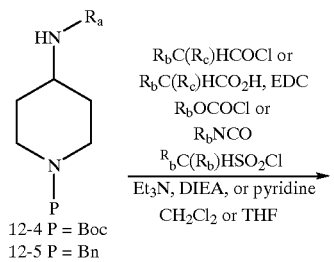

12-4 P = Boc
12-5 P = Bn

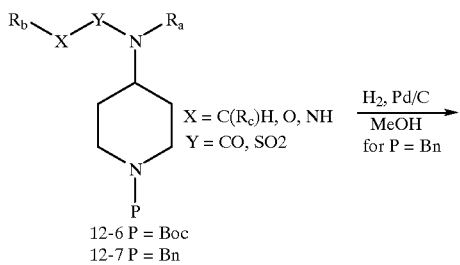

12-6 P = Boc
12-7 P = Bn

X = C(R$_c$)H, O, NH
Y = CO, SO2

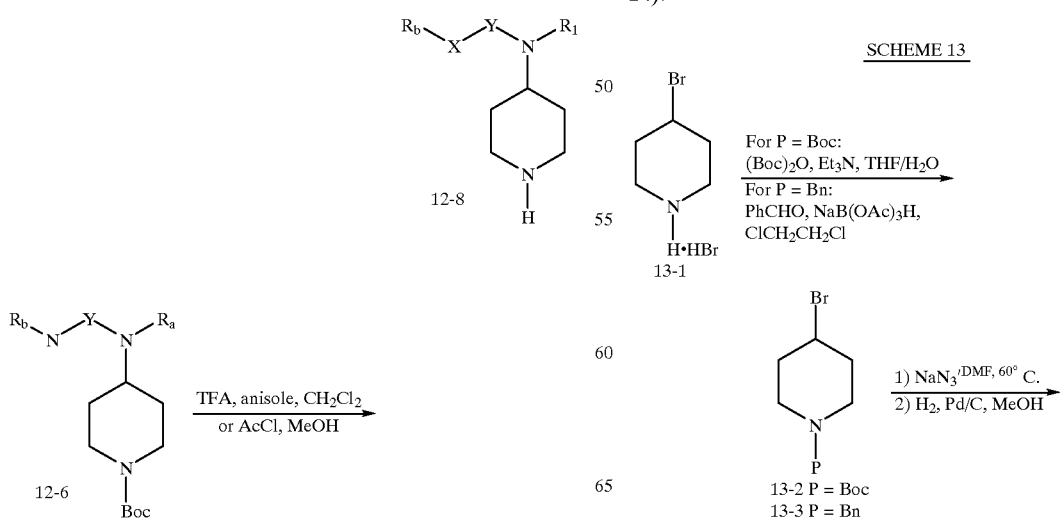

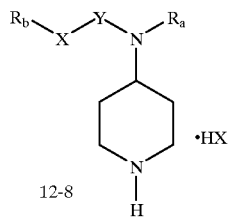

12-8

Synthetic routes for the preparation of piperidines bearing a 4-substituent containing an amide, carbamate, sulfonamide or urea functional group are given in Scheme 12. Reductive amination of commercially available 12-1 or 12-2 with primary amine 12-3 in the presence of sodium triacetoxyborohydride or sodium cyanoborohydride in a suitable solvent (for example, methylene chloride, 1,2-dichloroethane, THF, acetonitrile, or methanol) provides amines 12-4 or 12-5. Acylation is then carried out with an acyl chloride (or a carboxylic acid plus an activating agent, such as EDC, DCC, or BOP-Cl) to provide 12-6 or 12-7 as an amide. Alternatively, acylation with a chloroformate provides 12-6 or 12-7 as a carbamate. Treatment of 12-4 or 12-5 with an isocyanate affords 12-6 or 12-7 as a urea. Treatment of 12-4 or 12-5 with a sulfonyl chloride affords 12-6 or 12-7 as a sulfonamide. For each of these reactions, an amine base is employed, such as triethylamine, DEEA, pyridine, or 2,6-lutidine. In the case of the benzyl-protected derivative 12-7, hydrogenolysis under standard conditions (for example, hydrogen in the presence of palladium on carbon in methanol or ethanol) provides the desired intermediate 12-8. For the N-Boc compound 12-6, exposure to suitable anhydrous acidic conditions (for example trifluoroacetic acid and anisole in methylene chloride at temperatures from 0–25 degrees C.) affords the salt of 12-8. This compound is then utilized as the cyclic secondary amine component as shown above in Schemes 5, 7, 8, 9, and 11. Alternatively, if no functionality are present in the alkyl cyclopentane framework that would be adversely effected by the above mentioned chemistry, then 4-piperidone may be attached directly to the alkyl cyclopentane framework described above, and the chemistry described in this paragraph can be carried out equating the alkyl cyclopentane segment to the group 'P' given in Scheme 12, structures 1 through 7 (also see Scheme 14).

SCHEME 13

-continued

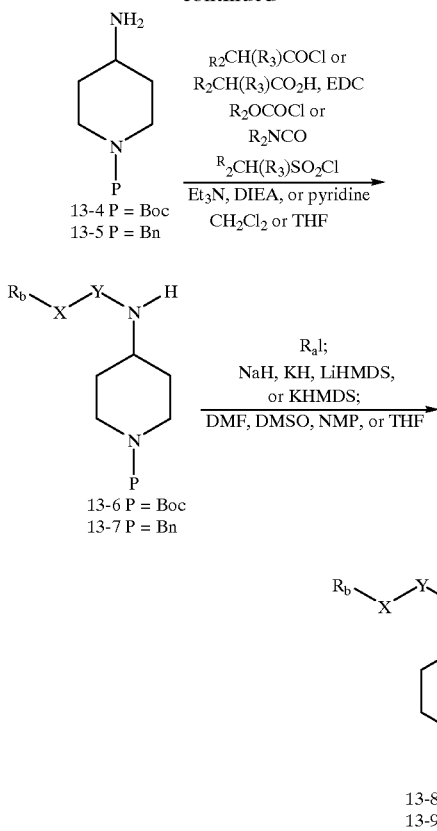

13-4 P = Boc
13-5 P = Bn 13-6 P = Boc
13-7 P = Bn 13-8 P = Boc
13-9 P = Bn

X = C(R₃)H, O, NH
Y = CO, SO₂

Alternate synthetic routes for the preparation of piperidines bearing a 4-substituent containing an amide, carbamate or urea functional group are given in Scheme 13. Protection of 4-bromopiperidine can be carried out with several protecting groups for nitrogen. For example, using standard conditions, protection with a Boc group gives 13-2, whereas reductive amination with benzaldehyde yields the N-benzyl derivative 13-3. Displacement of the bromide with sodium azide in warm to hot DMF provides the 4-azidopiperidine derivative, and reduction of the azide with hydrogen in the presence of a palladium catalyst (for the Boc protected intermediate) or with triphenylphosphine followed by hydrolysis (for N-benzyl protected intermediate) provides the aminopiperidine 13-4 or 13-5. Acylation is then carried out with an acyl chloride (or a carboxylic acid plus an activating agent, such as EDC, DCC, or BOP-Cl) to provide 13-6 or 13-7 as an amide. Alternatively, acylation with a chloroformate provides 13-6 or 13-7 as a carbamate. Treatment of 13-4 or 13-5 with an isocyanate affords 13-6 or 13-7 as a urea. Treatment of 13-4 or 13-5 with a sulfonyl chloride affords 13-6 or 13-7 as a sulfonamide. For each of these reactions, an amine base is employed, such as triethylamine, DIEA, pyridine, or 2,6-lutidine. When Q=C(R_c)H or O, compounds 13-6 and 13-7 may optionally be alkylated by treatment with a base such as sodium hydride, potassium hydride, LiHMDS, KHMDS, or NAHMDS followed by treatment with an alkyl iodide, allyl halide, or propargyl halide. Solvents such as DMF, DMSO, N-methylpyrrolidine or THF are suitable. These procedures provide carbamate, sulfonamide or amide 13-8 and 13-9. Removal of the protecting groups is then carried out as shown in Scheme 12 above, and the resulting 1-unsubstituted piperidines are then utilized as noted in the descriptions for Schemes 5, 7, 8, 9, and 11.

SCHEME 14

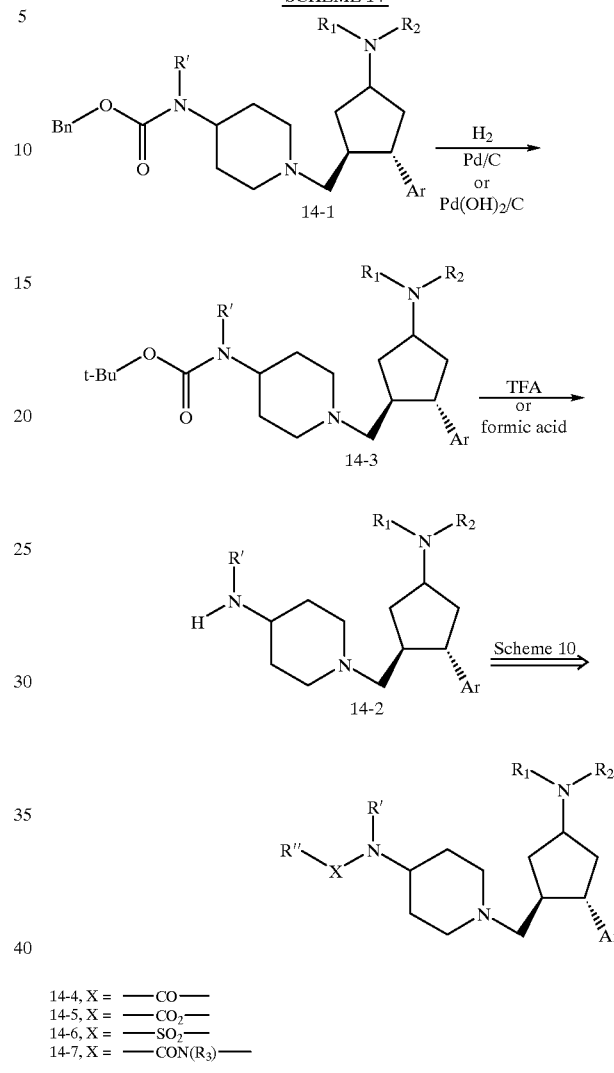

14-4, X = —CO—
14-5, X = —CO₂—
14-6, X = —SO₂—
14-7, X = —CON(R₃)—

Another method of preparing compounds within the scope of the instant invention is given in Scheme 14. When the R substituent on the cyclic amine portion in Scheme 5, 7, 8, 9 or 11 is a N-(benzyloxycarbonyl)-N-(alkyl)amino as in 14-1, removal of the benzyloxycarbonyl group by hydrogenation with Pd/C or Pearlman's catalyst in the presence of hydrogen, ammonium formate or other hydrogen transfer reagent can be done to afford the amine 14-2, as long as the functionality at C-1 of the cyclopentyl ring is stable to the hydrogenation conditions. Alternatively, when the R substituent on the cyclic amine portion is a N-(t-butoxycarbonyl)-N-(alkyl)amino as in 14-3, deprotection of 14-3 with strong acid such as TFA or formic acid at rt to 60° C. will again give 14-2, as long as the functionality at C-1 of the cyclopentyl ring is stable to the acidic conditions. The exposed amine can then be re-functionalized with a variety of alkyl or aryl acyl or sulfonyl groups (same as in Scheme 10) to afford other examples of chemokine receptor modulators, such as amides 14-4, carbamates 14-5, sulfonamides 14-6 and ureas 14-7.

SCHEME 15

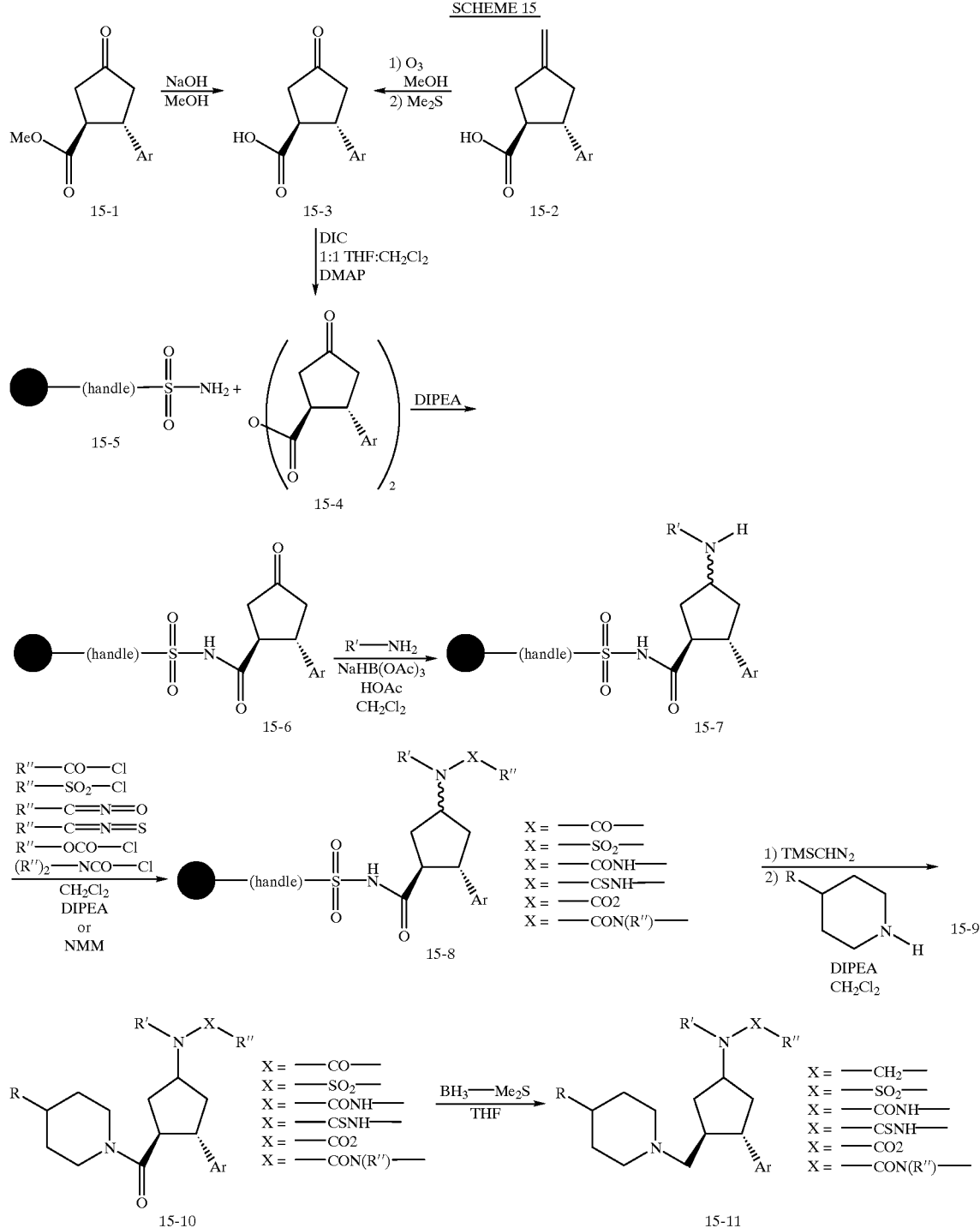

Another method of preparing compounds within the scope of the instant invention is given in Scheme 15 in which most of the chemistry is done on a resin. This linker methodology employed is that as described by G. W. Kenner, *J. Chem. Soc., Chem. Comm.*, 1971, 636 or any other suitable sulfonamide linker known in the art. Thus, the keto-acid 15-3, prepared either by standard hydrolysis of the ester 15-1 (from Scheme 2 or 7) or oxidation of the exo-methylene of 15-2 (from Scheme 6A or 6B) with ozone in methanol at −70° C. followed by treatment with dimethyl sulfide, is first activated as its anhydride 15-4 by treatment with a dehydrating agent, such as dicyclohexylcarbodiimide or diisopropylcarbodiimide, in a suitable solvent, such as THF or methylene chloride or a mixture of these, with a catalytic amount of DMAP. Reaction of 15-4 with the Kenner sulfonamide linker 15-5 (4-sulfamylbenzoyl AM resin, Novabiochem, cat.# 01-64-0121), affords the resin-bound cyclopentanone 15-6. Reductive amination under standard conditions, such as with sodium triacetoxyborohydride in THF or 1,2-dichloroethane, of various amines with 15-6 affords the resin-bound amino derivative 15-7. Acylation or sulfonylation can be done under standard conditions, such as with alkyl or aryl acid chlorides, sulfonyl chlorides, isocyanates, isothiocyanates, chloroformates, carbamoyl chlorides or other standard acylating agent, usually in the presence of an amine base, such as triethylamine, diisopropylethylamine, N-methylmorpholine, or pyridine, to afford the resin-bound amine derivative 15-8. Activation of the resin sulfonamide linker with trimethylsilyldiazomethane and displacement with an amine, such as the piperidine 15-9 (see Schemes 12 and 13) in which R must be stable to borane-dimethyl sulfide reduction, gives the corresponding amide 15-10. Subsequent reduction of the amide 15-10 with borane-dimethyl sulfide can then afford a variety of examples of chemokine receptor modulators. If the C-1 amine derivative in 15-10 (—N—X—) is also reducible under these conditions, then a corresponding diamine 15-11 (X=CH$_2$) will be obtained which can also be a chemokine receptor modulator. Alternatively, the diamine 15-11 (X=CH$_2$) could have been obtained using a second reductive amination step in place of the acylation reaction. Alternatively, for the preparation of amine derivatives which are not stable to the diborane-methyl sulfide conditions, such as for the amide moiety (15-10, X=—CO—), the acylation step can be done after the cleavage/reduction sequence as detailed in Scheme 10. When either R or R' are suitable for further elaboration as detailed in Schemes 10 or 14, additional derivatives can also be prepared.

SCHEME 16

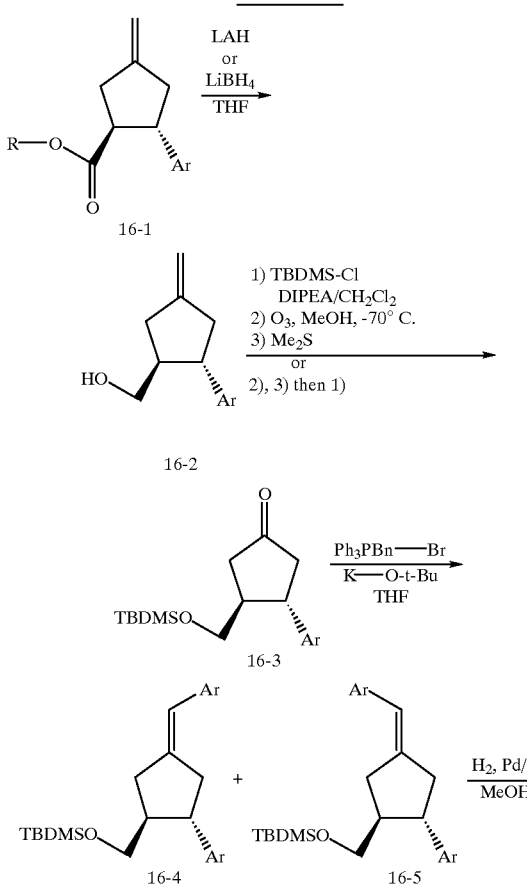

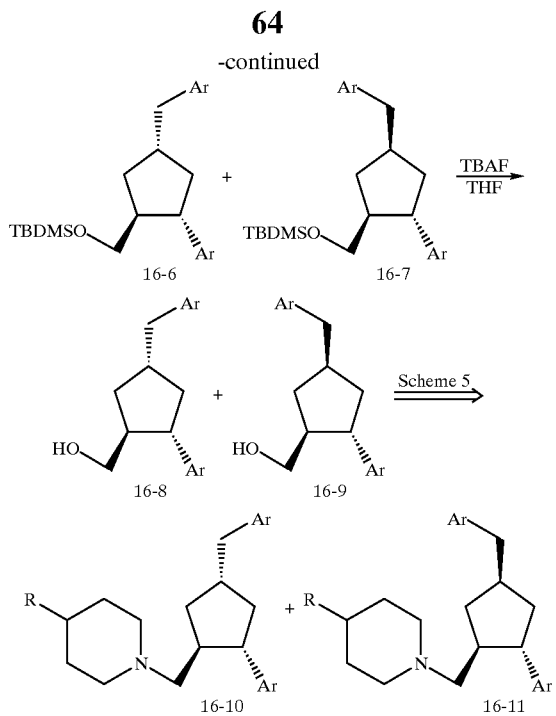

Another method of preparing compounds within the scope of the instant invention is given in Scheme 16. Reduction of the ester 16-1 (R=Me, from Scheme 6A) with either LAH or LiBH$_4$ in THF affords the alcohol 16-2. Alternatively, reduction of the acid 16-1 (R=H, from Scheme 6A or 6B) with LAH in THF can also afford 16-2. Silylation of the alcohol with TBDMS-Cl in THF or methylene choride in the presence of a base, such as TEA or DIPEA, followed by oxidation of the exo-methylene with ozone in methanol at reduced temperature, such as at −70° C., using a reductive work-up with dimethylsulfide gives the protected alcohol-ketone 16-3. Alternatively, the silylation and oxidation steps can be reversed. Reaction of the ketone of 16-3 with benzyltriphenylphophonium bromide in the presence of a base such as potassium t-butoxide gives a mixture of the benzylidene isomers 16-4 and 16-5 which may be separable by chromatographic methods at this step or at a later stage. Hydrogenation under standard conditions with Pd/C or Pearlman's catalyst in methanol affords the benzyl derivatives 16-6 and/or 16-7. The silyl ether can then be removed under standard conditions with acidic methanol or TBAF in THF to afford the alcohols 16-8 and/or 16-9 which also may be separable by chromatographic methods. Alternatively, the hydrogenation and silyl removal may be interchanged. The alcohols 16-8 and/or 16-9 can be converted to the final product(s) 6-10 and 6-11 as shown in Scheme 5.

SCHEME 17

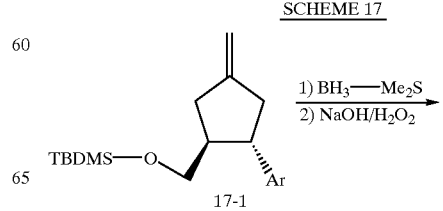

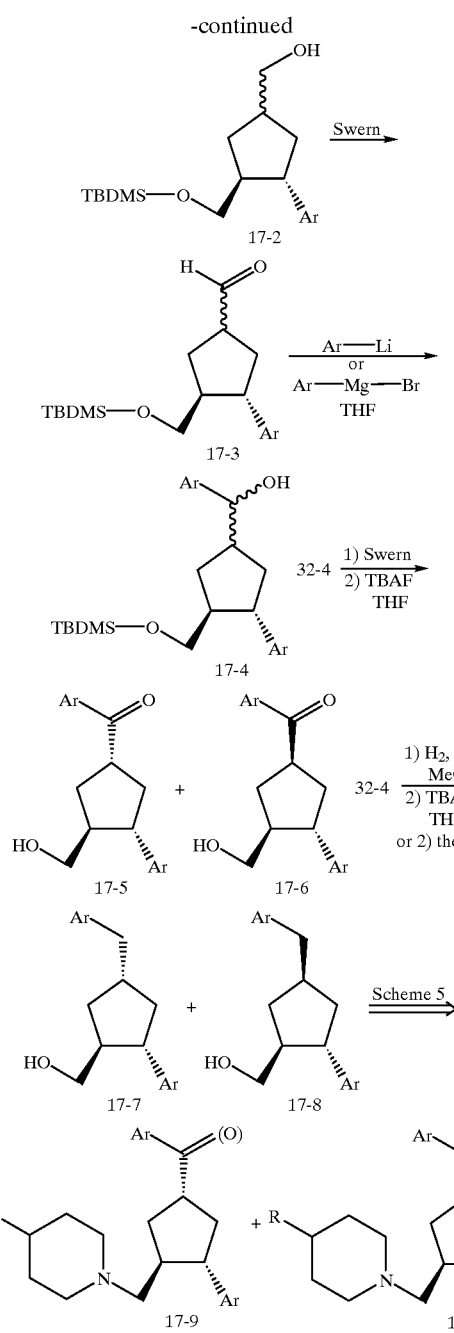

Reoxidation again using Swern conditions followed by desilylation gives the aroyl derivatives which may be separable by chromatographic methods to afford the individual C-1 isomers 17-5 and 17-6. Alternatively, 17-4 can be catalytically reduced under standard conditions with Pd/C or Pearlman's catalyst in methanol to afford the arylmethyl derivatives 17-7 and 17-8 after desilylation. These may be separable by chromatographic methods and gives an alternative preparation of 16-6 and 16-7 as shown in Scheme 16. Alternatively, the hydrogenation and silyl removal may be interchanged. The alcohols 17-5 and/or 17-6 and 17-7 and/or 17-8 can be converted to the final product(s) 17-9 and 17-10 as shown in Scheme 5.

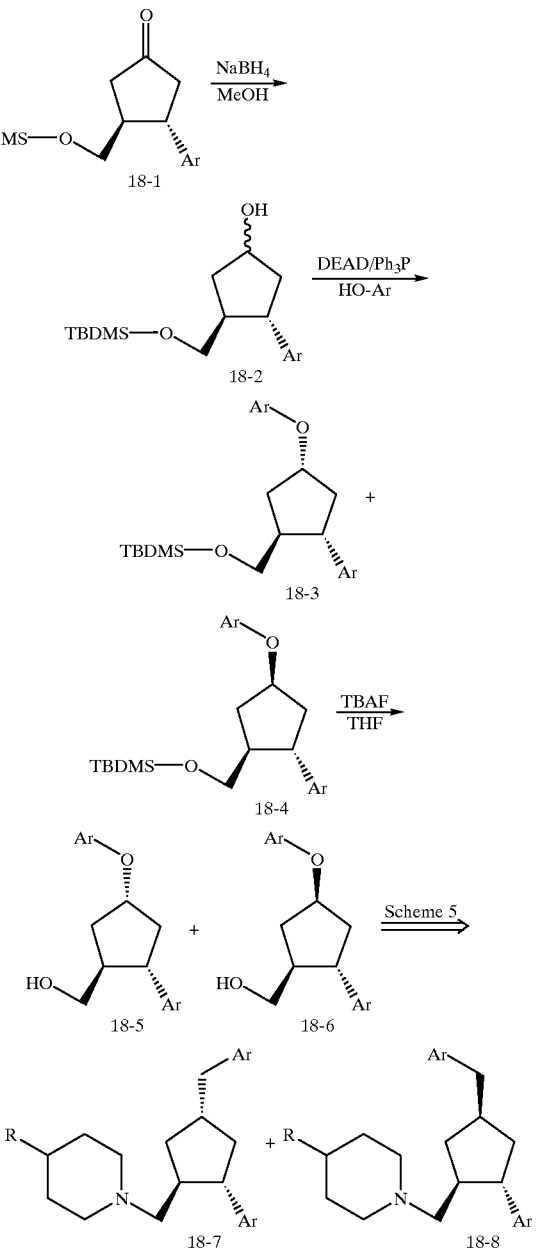

Another method of preparing compounds within the scope of the instant invention is given in Scheme 17. Hydroborantion of 17-1 (see Scheme 16) using borane-THF or borane-Me$_2$S complex in THF followed by a standard oxidative work-up with sodium hydroxide and hydrogen peroxide or trimethylamine-N-oxide affords the C-1 hydroxymethyl compound 17-2 as a mixture of C-1 isomers. Oxidation to the aldehyde 17-3 can be done under Swern conditions or with a variety of other reagents (see above). Addition of an aryl lithium (commercially available or prepared from the aryl iodide or bromide and t-butyl lithium in THF at reduced temperature, such as at −78° C.) or an aryl magnesium iodide or bromide (Grignard reagent) (commercially available or prepared from the aryl iodide or bromide and magnesium in THF or ether) to the aldehyde 17-3 gives a mixture of the four possible C-1 and C-1' isomers 17-4.

Another method of preparing compounds within the scope of the instant invention is given in Scheme 18. Reaction of the silyl-ketone 18-1 (see Scheme 16) with NaBU4 in methanol under standard conditions gives 18-2 as a mixture of isomers. Reaction of 18-2 with a hydroxyaryl in the presence of triphenylphosphine and DEAD leads to the formation of the ethers 18-4 and 18-5 which may be separable by chromatographic methods either before or after the desilylation to 18-5 and/or 18-6. The alcohols 18-5 and/or 18-6 can be converted to the final product(s) 18-7 and 18-8 as shown in Scheme 5.

In some cases the order of carrying out the foregoing reaction schemes may be varied to facilitate the reaction or to avoid unwanted reaction products. The following examples are provided for the purpose of further illustration only and are not intended to be limitations on the disclosed invention.

General

Concentration of solutions was carried out on a rotary evaporator under reduced pressure. Flash chromatography was carried out on silica gel (230–400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC Conditions

HPLC A. Retention time using the following conditions: Column: YMC ODS A, 5$\mu$, 4.6×50 mm; Gradient Eluant: 10:90 to 90:10 v/v $CH_3CN/H_2O$+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5$\mu$ 4.6×100 mm column; Gradient Eluant: 10:90 to 90:10 v/v $CH_3CN/H_2O$+0.5% TFA over 10 min, hold 2 min; Detection: PDA, 200–400 nm; Flow Rate: 2.25 mL/min.

Procedure 1

4-(N-(t-Butoxycarbonyl)-N-(ethyl)amino)piperidine
Step A: (1-Benzyloxycarbonylpiperidin-4-yl)isocyanate To a solution of 9.72 g (34.8 mmol) of 1-benzyloxycarbonyl-4-carboxypiperidine in 100 mL of methylene chloride was added 2 drops of DMF and then slowly 3.34 mL (38.3 mmol) of oxalyl chloride. The reaction was stirred at rt for 1 h (gas evolution had stopped) and the volatiles were removed in vacuo followed by evaporation of a portion of toluene.

The above residue was taken up in 100 mL of acetone and slowly added to a solution of 5.66 g (87 mmol) of sodium azide in 25 mL of water and 25 mL of acetone while stirred in an ice bath. The reaction was stirred at 0° C. for 1.5 h and then diluted with ice water and extracted twice with 2×50 mL of toluene. The organic layers were each washed with a portion of brine, dried over sodium sulfate, combined and concentrated to about 100 mL in vacuo with a minimum of heating. The remaining solution was slowly heated to 85° C. for 1.5 h and then concentrated to dryness in vacuo to afford about 9.5 g of crude title product which can be used directly in subsequent reactions.

Step B: 1-Benzyloxycarbonyl-4-(t-butoxycarbonylamino) piperidine

A solution of 3.2 g (12.3 mmol) of (1-benzyloxycarbonylpiperidin-4-yl)isocyanate from Step A in 25 mL of DMF was slowly added to a suspension of $CuCl_3$ in 25 mL of DMF and 12 mL of t-butanol. The reaction was stirred for 24 h and then diluted with water and extracted twice with 1:1 ether:ethyl acetate. The organic layers were each washed with a portion of water and brine, dried over sodium sulfate, combined and concentrated. The residue was purified by FC eluting with 20% ethyl acetate in hexanes to afford 685 mg of title compound.

$^1$H NMR (400 MHz, $CDCl_3$): δ 1.26 (m, 2H), 1.42 (s, 9H), 1.90 (br d, J=12, 2H), 2.90 (br t, 2H), 3.58 (m, 1H), 4.08 (m, 2H), 4.42 (br s, 1H), 5.09 (s, 2H), 7.33 (m, 5H).

Step C: 1-Benzyloxycarbonyl-4-(N-(t-butoxycarbonyl-N-(ethyl)amino)piperidine

To a solution of 476 mg (1.42 mmol) of 1-benzyloxycarbonyl-4-(t-butoxycarbonylamino)piperidine from Step B and 0.24 mL (2.8 mmol) of ethyl iodide in 10 mnL of DMF was added 85 mg (2.1 mmol) of 60% sodium hydride in mineral oil. The reaction was stirred for 16 h and was then poured into water and extracted three times with ether. The organic layers were each washed with a portion of water and brine, dried over sodium sulfate, combined and concentrated. The residue was purified by FC eluting with 15% ethyl acetate in hexanes to afford 409 mg of title compound.

$^1$H NMR (400 MHz, $CDCl_3$): δ 1.06 (t, J=7, 3H), 1.44 (s, 9H), 1.5–1.7 (2 m, 4H), 2.78 (m, 2H), 3.1 (m, 2H), 4.10 (m, 1H), 4.25 (m, 2H), 5.10 (s, 2H), 7.33 (m, 5H).

Step D: 4-(N-(t-Butoxycarbonyl)-N-(ethyl)amino) piperidine

A solution of 400 mg (1.1 mmol) of 1-benzyloxycarbonyl-4-(N-(-t-butoxycarbonyl-N-(ethyl) amino)piperidine from Step C in 4 mL of methanol was hydrogenated with 40 mg of 10% Pd/C under a hydrogen balloon for 16 h. The reaction was filtered and concentrated in vacuo to give the title compound which was used directly in the next step.

Procedure 2

4-(N-Methoxycarbonyl-N-(ethyl)amino)piperidine
Step A: 1-Benzyloxycarbonyl-4-(methoxycarbonylamino) piperidine To a solution of 1.0 g (3.9 mmol) of (1-benzyloxycarbonylpiperidin-4-yl)isocyanate from Procedure 1, Step A in 10 mL of methanol was added 5 mg (cat) of DMAP. The reaction was stirred under nitrogen at rt for 24 h and then poured into water containing 2 mL of 2 N hydrochloric acid and was extracted twice with ethyl acetate. The organic layers were each washed with a portion of brine, dried over sodium sulfate, combined and concentrated to give 1.4 g of the crude title compound which can be used directly in subsequent reactions.

$^1$H NMR (400 MHz, $CDCl_3$): δ 1.32 (m, 2H), 1.92 (br d, J=10, 4H), 2.91 (v br t, 2H), 3.66 (br s, 3H), 4.10 (m, 1H), 4.58 (br s, 1H), 5.09 (s, 2H), 7.33 (m, 5H).

Step B: 1-Benzyloxycarbonyl-4-(N-methoxycarbonyl(N-ethyl)amino)piperidine

To 82 mg (0.28 mmol) of 1-benzyloxycarbonyl-4-(methoxycarbonylamino)piperidine from Step A and 0.045 mL (0.56 mmol) of ethyl iodide in 4 mL of DMF under nitrogen was added 22 mg (0.56 mmol) of 60% sodium hydride in mineral oil. The reaction was stirred at rt for 1 h and was then poured into water containing 1 mL of 2 N hydrochloric acid and extracted twice with ether. The organic layers were each washed with a portion of brine, dried over sodium sulfate, combined and concentrated. The residue was purified by FC eluting with 50% ethyl acetate in hexanes to afford 87 mg of title compound.

$^1$H NMR (400 MHz, $CDCl_3$): δ 1.07 (t, J=7, 3H), 1.5–1.8 (m, 4H), 2.79 (m, 2H), 3.15 (m, 2H), 3.68 (s, 3H), 4.10 (m, 1H), 4.26 (m, 2H), 5.10 (s, 2H), 7.34 (m, 5H).

Step C: 4-(N-Methoxycarbonyl-N-(ethyl)amino)piperidine

Using essentially the same procedure as in Procedure 1, Step D, 85 mg (0.27 mmol) of 1-benzyloxycarbonyl-4-(N-(methoxycarbonyl)-N-(ethyl)amino)piperidine from Step B was hydrogenated to afford 37 mg of the title compound.

Procedure 3

4-(Dimethylaminocarbonylamino)piperidine

Step A: 1-Benzyloxycarbonyl-4-(dimethylaminocarbonylamino)piperidine

To 0.83 g (3.2 mmol) of (1-benzyloxycarbonylpiperidin-4-yl)isocyanate from Procedure 1, Step A in 10 mL was added 16 mL (32 mmol) of 2 M dimethylamine in THF. The reaction was stirred under nitrogen at rt for 24 h and then poured into water containing 20 mL of 2 N hydrochloric acid and was extracted twice with ethyl acetate. The organic layers were each washed with a portion of brine, dried over sodium sulfate, combined and concentrated to give 0.95 g of the crude title compound which can be used directly in subsequent reactions.

$^1$H NMR (400 MHz, CDCl$_3$): δ 1.25 (m, 2H), 1.95 (br d, J=10, 2H), 2.86 (br s, 6H+2H), 3.79 (m, 1H), 4.0–4.25 (m, 3H), 5.09 (s, 2H), 7.35 (m, 5H).

Step B: 4-(Dimethylaminocarbonylamino)piperidine

Using essentially the same procedure as in Procedure 1, Step D, 1.4 g (4.6 mmol) of 1-benzyloxycarbonyl-4-(dimethylaminocarbonylamino)piperidine from Step A was hydrogenated to afford 690 mg of the title compound.

Procedure 4

4-(N-(Benzyloxycarbonyl)-N-(prop-1-yl)amino)piperidine

Step A: 4-Azido-1-t-butoxycarbonylpiperidine

To a solution of 45.3 g (172 mmol) of 4-bromo-1-t-butoxycarbonylpiperidine in 750 mL of DMF was added 22.3 g (343 mmol) of sodium azide and 2.5 g (17 mmol) of sodium iodide. The reaction was stirred at rt for 24 h and then at 60° C. for 4 h. The mixture was poured into water containing 20 mL of sodium bicarbonate and extracted twice with 1:1 ether:hexanes. The organic layers were each washed with a portion of water and brine, dried over sodium sulfate, combined and concentrated. The residue was purified by FC eluting with 5–10% ethyl acetate in hexanes to afford 39 g of title compound having a trace of elimination byproduct.

$^1$H NMR (400 MHz, CDCl$_3$): δ 1.43 (s, 9H), 1.52 (m, 2H), 1.85 (m, 2H), 3.07 (m, 2H), 3.55 (m, 1H), 3.78 (m, 2H).

Step B: 4-Amino-1-t-butoxycarbonylpiperidine

A solution of 4.05 g (17.9 mmol) of 4-azido-1-t-butoxycarbonylpiperidine from Step A in 50 mL of methanol was hydrogenated with 350 mg of 10% Pd/C under a hydrogen balloon for 16 h when the reaction was complete by TLC (10% ethyl acetate in hexanes). The catalyst was filtered off and the volatiles removed in vacuo to give 3.5 g of title compound which was used directly in subsequent reactions.

Step C: 4-Benzyloxycarbonylamino-1-t-butoxycarbonylpiperidine

To a solution of 1.2 g (6.0 mmol) 4-amino-1-t-butoxycarbonylpiperidine from Step B in 40 mL of methylene chloride was added 3.15 mL (18 mmol) of DIPEA and 1.03 mL (7.2 mmol) of benzyl chloroformate while cooled in an ice bath. After 0.5 h the reaction was quenched with aqueous sodium carbonate and extracted three times with methylene chloride. The organic layers were each washed with a portion of brine, dried over sodium sulfate, combined and concentrated. The residue was purified by FC eluting with 25% ethyl acetate in hexanes to afford 1.94 g of title compound.

$^1$H NMR (400 MHz, CDCl$_3$): δ 1.26 (m, 2H), 1.42 (s, 9H), 1.90 (br d, J=12, 2H), 2.90 (br t, 2H), 3.58 (m, 1H), 4.08 (m, 2H), 4.42 (br s, 1H), 5.09 (s, 2H), 7.33 (m, 5H).

Step D: 4-(N-(Benzyloxycarbonyl)-N-((prop-1-yl)amino)-1-t-butoxycarbonylpiperidine To 110 mg (0.32 mmol) 4-benzyloxycarbonylamino-1-t-butoxycarbonylpiperidine from Step C and 0.16 mL (1.6 mmol) of n-propyl iodide in 2 mL of DMF under nitrogen was added 26 mg (0.65 mmol) of 60% sodium hydride in mineral oil. The reaction was stirred at rt for 16 h and was then poured into water and extracted twice with ether. The organic layers were each washed with a portion of brine, dried over sodium sulfate, combined and concentrated. The residue was purified by FC eluting with 20% ethyl acetate in hexanes to afford 90 mg of title compound.

Step E: 4-(N-(Benzyloxycarbonyl)-N-(prop-1-yl)amino)piperidine hydrochloride salt To a solution of 2.4 mmol of HCl in 2 mL of methanol (prepared by the addition of 0.17 mL of acetyl chloride at 0° C. and stirring for 10 min) was added 90 mg of 4-(N-(benzyloxycarbonyl)-N-(prop-1-yl)amino)-1-t-butoxycarbonylpiperidine. The mixture was stirred at rt for 16 h at which time the reaction was complete by TLC (20% ethyl acetate in hexanes) and was evaporated to dryness in vacuo to afford 75 mg of the title compound as the hydrochloride salt.

Procedure 5

4-(N-(Benzyloxycarbonyl)-N-(allyl)amino)piperidine hydrochloride

Step A: 4-(N-(Benzyloxycarbonyl)-N-(allyl)amino)-1-(t-butoxycarbonyl)piperidine

Sodium hydride (47 mg of 60% oil dispersion, 1.2 mmol) was added to a solution of 4-(benzyloxycarbonylamino)-1-(t-butoxycarbonyl)piperidine (200 mg, 0.598 mmol) from Procedure 4, Step C and allyl bromide (0.251 mL, 351 mg, 2.9 mmol) in 2.0 mL of DMF, and the reaction was stirred overnight at rt. The reaction mixture was poured into 20 mL of water and extracted with 3×20 mL of ethyl ether. The combined organic layers were washed with 30 mL of brine, dried over sodium sulfate, and evaporated. The crude product was purified by flash column chromatography on silica gel, eluting with 20% ethyl acetate in hexane, to give 246 mg of the title compound as a viscous oil.

Mass spectrum (ESI): m/z=275 (M-99, 100%).

Step B: 4-(N-(Benzyloxycarbonyl)-N-(allyl)amino)piperidine hydrochloride

Acetyl chloride (0.467 mL, 516 mg, 6.57 mmol) was added to 2.0 mL of methanol at 0° C. and the mixture was stirred for 10 min to give a solution of HCl. 4-(N-(Benzyloxycarbonyl)allylamino)-1-(t-butoxycarbonyl)piperidine from Step A (123 mg, 0.33 mmol) was then added and the resulting solution was stirred for 1 h at 0° C. and 1 h at rt. The solution was evaporated to give the title compound as a crystalline solid in quantitative yield.

$^1$H NMR (400 MHz, CD$_3$OD): δ 7.39–7.28 (m, 5H), 5.84 (ddt, 1H, J=17, 10, 5 Hz), 5.21–5.10 (m, 4H), 4.10–3.98 (m, 1H), 3.90 (d, 2H, J=5 Hz), 3.43 (br d, 2H, J=13 Hz), 3.04 (br t, 2H, J=13 Hz), 2.18–2.02 (m, 2H), 1.93 (d, 2H; J=13 Hz).

Mass spectrum (CI): m/z=275 (M+1, 100%).

Procedure 6

4-(N-(4-Nitrobenzyloxycarbonyl)-N-(allyl)amino) piperidine hydrochloride

Step A: 1-(t-Butoxycarbonyl)-4-(N-(4-nitrobenzyloxycarbonyl)-N-(allyl)amino)piperidine Allylamine (0.45 mL, 0.34 g, 6.0 mmol), acetic acid (0.300 mL, 315 mg, 5.24 mmol), and 3 Å molecular sieves (2.00 g) were added to a solution of 1-(t-butoxycarbonyl)-4-piperidone (1.00 g, 5.01 mmol) in 14 mL of 1,2-dichloroethane. After stirring 0.5 h at rt, sodium triacetoxyborohydride (1.62 g, 7.6 mmol) was added in two portions 5 min apart. After an additional 3 h, the mixture was partitioned between 30 mL of ethyl acetate and 20 mL of saturated aqueous sodium bicarbonate. The aqueous layer was extracted with 30 mL of ethyl acetate and the organic layers were washed in succession with 20 mL of brine, combined, dried over sodium sulfate, and evaporated to give 1.20 g of crude 4-(allylamino)-1-(t-butoxycarbonyl)piperidine as a yellow syrup.

A portion of the crude 4-(allylamino)-1-(t-butoxycarbonyl)piperidine (400 mg, 1.66 mmol) was dissolved in 10 mL of dichloromethane and treated with N,N-diisopropylethylamine (0.700 mL, 519 mg, 4.0 mmol) and 4-nitrobenzyl chloroformate (392 mg, 1.82 mmol). After stirring 3 h at rt, the mixture was diluted with 30 mL of ethyl acetate and washed with 15 mL each of 2 N aqueous HCl, saturated aqueous sodium bicarbonate, and brine. The organic layer was dried over sodium sulfate, and evaporated. The residue was purified by flash column chromatography on silica gel, eluting with 30% ethyl acetate in hexane, to give 572 mg of the title compound as a colorless syrup.

$^1$H NMR (400 MHz, CDCl$_3$): δ 8.22 (d, 2H, J=8 Hz), 7.50 (d, 2H, J=8 Hz), 5.80 (ddt, 1H, J=17, 10, 5 Hz), 5.23 (s, 2H), 5.18–5.09 (m, 2H), 4.27–4.08 (m, 3H), 3.89–3.79 (m, 2H), 2.79–2.66 (m, 2H), 1.74–1.52 (m, 4H), 1.46 (s, 9H).

Mass spectrum (ESI): m/z=420 (M+1, 27%), 437 (M+1+NH$_3$, 100%).

Step B: 4-(N-(4-Nitrobenzyloxycarbonyl)-N-(allyl)amino)piperidine hydrochloride

The title compound was prepared according to the procedure of Procedure 4, Step E, replacing 4-(N-(benzyloxycarbonyl)-N-(ethyl)amino)-1-(t-butoxycarbonyl)piperidine with 1-(t-butoxycarbonyl)-4-(N-(4-nitrobenzyloxycarbonyl)-N-(allyl)amino)piperidine. $^1$H NMR (400 MHz, CD$_3$OD): δ 8.24 (d, 2H, J=8 Hz), 7.60 (d, 2H, J=8 Hz), 5.87 (ddt, 1H, J=17, 10, 5 Hz), 5.27 (s, 2H), 5.23–5.13 (m, 2H), 4.14–3.94 (m, 1H), 3.94 (d, 2H, J=5Hz), 3.45 (d, 2H, J=13 Hz), 3.06 (t, 2H, J=13 Hz), 2.20–2.03 (m, 2H), 2.02–1.90 (m, 2H).

Mass spectrum (ESI): m/z=320 (M+1, 93%).

Procedure 7

The following substituted piperidines were prepared following the procedures described in Procedure 2 but substituting the appropriate alcohol and/or alkylating agent in Step A and B.

4-(N-(Methoxycarbonyl)-N-(hex-1-yl)amino)piperidine
4-(N-(Methoxycarbonyl)-N-(3,5,5-trimethylhex-1-yl)amino)piperidine
4-(N-(Ethoxycarbonyl)-N-(cyclohexylmethyl)amino)piperidine

Procedure 8

The following substituted piperidines were prepared following the procedures described in Procedure 4 but substituting the appropriate alkyl bromide or iodide for n-propyl iodide in Step D.

4-(N-(Benzyloxycarbonyl)-N-(ethyl)amino)piperidine hydrochloride
4-(N-(Benzyloxycarbonyl)-N-(2-methylprop-1-yl)amino)piperidine hydrochloride
4-(N-(Benzyloxycarbonyl)-N-(ethyl)amino)piperidine hydrochloride
4-(N-(Benzyloxycarbonyl)-N-(prop-2-yl)amino)piperidine hydrochloride
4-(N-(Benzyloxycarbonyl)-N-(cyclopropylmethyl)amino)piperidine hydrochloride
4-(N-(Benzyloxycarbonyl)-N-(1-methylprop-1-yl)amino)piperidine hydrochloride

Procedure 9

The following substituted piperidines were prepared following the procedures described in Procedure 6 but substituting the appropriate alkyl amine and/or acylating agent in Step A.

4-(N-(3-Nitrobenzyloxycarbonyl)-N-(propargyl)amino)piperidine hydrochloride
4-(N-(2-Nitrobenzyloxycarbonyl)-N-(propargyl)amino)piperidine hydrochloride
4-(N-(4-Nitrobenzylaminocarbonyl)-N-(allyl)amino)piperidine hydrochloride
4-(N-(3-Nitrobenzylaminocarbonyl)-N-(allyl)amino)piperidine hydrochloride
4-(N-(2-Nitrobenzylaminocarbonyl)-N-(allyl)amino)piperidine hydrochloride
4-(N-(4-Nitrobenzylcarbonyl)-N-(allyl)amino)piperidine hydrochloride
4-(N-(3-Nitrobenzylcarbonyl)-N-(allyl)amino)piperidine hydrochloride
4-(N-(4-Nitrobenzyloxycarbonyl)-N-(propargyl)amino)piperidine hydrochloride
4-(N-(Benzyloxycarbonyl)-N-(prop-1-yl)amino)piperidine hydrochloride
4-(N-(Phenylcarbonyl)-N-(prop-1-yl)amino)piperidine hydrochloride
4-(N-(Benzylcarbonyl)-N-(prop-1-yl)amino)piperidine hydrochloride
4-(N-(Cyclohexyloxycarbonyl)-N-(prop-1-yl)amino)piperidine hydrochloride
4-(N-(2-Phenyleth-1-yloxycarbonyl)-N-(prop-1-yl)amino)piperidine hydrochloride
4-(N-(3-Phenylprop-1-yloxycarbonyl)-N-(prop-1-yl)amino)piperidine hydrochloride
4-(N-(4-Phenylbenzyloxycarbonyl)-N-(prop-1-yl)amino)piperidine hydrochloride
4-(N-(2-Naphthylmethyloxycarbonyl)-N-(prop-1-yl)amino)piperidine hydrochloride
4-(N-(1-Naphthylmethyloxycarbonyl)-N-(prop-1-yl)amino)piperidine hydrochloride
4-(N-(4-Methylbenzyloxycarbonyl)-N-(prop-1-yl)amino)piperidine hydrochloride
4-(N-(4-Trifluoromethylbenzyloxycarbonyl)-N-(prop-1-yl)amino)piperidine hydrochloride
4-(N-(Butyloxycarbonyl)-N-(prop-1-yl)amino)piperidine hydrochloride
4-(N-(Benzylaminocarbonyl)-N-(prop-1-yl)amino)piperidine hydrochloride

Procedure 10

The following set of 70 substituted piperidines were prepared as their di-TFA salts following the procedures described in Procedure 6 but substituting the appropriate alkyl amine and acylating agent in Step A and using TFA at rt in Step B.

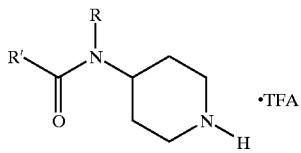

R=
Methyl
Ethyl
n-Propyl
n-Butyl
Allyl
Cyclopropylmethyl
2-Methylcycloprop-1-yl
R'=
Benzyloxy
4-Nitrobenzyloxy
2-Phenyleth-1-yloxy
2-(4-Nitrophenyl)eth-1-yloxy
Benzylamino
4-Nitrobenzylamino
2-Phenyleth-1-yl
2-(4-Nitrophenyl)eth-1-yl
Phenoxymethyl
4-Nitrophenoxymethyl

EXAMPLE 1

1-(SR)-Benzyloxy-3-(SR)-((4-(N-(benzyloxycarbonyl)-N-(ethyl)amino)piperidin-1-yl)methyl)-4-(SR)-phenylcyclopentane hydrochloride salt Step A: (+−)-cis- and trans-4-Oxo-2-phenylcyclopentanoic acid A mixture of the title compounds (11.1 g) was prepared as described by A. W. von Frahm, *Liebigs Ann. Chem.*, 1969, 728, 21 from methyl trans-cinnamate (16.2 g, 0.1 mol) and trimethyl 1,1,2-ethane tricarboxylate (20.4 g, 0.1 mol). After refluxing the intermediate triester (17.7 g) in acetic acid/aq HCl for 3 days, the crude mixture of the cis and trans products was used directly in the next step without separation of the isomers.

Step B: Methyl(+−)-cis- and trans-4-oxo-2-phenylcyclopentanoate

To the crude acid products from Step A (6.6 g, 32 mmol) in methanol (60 mL) and methylene chloride (180 mL) was added dropwise 2M trimethylsilyldiazomethane in hexanes (18 mL) after which the yellow color persisted. After an additional 20 min, the excess trimethylsilyldiazomethane was quenched with acetic acid and the reaction was concentrated in vacuo. The crude mixture was purified by FC using a gradient of 5 to 15% ethyl acetate in hexanes to give the higher $R_f$ trans product (2.05 g) and then the lower cis product (3.71 g). The assignments were based on the NMR of each which were the same as reported in the literature.

Step C: Methyl 1-(SR)-4-(RS)-hydroxy-2-(SR)-phenylcyclopentanoate (Higher isomer) and methyl 1-(SR)-4-(SR)-hydroxy-2-(SR)-phenylcyclopentanoate (Lower isomer)

To a solution of methyl(+−)-trans-4-oxo-2-phenylcyclopentanoate (1.3 g, 6.0 mmol) from Step B in methanol (50 mL) was added portionwise over 5 min sodium borohydride (0.23 g, 6.0 mmol). After 1 h, the reaction was complete by TLC and was quenched by addition to dilute aq. HCl. This was extracted twice with ether and the organic layers were each washed with brine, dried over sodium sulfate and concentrated in vacuo. The residue was purified by FC using a gradient of 20 to 30% ethyl acetate in hexanes to give pure higher $R_f$ title product (0.3 g), mixed fractions (0.41 g), and then clean lower title product (0.6 g).

Higher isomer: NMR (CDCl$_3$) δ: 1.6 (br s, 1H), 1.79 (dddd, J=1.3, 4.3, 9.1, 13.7 Hz, 1H), 2.0–2.2 (m, 2H), 2.55 (ddd, J=6.0, 9.3, 13.7 Hz, 1H), 3.15 (br q, J=9 Hz, 1H), 3.38 (q, J=9 Hz, 1H), 3.58 (s, 3H), 4.50 (m, 1H), 7.1–7.3 (m, 5H).

Lower isomer: NMR (CDCl$_3$) δ: 1.58 (br s, 1H), 1.92 (ddd, J=5.0, 11.3, 13.5 Hz, 1H), 2.04 (ddt, J=2.2, 5.3, 15 Hz, 1H), 2.23 (ddt, J=1.7, 7.5, 13.5 Hz, 1H), 2.39 (ddd, J=5.2, 10, 14.4 Hz, 1H), 2.94 (ddd, J=5.3, 8.3, 10 Hz, 1H), 3.65 (s, 3H), 3.67 (m, 1H), 4.49 (m, 1H), 7.15–7.35 (m, 5H).

Step D: Methyl 1-(SR)-4-(SR)-benzyloxy-2-(SR)-phenylcyclopentanoate

To a solution of methyl 1-(SR)-4-(SR)-hydroxy-2-(SR)-phenylcyclopentanoate (Lower isomer from Step C) (550 mg, 2.5 mmol) and benzyl bromide (2.2 g, 12.5 mmol) in DMF (5 mL) was added portionwise sodium hydride (60% in mineral oil) (250 mg, 6.25 mmol) over 20 min. After 30 min, the reaction was quenched into aq. HCl and was extracted twice with ether. The organic layers were each washed with brine, dried over sodium sulfate and concentrated in vacuo. The residue was purified by FC using a gradient of 5 to 10% ethyl acetate in hexanes to give the title product (0.375 g). Elution with 20 to 50% ethyl acetate in hexanes afforded recovered starting material (120 mg).

NMR (CDCl$_3$) δ: 1.90 (ddd, 1H), 2.20 (dddd, 1H), 2.31 (ddt, 1H), 2.43 (ddd, 1H), 2.85 (q, 1H), 3.60 (s, 3H), 3.69 (dt, 1H), 4.17 (m, 1H), 4.50 (Abq, 2H), 7.15–7.4 (m, 10H).

Step E: 1-(SR)-Benzyloxy-3-(SR)-hydroxymethyl-4-(SR)-phenylcyclopentane

To a solution of methyl 1-(SR)-4-(SR)-benzyloxy-2-(SR)-phenylcyclopentanoate (370 mg, 1.2 mmol) (from Step D) in THF (10 mL) under nitrogen was added lithium borohydride (55 mg, 2.4 mmol). A mixture was stirred at RT for 16 h and then at 50° C. for 4 h when TLC indicated that the reaction was complete. The reaction was quenched into dilute aq. HCl and was extracted twice with ether. The organic layers were each washed with brine, dried over sodium sulfate and concentrated in vacuo. The residue was purified by FC using a gradient of 20 to 40% ethyl acetate in hexanes to give the title product (0.34 g).

NMR (CDCl$_3$) δ: 1.7–1.9 (m, 2H+br OH), 2.2–2.4 (m, 3H), 3.16 (ddd, 1H), 3.62 (dABq, 2H), 4.17 (m, 1H), 4.51 (ABq, 2H), 7.15–7.45 (m, 10H).

Step F: 1-(SR)-4-(SR)-Benzyloxy-2-(SR)-phenylcyclopentanecarboxaldehyde

To a solution of oxalyl chloride (0.27 mL, 3.0 mmol) in methylene chloride (5 mL) at −70° C. was added dropwise DMSO (0.47 mL, 6.0 mmol). After 15 min, a solution of 1-(SR)-benzyloxy-3-(SR)-hydroxymethyl-4-(SR)-phenylcyclopentane (340 mg, 1.2 mmol) (from Step E) in methylene chloride (5 mL) was added. The reaction was stirred at −70° C. for 2 h and then DIPEA (2.2 mL, 12 mmol) was added. After a further 10 min, the mixture was allowed to warm to RT for 1 h and was then diluted with methylene chloride and poured into dilute aq. HCl and the layers were separated. The aq. layer was reextracted with a second and the organic layers were each washed with brine, dried over sodium sulfate, combined and concentrated in vacuo. The residue was purified by FC using a gradient of 10 to 15% ethyl acetate in hexanes to give the title product (0.335 g) as an oil.

NMR (CDCl$_3$) δ: 1.89 (ddd, 1H), 2.2–2.35 (m, 2H), 2.38 (ddt, 1H), 2.83 (m, 1H), 3.66 (ddd, 1H), 4.20 (m, 1H), 4.48 (Abq, 2H), 7.15–7.4 (m, 10H), 9.67 (d, 1H).

Step G: 1-(SR)-Benzyloxy-3-(SR)-((4-(N-(benzyloxycarbonyl)-N-(ethyl)amino)piperidin-1-yl)methyl)-4-(SR)-phenylcyclopentane hydrochloride salt To a solution of 1-(SR)-4-(SR)-benzyloxy-2-(SR)-phenylcyclopentanecarboxaldehyde (15 mg, 0.054 mmol) (from Step F) in 1,2-dichloroethane (1 mL) was added 4-(N-(benzyloxycarbonyl)-N-(ethyl)amino)piperidine hydrochloride (20 mg, 0.067 mmol) and DIPEA (0.012 mL, 0.067 mmol). After 10 min, sodium triacetoxyborohydride (23 mg, 0.11 mmol) was added and the reaction was stirred at RT for 16 h. The reaction was quenched with aq. sodium carbonate and extracted 3 times with methylene chloride. The organic layers were each washed with brine, dried over sodium sulfate, combined and concentrated in vacuo. The residue was purified by Prep TLC eluting with 2% methanol in methylene chloride to give the title product. The hydrochloride salt was prepared by taking up the free amine in ether, addition of excess 1M hydrogen chloride in ether and evaporation to afford the title compound (30 mg) as a white solid.

NMR (CDCl$_3$) (free amine) δ: 1.07 (br t, 3H), 1.4–1.7 (3 m, 6H), 1.7–1.9 (m,3H), 2.1–2.4 (m, 4H), 2.7 (m, 1H), 2.83 (m, 1H), 2.90 (m, 1H), 3.1–3.25 (m, 2H), 3.6–4.0 (2 m, 1H), 4.14 (m, 1H), 4.50 (Abq, 2H), 5.11 (Abq, 2H), 7.16 (m, 1H), 7.2–7.4 (m, 9H).

MS (NH$_3$/CI): m/z 527 (M+1), 393 (100%, M+1-134).

EXAMPLE 2

1-(SR)-Benzyloxy-3-(SR)-((4-(N-(benzyloxycarbonyl)(N-2-methylpropyl)amino)piperidin-1-yl)methyl)-4-(SR)-phenylcyclopentane hydrochloride salt Using essentially the same procedure as in Example 1, Step G and aldehyde from Step F (derived from the Lower R$_f$ alcohol intermediate), but using 4-(N-(benzyloxycarbonyl)-N-(2-methylpropyl)amino)piperidine hydrochloride, the title compound was prepared.

MS (NH$_3$/CI): m/z 555 (M+1), 421 (100%, M+1-134).

EXAMPLE 3

1-(SR)-Benzyloxy-3-(SR)-((4-(N-(benzyloxycarbonyl)-N-(propyl)amino)piperidin-1-yl)methyl)-4-(SR)-phenylcyclopentane hydrochloride salt Using essentially the same procedure as in Example 1, Step G and aldehyde from Step F (derived from the Lower R$_f$ alcohol intermediate), but using 4-(N-(benzyloxycarbonyl)-N-(propyl)amino)piperidine hydrochloride, the title compound was prepared.

MS (NH$_3$/CI): m/z 541 (M+1), 407 (100%, M+1-134).

EXAMPLE 4

1-(RS)-Benzyloxy-3-(SR)-((4-(N-(benzyloxycarbonyl)-N-(ethyl)amino)piperidin-1-yl)methyl)-4-(SR)-phenylcyclopentane hydrochloride salt Using essentially the same procedures as in Example 1, Step D–G except using the Higher R$_f$ alcohol intermediate from Example 1, Step C, the title compound was prepared.

Step D: Methyl 1-(SR)-4-(RS)-benzyloxy-2-(SR)-phenylcyclopentanoate

NMR (CDCl$_3$) δ: 1.94 (dddd, 1H), 2.09 (ddd, 1H), 2.28 (dddd, 1H), 2.53 (ddd, 1H), 3.09 (dt, 1H), 3.34 (q, 1H), 3.58 (s, 1H), 4.17 (m, 1H), 4.52 (s, 2H), 7.15–7.22 (m, 1H), 7.25–7.35 (2 m, 9H).

Step E: 1-(RS)-Benzyloxy-3-(SR)-hydroxymethyl-4-(SR)-phenylcyclopentane

NMR (CDCl$_3$) δ: 1.5 (br s, 1H), 1.75 (ddd, 1H), 1.93 (dddd, 1H), 2.24 (br ddd, 1H), 2.42 (m, 1H), 2.49 (ddd, 1H), 3.55 (dABq, 2H), 4.10 (m, 1H), 4.52 (s, 2H), 7.15–7.22 (m, 1H), 7.25–7.35 (2 m, 9H).

Step G: 1-(RS)-Benzyloxy-3-(SR)-((4-(N-(benzyloxycarbonyl)-N-(ethyl)amino)piperidin-1-yl)methyl)-4-(SR)-phenylcyclopentane hydrochloride salt NMR (CDCl$_3$) (free amine) δ: 1.07 (br t, 3H), 1.4–1.7 (m, 6H), 1.7–1.9 (m, 3H), 2.1–2.3 (br m, 2H), 2.3–2.5 (m, 2H), 2.55 (q, 1H), 2.6–2.75 (m, 1H), 2.75–2.9 (m, 1H), 3.1–3.25 (m, 2H), 3.6–4.0 (2 m, 1H), 4.08 (m, 1H), 4.51 (Abq, 2H), 5.10 (s, 2H), 7.16 (m, 1H), 7.2–7.4 (m, 9H).

MS (NH$_3$/CI): m/z 527 (M+1), 393 (100%, M +1-134).

EXAMPLE 5

1-(RS)-Benzyloxy-3-(SR)-((4-(N-(benzyloxycarbonyl)-N-(2-methylpropyl)amino)piperidin-1-yl)methyl)-4-(SR)-phenylcyclopentane hydrochloride salt Using essentially the same procedure as in Example 1, Step G and aldehyde derived from the higher R$_f$ alcohol intermediate from Example 1, Step C, but using 4-(N-(benzyloxycarbonyl)-N-(2-methylpropyl)amino)piperidine hydrochloride, the title compound was prepared.

MS (NH$_3$/CI): m/z 555 (M+1), 421 (100%, M+1-134).

EXAMPLE 6

1-(SR)-((RS)-(1-Phenyl-1-ethoxy))-3-(SR)-((4-(N-(benzyloxycarbonyl)-N-(ethyl)amino)piperidin-1-yl)methyl)-4-(SR)-phenylcyclopentane hydrochloride salt and 1-(SR)-((SR)-(1-phenyl-1-ethoxy))-3-(SR)-((4-(N-(benzyloxycarbonyl)-N-(ethyl)amino)piperidin-1-yl)methyl)-4-(SR)-phenylcyclopentane hydrochloride salt (The absolute assignments were not made.)

Step A: (O-((R)-1-phenyl-1-ethyl))trichloroacetimidate

Sodium hydride (60% in mineral oil, 50 mg, 1.2 mmol) was suspended in dry ether (10 mL) under nitrogen and after stirring for 10 min, (R)-1-phenylethanol (1.5 g, 12.3 mmol) was added. The suspension was stirred for 10 min and then warmed to reflux for 15 min, however the suspension did not clarify. Trichloroacetonitrile (1.4 mL, 13.5 mmol) was added directly to the above mixture (rather than usual inverse addition) at which time the reaction was clear. After 3 h at RT, TLC (20% ethyl acetate in hexanes) indicated still mostly starting alcohol. Additional sodium hydride (50 mg) was added and the mixture was heated to 40° C. for 3 h and then stirred at RT for 3 days. Even though TLC indicated a mixture of product and starting material, the reaction was concentrated and the residue was purified by FC (10% ethyl acetate in hexanes) to afford the title product (1.9 g) as an oil.

NMR (CDCl$_3$) δ: 1.66 (d, 3H), 5.98 (q, 1H), 7.2–7.4 (m, 5H), 8.30 (s, 1H).

Step B: Methyl 1-(SR)-4-(SR)-((RS and SR)-1-phenyl-1-ethoxy)-2-(SR)-phenylcyclopentanoate To a solution of methyl 1-(SR)-4-(SR)-hydroxy-2-(SR)-phenylcyclopentanoate (lower isomer from Example 1, Step C) (200 mg, 0.91 mmol) in methylene chloride (2 mL) at 0° C. under nitrogen was added (O-((R)-1-phenyl-1-ethyl)) trichloroacetimidate (485 mg, 1.82 mmol) (Step A) in cyclohexane (2 mL) followed by a catalytic amount of TfOH in methylene chloride. The reaction was stirred at 0° C. for 1 h and was then diluted with methylene chloride and quenched into water. The layers were separated and the aq. layer was extracted with methylene chloride. The organic layers were each washed with brine, dried over sodium sulfate, combined and concentrated in vacuo. The residue was purified by FC using a gradient of 0 to 5% ethyl acetate in hexanes to give the title product (0.12 g) as an oil. There was no evidence for separation of isomers. NMR indicated a 1:1 mixture.

NMR (CDCl$_3$) δ: 1.43 (2 d, 3H), 1.75–1.9 (m, 1H), 1.95–2.1 and 2.15–2.25 (2 m, 1H), 2.25–2.4 (m, 2H), 2.7–2.9 (2 app. q, 1H), 3.59 and 3.64 (2 s, 3H), 3.6–3.8 (m, 1H), 3.98 (m, 1H), 4,49 (app. p, 1H), 7.15–7.4 (m, 10H).

Step C: 1-((SR)-((RS)-1-Phenyl-1-ethoxy))-3-(SR)-hydroxymethyl-4-(SR)-phenylcyclopentane and 1-((SR)-((SR)-1-phenyl-1-ethoxy))-3-(SR)-hydroxymethyl-4-(SR)-phenylcyclopentane (The absolute assignments were not made.)

Using essentially the same procedure as Example 1, Step E, the 1:1 mixture of methyl 1-(SR)-4-(SR)-((RS and SR)-1-phenyl-1-ethoxy)-2-(SR)-phenylcyclopentanoate (120 mg, 0.37 mmol) from Step B was converted to the title compounds which were separated by FC (5 to 10% ethyl acetate in hexanes) to give 2 racemic products (60 mg each).

Higher R$_f$: NMR (CDCl$_3$) δ: 1.44 (d, 3H), 1.6–1.8 (m, 2H), 2.1–2.25 (m, 2H), 2.25–2.4 (m, 1H), 3.15–3.3 (m, 1H), 3.55–3.7 (br dABq, 2H), 3.96 (m, 1H), 5.53 (q, 1H), 7.1–7.4 (m, 10H).

Lower R$_f$: NMR (CDCl$_3$) δ: 1.42 (d, 3H), 1.6–1.85 (m, 2H), 2.05–2.15 (m, 1H), 2.15–2.3 (m, 2H), 3.1–3.2 (dt, 1H), 3.62 (dABq, 2H), 3.99 (m, 1H), 4.51 (q, 1H), 7.1–7.4 (M, 10H).

Step D: 1-(SR)-4-((SR)-((RS)-1-Phenyl-1-ethoxy))-4-(SR)-phenylcyclopentane carboxaldehyde and 1-(SR)-4-((SR)-((SR)-1-phenyl-1-ethoxy))-4-(SR)-phenylcyclopentane carboxaldehyde Using essentially the same procedure as Example 1, Step F, each of the 1-((SR)-((RS)-1-phenyl-1-ethoxy))-3-(SR)-hydroxymethyl-4-(SR)-phenylcyclopentane and 1-((SR)-((SR)-1-phenyl-1-ethoxy))-3-(SR)-hydroxymethyl-4-(SR)-phenylcyclopentane isomers (60 mg, 0.20 mmol each) from Step C were converted to their respective title compounds which were purified by FC (10% ethyl acetate in hexanes) to give the respective higher and lower racemic aldehyde products (25 and 35 mg).

Step E: 1-(SR)-((RS)-(1-Phenyl-1-ethoxy))-3-(SR)-((4-(N-(benzyloxycarbonyl)-N-(ethyl)amino)piperidin-1-yl)methyl)-4-(SR)-phenylcyclopentane hydrochloride salt and 1-(SR)-((SR)-(1-phenyl-1-ethoxy))-3-(SR)-((4-(N-(benzyloxycarbonyl)-N-(ethyl)amino)piperidin-1-yl)methyl)-4-(SR)-phenylcyclopentane hydrochloride salt Using essentially the same procedure as Example 1, Step G, each of the 1-(SR)-4-((SR)-((RS)-1-phenyl-1-ethoxy))-4-(SR)-phenylcyclopentane carboxaldehyde and 1-(SR)-4-((SR)-((SR)-1-phenyl-1-ethoxy))-4-(SR)-phenylcyclopentane carboxaldehyde isomers (11 mg, 0.037 mmol) from Step D were reacted with 4-(N-(benzyloxycarbonyl)-N-(ethyl)amino)piperidine to afford the title products (21 and 15 mg).

Higher R$_f$: MS (NH$_3$/CI): m/z 541 (M+1).

Lower R$_f$: MS (NH$_3$/CI): m/z 541 (M+1).

EXAMPLE 7

1-(SR)-((RS)-(1-Phenyl-1-ethoxy))-3-(SR)-((4-(N-(benzyloxycarbonyl)-N-(propyl)amino)piperidin-1-yl)methyl)-4-(SR)-phenylcyclopentane hydrochloride salt and 1-(SR)-((SR)-(1-phenyl-1-ethoxy))-3-(SR)-((4-(N-(benzyloxycarbonyl)-N-(propyl)amino)piperidin-1-yl)methyl)-4-(SR)-phenylcyclopentane hydrochloride salt (The absolute assignments were not made.)

Using essentially the same procedure as Example 1, Step G, each of the 1-(SR)-4-((SR)-((RS)-1-phenyl-1-ethoxy))-4-(SR)-phenylcyclopentane carboxaldehyde and 1-(SR)-4-((SR)-((SR)-1-phenyl-1-ethoxy))-4-(SR)-phenylcyclopentane carboxaldehyde isomers (11 mg, 0.037 mmol) from Example 6, Step D were also reacted with 4-(N-(benzyloxycarbonyl)-N-(propyl)amino)piperidine to afford the title products (26 and 17 mg).

Higher R$_f$: MS (NH$_3$/CI): m/z 555 (M+1).

Lower R$_f$: MS (NH$_3$/CI): m/z 555 (M+1).

EXAMPLE 8

1-(SR)-((RS)-(1-Phenyl-1-ethoxy) )-3-(SR)-((4-(N-(benzyloxycarbonyl)-N-(2-methylpropyl)amino) piperidin-1-yl)methyl)-4-(SR)-phenylcyclopentane hydrochloride salt and 1-(SR)-((SR)-(1-phenyl-1-ethoxy))-3-(SR)-((4-(N-(benzyloxycarbonyl)-N-(2-methylpropyl)amino)piperidin-1-yl)methyl)-4-(SR)-phenylcyclopentane hydrochloride salt (The absolute assignments were not made.)

Using essentially the same procedure as Example 1, Step G, each of the 1-(SR)-4-((SR)-((RS)-1-phenyl-1-ethoxy))-4-(SR)-phenylcyclopentane carboxaldehyde and 1-(SR)-4-((SR)-((SR)-1-phenyl-1-ethoxy))-4-(SR)-phenylcyclopentane carboxaldehyde isomers (12 mg, 0.041 mmol) from Example 6, Step D were also reacted with 4-(N-(benzyloxycarbonyl)-N-(2-methylpropyl)amino) piperidine to afford the title products (2.2 and 8 mg).

Higher R$_f$: MS (NH$_3$/CI): m/z 569 (M+1).

Lower R$_f$: MS (NH$_3$/CI): m/z 569 (M+1).

EXAMPLE 9

1-(RS)-((RS)-(1-Phenyl-1-ethoxy))-3-(SR)-((4-(N-(benzyloxycarbonyl)-N-(propyl)amino)piperidin-1-yl)methyl)-4-(SR)-phenylcyclopentane hydrochloride salt and 1-(RS)-((SR)-(1-phenyl-1-ethoxy))-3-(SR)-((4-(N-(benzyloxycarbonyl)-N-(propyl)amino)piperidin-1-yl)methyl)-4-(SR)-phenylcyclopentane hydrochloride salt (The isomers were not separable and the absolute assignments were not made.)

Using essentially the same procedure as Example 1, Step G, a mixture of 1-(SR)-4-((RS)-((RS)-1-phenyl-1-ethoxy))-4-(SR)-phenylcyclopentane carboxaldehyde and 1-(SR)-4-((RS)-((SR)-1-phenyl-1-ethoxy))-4-(SR)-phenylcyclopentane carboxaldehyde isomers (15 mg, 0.051 mmol) (prepared as in Example 6, Step B–D but starting with the higher alcohol isomer from Example 1, Step C) were reacted with 4-(N-(benzyloxycarbonyl)-N-(propyl) amino)piperidine to afford a mixture of the title products (20 mg).

MS (NH$_3$/CI): m/z 565 (M+1).

EXAMPLE 10

1-(RS)-((RS)-(1-Phenyl-1-ethoxy))-3-(SR)-((4-(N-(benzyloxycarbonyl)-N-(2-methylpropyl)amino) piperidin-1-yl)methyl)-4-(SR)-phenylcyclopentane hydrochloride salt and 1-(RS)-((SR)-(1-phenyl-1-ethoxy))-3-(SR)-((4-(N-(benzyloxycarbonyl)-N-(2-methylpropyl)amino)piperidin-1-yl)methyl)-4-(SR)-phenylcyclopentane hydrochloride salt (The isomers were not separable and the absolute assignments were not made.)

Using essentially the same procedure as Example 1, Step G, a mixture of 1-(SR)-4-((RS)-((RS)-1-phenyl-1-ethoxy))-4-(SR)-phenylcyclopentane carboxaldehyde and 1-(SR)-4-((RS)-((SR)-1-phenyl-1-ethoxy))-4-(SR)-phenylcyclopentane carboxaldehyde isomers (15 mg, 0.051 mmol) (prepared as in Example 6, Step B–D but starting with the higher alcohol isomer from Example 1, Step C) were reacted with 4-(N-(benzyloxycarbonyl)-N-(2-methylpropyl)amino)piperidine to afford a mixture of the title products (22 mg).

MS (NH$_3$/CI): m/z 569 (M+1).

EXAMPLE 11

1-(RS)-(N-(Methyl)-N-(phenylsulfonyl)amino)-3-(SR)-((4-(N-(benzyloxycarbonyl)-N-(ethyl)amino) piperidin-1-yl)methyl)-4-(SR)-phenylcyclopentane hydrochloride salt Step A: Methyl 1-(SR)-4-((RS and SR)-(N-(methyl)amino)-2-(SR)-phenylcyclopentanoate To a solution of methyl(+−)-trans-4-oxo-2-phenylcyclopentanoate (0.30 g, 1.4 mmol) from Example 1, Step B in 1,2-dichloroethane (5 mL) was added methylamine hydrochloride (185 mg, 2.8 mmol) and DIPEA (0.50 mL, 2.8 mmol). After 10 min, sodium triacetoxyborohydride (600 mg, 2.8 mmol) was added. The reaction was stirred at RT for 2 h before being quenched with dilute aq. sodium carbonate solution and extracted twice with methylene chloride. The organic layers were washed with brine, dried over sodium sulfate, combined and concentrated. The crude solution of the title C-4 isomers was used directly in subsequent reactions.

Step B: Methyl 1-(SR)-4-(RS and SR)-(N-(methyl)-N-(phenylsulfonyl)amino)-2-(SR)-phenylcyclopentanoate To ½ of the crude methyl 1-(SR)-4-((RS and SR)-(N-(methyl))amino)-2-(SR)-phenylcyclopentanoate mixture (assumed 0.7 mmol) from Step A in methylene chloride (3 mL) was added benzenesulfonyl chloride (250 mg, 1.4 mmol) and DIPEA (0.365 mL, 2.2 mmol). The reaction was stirred at RT for 16 h and was then quenched with dilute aq. HCl and extracted twice with methylene chloride. The organic layers were washed with brine, dried over sodium sulfate, combined and concentrated. The residue was purified by FC (20–40% ethyl acetate in hexanes) to afford a 1:2 mixture of the title isomers (215 mg).

NMR (CDCl$_3$) δ: 1.7–2.2 (m, 4H), 2.7–2.9 (m, 1H), 2.78 and 2.82 (2 s (1:2), 3H), 3.24 and 3.32 (ddd and q (1:2), 1H), 3.54 and 3.56 (2 s (2:1), 3H), 4.63 and 4.74 (2 m (1:2), 1H), 7.1–7.3 (m, 5H), 7.45–7.6 (m, 3H), 7.79 (2 d, 2H).

MS (NH$_3$/ESI): m/z 374 (M+1), 391 (100%, M+1+17).

Step C: 1-(RS)-(N-(Methyl)-N-(phenylsulfonyl)amino)-3-(SR)-(hydroxymethyl)-4-(SR)-phenylcyclopentane (Higher R$_f$ isomer) and 1-(SR)-(N-(methyl)-N-(phenylsulfonyl) amino)-3-(SR)-(hydroxymethyl)-4-(SR)-phenylcyclopentane (Lower R$_f$ isomer)

To a solution of methyl 1-(SR)-4-(RS and SR)-(N-(methyl)-N-(phenylsulfonyl)amino)-2-(SR)-phenylcyclopentanoate (200 mg, 0.54 mmol) from Step B in THF (10 mL) under nitrogen was added 2M lithium borohydride in THF (0.27 mL, 0.54 mmol). The reaction was stirred at RT for 16 h and then an additional aliquot of 2M lithium borohydride was added. After 4 h at 60° C., TLC indicated that the reaction was complete. The reaction was quenched into dilute aq. HCl and was extracted twice with ether. The organic layers were each washed with brine, dried over sodium sulfate and concentrated in vacuo. The residue was purified by FC using a gradient of 25 to 40% ethyl acetate in hexanes to give separation of the title products (66 mg and 120 mg).

Higher: NMR (CDCl$_3$) δ: 1.44 (br s, 1H), 1.65–1.85 (m, 3H), 1.9–2.0 (m, 1H), 2.1–2.2 (m, 1H), 2.66 (ddd, 1H), 2.81 (s, 3H), 3.46 (dABq, 2H), 4.53 (m, 1H), 7.1–7.2 (m, 3H), 7.2–7.3 (m, 2H), 7.45–7.55 (m, 3H), 7.80 (m, 2H).

Lower: NMR (CDCl$_3$) δ: 1.38 (br s, 1H), 1.55 (q, 1H), 1.8–1.9 (m, 2H), 1.9–2.1 (m, 2H), 2.85–2.95 (s and m, 4H), 3.48 (d Abq, 2H), 4.71 (m, 1H), 7.1–7.2 (m, 3H), 7.2–7.3 (m, 2H), 7.45–7.55 (m, 3H), 7.79 (m, 2H).

Step D: 1-(RS)-(N-(Methyl)-N-(phenylsulfonyl)amino)-3-(SR)-(formyl)-4-(SR)-phenylcyclopentane (Higher R$_f$ isomer)

To a solution of oxalyl chloride (0.045 mL, 0.50 mmol) in methylene chloride (2 mL) at −70° C. was added dropwise DMSO (0.045 mL, 1.0 mmol). After 15 min, a solution of 1-(RS)-(N-(methyl)-N-(phenylsulfonyl)amino)-3-(SR)-(hydroxymethyl)-4-(SR)-phenylcyclopentane (Higher R$_f$ isomer from Step C) (65 mg, 0.2 mmol) in methylene chloride (2 mL) was added. The reaction was stirred at −70° C. for 1.5 h and then DIPEA (0.35 mL, 2.0 mmol) was added. After a further 10 min, the mixture was allowed to warm to RT for 1 h and was then diluted with methylene chloride and poured into dilute aq. HCl and the layers were separated. The aq. layer was reextracted with a second portion of methylene chloride and the organic layers were each washed with brine, dried over sodium sulfate, combined and concentrated in vacuo. The residue was purified by FC using a gradient of 20 to 30% ethyl acetate in hexanes to give the title product (57 mg) as an oil.

NMR (CDCl$_3$) δ: 1.75–1.85 (m, 2H), 2.05–2.2 (m, 2H), 2.81 (s, 3H), 2.8–2.95 (m, 1H), 3.2–3.3 (m, 1H), 4.4–4.5 (m, 1H), 7.1–7.35 (m, 5H), 7.45–7.6 (m, 3H), 7.81 (m, 2H).

Step E: 1-(RS)-(N-(Methyl)-N-(phenylsulfonyl)amino)-3-(SR)-((4-(N-(benzyloxycarbonyl)-N-(ethyl)amino) piperidin-1-yl)methyl)-4-(SR)-phenylcyclopentane hydrochloride salt To a solution of 1-(RS)-(N-(methyl)-N-(phenylsulfonyl) amino)-3-(SR)-(formyl)-4-(SR)-phenylcyclopentane (from Step D, derived from Higher R$_f$ isomer in Step C) (10 mg, 0.029 mmol) (from Step F) in 1,2-dichloroethane (1 mL) was added 4-(N-(benzyloxycarbonyl)-N-(ethyl)amino) piperidine hydrochloride (18 mg, 0.058 mmol) and DIPEA (0.010 mL, 0.058 mmol). After 15 min, sodium triacetoxyborohydride (19 mg, 0.087 mmol) was added and the reaction was stirred at RT for 4–16 h. The reaction was evaporated under nitrogen, quenched with aq. sodium carbonate and extracted 3 times with ethyl acetate. The organic layers were each washed with brine, dried over sodium sulfate, combined and concentrated in vacuo. The residue was purified by Prep TLC eluting with 2–5% methanol in methylene chloride to give the title product (17 mg) as the free amine. The hydrochloride salt was prepared by taking up the free amine in ether, addition of excess 1M hydrogen chloride in ether and evaporation to dryness to afford the title compound usually as a white solid.

NMR (CDCl) (free amine) δ: 1.06 (br t, 3H), 1.3–1.8 (3 m, 6H), 1.8–1.95 (m,4H), 2.1–2.3 (m, 3H), 2.45–2.55 (m, 1H), 2.55–2.65 (m, 1H), 2.83 (m, 1H), 3.66 and 3.70 (2 s, 3H), 3.1–3.25 (m, 2H), 3.6–4.0 (2H), 4.48 (m, 1H), 5.10 (s, 2H), 7.1–7.4 (m, 5H), 7.4–7.6 (m, 3H), 7.8 (m, 2H).

MS (NH$_3$/ESI): m/z 590 (M+1).

EXAMPLE 11A 1-(RS)-(N-(Methyl)-N-(phenylsulfonyl)amino)-3-(SR)-((4-(N-(benzylaminocarbonyl)-N-(propyl)amino)piperidin-1-yl)methyl)-4-(SR)-phenylcyclopentane hydrochloride salt Using essentially the same procedure and aldehyde as in Example 11, Step E but substituting 4-(N-(benzylaminocarbonyl)-N-(propyl)amino)piperidine hydrochloride, the title compound was prepared.

MS (NH$_3$/ESI): m/z 603 (M+1).

EXAMPLE 11B 1-(RS)-(N-(Methyl)-N-(phenylsulfonyl)amino)-3-(SR)-((4-(N-(4-nitrobenzyloxycarbonyl)-N-(allyl)amino)piperidin-1-yl)methyl)-4-(SR)-phenylcyclopentane hydrochloride salt Using essentially the same procedure and aldehyde as in Example 11, Step E but substituting 4-(N-(4-nitrobenzyloxycarbonyl)-N-(allyl)amino)piperidine hydrochloride, the title compound was prepared.

MS (NH$_3$/ESI): m/z 647 (M+1).

EXAMPLE 12

1-(SR)-(N-(Methyl)-N-(phenylsulfonyl)amino)-3-(SR)-((4-(N-(benzyloxycarbonyl)-N-(ethyl)amino)piperidin-1-yl)methyl)-4-(SR)-phenylcyclopentane hydrochloride salt Using essentially the same procedures as in Example 11, Step D–E but substituting the lower R$_f$ product from Example 11, Step C, the title compound was prepared.

MS (NH$_3$/ESI): m/z 590 (M+1).

EXAMPLE 12A 1-(SR)-(N-(Methyl)-N-(phenylsulfonyl)amino)-3-(SR)-((4-(N-(benzylaminocarbonyl)-N-(propyl)amino)piperidin-1-yl)methyl)-4-(SR)-phenylcyclopentane hydrochloride salt Using essentially the same procedure and aldehyde as in Example 12, but substituting 4-(N-(benzylaminocarbonyl)-N-(propyl)amino)piperidine hydrochloride, the title compound was prepared.

MS (NH$_3$/ESI): m/z 603 (M+1).

EXAMPLE 12B 1-(SR)-(N-(Methyl)-N-(phenylsulfonyl)amino)-3-(SR)-((4-(N-(4-nitrobenzyloxycarbonyl)-N-(allyl)amino)piperidin-1-yl)methyl)-4-(SR)-phenylcyclopentane hydrochloride salt Using essentially the same procedure and aldehyde as in Example 12, but substituting 4-(N-(4-nitrobenzyloxycarbonyl)-N-(propyl)amino)piperidine hydrochloride, the title compound was prepared.

MS (NH$_3$/ESI): m/z 647 (M+1).

EXAMPLE 13

1-(RS)-(N-(Methyl)-N-(phenylcarbonyl)amino)-3-(SR)-((4-(N-(benzyloxycarbonyl)-N-(ethyl)amino)piperidin-1-yl)methyl)-4-(SR)-phenylcyclopentane hydrochloride salt Using essentially the same procedures as in Example 11, Steps B–E but substituting benzoyl chloride in Step B, the title compound was prepared.

NMR (CDCl$_3$) (free amine) δ: 1.07 (br t, 3H), 1.4–1.6 (2 m, 3H), 1.8–2.0 (m,4H), 2.0–2.5 (m, 5H), 2.5–2.7 (m, 1H), 2.7–2.9 (m, 1H), 2.9–3.3 (m, 4H), 3.6–4.0 (2 m, 1H), 4.25 (m, 1H), 5.10 (s, 2H), 7.1–7.4 (3 m, 10H).

MS (NH$_3$/ESI): m/z 554 (M+1).

EXAMPLE 13A 1-(RS)-(N-(Methyl)-N-(phenylcarbonyl)amino)-3-(SR)-((4-(N-(benzylaminocarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(benzylaminocarbonyl)-N-(propyl)amino)piperidine hydrochloride, the title compound was prepared.

MS (NH$_3$/ESI): m/z 567 (M+1).

EXAMPLE 13B 1-(RS)-(N-(Methyl)-N-(phenylcarbonyl)amino)-3-(SR)-((4-(N-(4-nitrobenzyloxycarbonyl)-N-(allyl)amino)piperidin-1-yl)methyl)-4-(SR)-phenylcyclopentane hydrochloride salt Using essentially the same procedure and aldehyde as in Example 13, but substituting 4-(N-(4-nitrobenzyloxycarbonyl)-N-(allyl)amino)piperidine hydrochloride, the title compound was prepared.

MS (NH$_3$/ESI): m/z 611 (M+1).

EXAMPLE 13C 1-(RS)-(N-(Methyl)-N-(phenylcarbonyl)amino)-3-(SR)-((4-(N-(4-nitrobenzyloxycarbonyl)-N-(propargyl)amino)piperidin-1-yl)methyl)-4-(SR)-phenylcyclopentane hydrochloride salt Using essentially the same procedure and aldehyde as in Example 13, but substituting 4-(N-(4-nitrobenzyloxycarbonyl)-N-(propargyl)amino)piperidine hydrochloride, the title compound was prepared.

MS (NH$_3$/ESI): m/z 609 (M+1).

EXAMPLE 13D 1-(RS)-(N-(Methyl)-N-(phenylcarbonyl)amino)-3-(SR)-((4-(N-(4-nitrobenzyloxycarbonyl)-N-(2-hydroxyeth-1-yl)amino)piperidin-1-yl)methyl)-4-(SR)-phenylcyclopentane hydrochloride salt Using essentially the same procedure and aldehyde as in Example 13, but substituting 4-(N-(4-nitrobenzyloxycarbonyl)-N-(2-hydroxyeth-1-yl)amino)piperidine hydrochloride, the title compound was prepared.

MS (NH$_3$/ESI): m/z 615 (M+1).

EXAMPLE 13E 1-(RS)-(N-(Methyl)-N-(phenylcarbonyl)amino)-3-(SR)-((4-(N-(2-nitrobenzylcarbonyl)-N-(allyl)amino)piperidin-1-yl)methyl)-4-(SR)-phenylcyclopentane hydrochloride salt Using essentially the same procedure and aldehyde as in Example 13, but substituting 4-(N-(2-nitrobenzylcarbonyl)-

N-(allyl)amino)piperidine hydrochloride, the title compound was prepared.

MS (NH$_3$/ESI): m/z 595 (M+1).

EXAMPLE 13F 1-(RS)-(N-(Methyl)-N-(phenylcarbonyl)amino)-3-(SR)-((4-(N-(3-nitrobenzylcarbonyl)-N-(allyl)amino)piperidin-1-yl)methyl)-4-(SR)-phenylcyclopentane hydrochloride salt Using essentially the same procedure and aldehyde as in Example 13, but substituting 4-(N-(3-nitrobenzylcarbonyl)-N-(allyl)amino)piperidine hydrochloride, the title compound was prepared.

MS (NH$_3$/ESI): m/z 595 (M+1).

EXAMPLE 13G 1-(RS)-(N-(Methyl)-N-(phenylcarbonyl)amino)-3-(SR)-((4-(N-(4-nitrobenzylcarbonyl)-N-(allyl)amino)piperidin-1-yl)methyl)-4-(SR)-phenylcyclopentane hydrochloride salt Using essentially the same procedure and aldehyde as in Example 13, but substituting 4-(N-(4-nitrobenzylcarbonyl)-N-(allyl)amino)piperidine hydrochloride, the title compound was prepared.

MS (NH$_3$/ESI): m/z 595 (M+1).

EXAMPLE 13H 1-(RS)-(N-(Methyl)-N-(phenylcarbonyl)amino)-3-(SR)-((4-(N-(3-nitrobenzylaminocarbonyl)-N-(allyl)amino)piperidin-1-yl)methyl)-4-(SR)-phenylcyclopentane hydrochloride salt Using essentially the same procedure and aldehyde as in Example 13, but substituting 4-(N-(3-nitrobenzylaminocarbonyl)-N-(allyl)amino)piperidine hydrochloride, the title compound was prepared.

MS (NH$_3$/ESI): m/z 610 (M+1).

EXAMPLE 13I 1-(RS)-(N-(Methyl)-N-(phenylcarbonyl)amino)-3-(SR)-((4-(N-(4-nitrobenzylaminocarbonyl)-N-(allyl)amino)piperidin-1-yl)methyl)-4-(SR)-phenylcyclopentane hydrochloride salt Using essentially the same procedure and aldehyde as in Example 13, but substituting 4-(N-(4-nitrobenzylaminocarbonyl)-N-(allyl)amino)piperidine hydrochloride, the title compound was prepared.

MS (NH$_3$/ESI): m/z 610 (M+1).

EXAMPLE 13J 1-(RS)-(N-(Methyl)-N-(phenylcarbonyl)amino)-3-(SR)-((4-(N-(phenylaminocarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(phenylaminocarbonyl)-N-(propyl)amino)piperidine hydrochloride, the title compound was prepared.

MS (NH$_3$/ESI): m/z 553 (M+1).

EXAMPLE 13K 1-(RS)-(N-(Methyl)-N-(phenylcarbonyl)amino)-3-(SR)-((4-(N-(benzylcarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(benzylcarbonyl)-N-(propyl)amino)piperidine hydrochloride, the title compound was prepared.

MS (NH$_3$/ESI): m/z 552 (M+1).

EXAMPLE 13L 1-(RS)-(N-(Methyl)-N-(phenylcarbonyl)amino)-3-(SR)-((4-(N-(cyclohexylmethyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(cyclohexylmethyloxycarbonyl)-N-(propyl)amino)piperidine hydrochloride, the title compound was prepared.

MS (NH$_3$/ESI): m/z 574 (M+1).

EXAMPLE 13M 1-(RS)-(N-(Methyl)-N-(phenylcarbonyl)amino)-3-(SR)-((4-(N-(3-(phenyl)prop-1-yloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(3-(phenyl)prop-1-yloxycarbonyl)-N-(propyl)amino)piperidine hydrochloride, the title compound was prepared.

MS (NH$_3$/ESI): m/z 596 (M+1).

EXAMPLE 13N 1-(RS)-(N-(Methyl)-N-(phenylcarbonyl)amino)-3-(SR)-((4-(N-(benzyloxycarbonyl)-N-(prop-2-yl)amino)piperidin-1-yl)methyl)-4-(SR)-phenylcyclopentane hydrochloride salt Using essentially the same procedure and aldehyde as in Example 13, but substituting 4-(N-(benzyloxycarbonyl)-N-(prop-2-yl)amino)piperidine hydrochloride, the title compound was prepared.

MS (NH$_3$/ESI): m/z 568 (M+1).

EXAMPLE 13O 1-(RS)-(N-(Methyl)-N-(phenylcarbonyl)amino)-3-(SR)-((4-(N-(benzyloxycarbonyl)-N-(cyclopropylmethyl)amino)piperidin-1-yl)methyl)-4-(SR)-phenylcyclopentane hydrochloride salt Using essentially the same procedure and aldehyde as in Example 13, but substituting 4-(N-(benzyloxycarbonyl)-N-(cyclopropylmethyl)amino)piperidine hydrochloride, the title compound was prepared.

MS (NH$_3$/ESI): m/z 580 (M+1).

EXAMPLE 13P 1-(RS)-(N-(Methyl)-N-(phenylcarbonyl)amino)-3-(SR)-((4-(N-(methoxycarbonyl)-N-(3,5,5-trimethylhex-1-yl)amino)piperidin-1-yl)methyl)-4-(SR)-phenylcyclopentane hydrochloride salt Using essentially the same procedure and aldehyde as in Example 13, but substituting 4-(N-(methoxycarbonyl)-N-(3,5,5-trimethylhex-1-yl)amino)piperidine hydrochloride, the title compound was prepared.

MS (NH$_3$/ESI): m/z 576 (M+1).

EXAMPLE 13Q 1-(RS)-(N-(Methyl)-N-(phenylcarbonyl)amino)-3-(SR)-((4-(N-(ethoxycarbonyl)-N-(cyclohexylmethyl)amino)piperidin-1-yl)methyl)-4-(SR)-phenylcyclopentane hydrochloride salt Using essentially the same procedure and aldehyde as in Example 13, but substituting 4-(N-(ethoxycarbonyl)-N-

(cyclohexylmethyl)amino)piperidine hydrochloride, the title compound was prepared.

MS (NH$_3$/ESI): m/z 560 (M+1).

EXAMPLE 13R 1-(RS)-(N-(Methyl)-N-(phenylcarbonyl)amino)-3-(SR)-((4-(N-(2-(phenyl)eth-1-yloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(2-(phenyl)eth-1-yloxycarbonyl)-N-(propyl)amino)piperidine hydrochloride, the title compound was prepared.

MS (NH$_3$/ESI): m/z 582 (M+1).

EXAMPLE 13S 1-(RS)-(N-(Methyl)-N-(phenylcarbonyl)amino)-3-(SR)-((4-(N-(4-(phenyl)benzyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(4-(phenyl)benzyloxycarbonyl)-N-(propyl)amino)piperidine hydrochloride, the title compound was prepared.

MS (NH$_3$/ESI): m/z 644 (M+1).

EXAMPLE 13T 1-(RS)-(N-(Methyl)-N-(phenylcarbonyl)amino)-3-(SR)-((4-(N-(4-(2-naphthyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(2-naphthyloxycarbonyl)-N-(propyl)amino)piperidine hydrochloride, the title compound was prepared.

MS (NH$_3$/ESI): m/z 618 (M+1).

EXAMPLE 13U 1-(RS)-(N-(Methyl)-N-(phenylcarbonyl)amino)-3-(SR)-((4-(N-(4-(1-naphthyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(1-naphthyloxycarbonyl)-N-(propyl)amino)piperidine hydrochloride, the title compound was prepared.

MS (NH$_3$/ESI): m/z 618 (M+1).

EXAMPLE 13V 1-(RS)-(N-(Methyl)-N-(phenylcarbonyl)amino)-3-(SR)-((4-(N-(4-(methoxycarbonyl)-N-(n-hexyl)amino)piperidin-1-yl)methyl)-4-(SR)-phenylcyclopentane hydrochloride salt Using essentially the same procedure and aldehyde as in Example 13, but substituting 4-(N-(methoxycarbonyl)-N-(n-hexyl)amino)piperidine hydrochloride, the title compound was prepared.

MS (NH$_3$/ESI): m/z 534 (M+1).

EXAMPLE 13W 1-(RS)-(N-(Methyl)-N-(phenylcarbonyl)amino)-3-(SR)-((4-(N-(4-(n-butyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(n-butyloxycarbonyl)-N-(propyl)amino)piperidine hydrochloride, the title compound was prepared.

MS (NH$_3$/ESI): m/z 534 (M+1).

EXAMPLE 13X 1-(RS)-(N-(Methyl)-N-(phenylcarbonyl)amino)-3-(SR)-((4-(N-(4-(trifluoro)benzyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(4-(4-(trifluoro)benzyloxycarbonyl)-N-(propyl)amino)piperidine hydrochloride, the title compound was prepared.

MS (NH$_3$/ESI): m/z 636 (M+1).

EXAMPLE 13Y 1-(RS)-(N-(Methyl)-N-(phenylcarbonyl)amino)-3-(SR)-((4-(N-(4-(methyl)benzyloxycarbonyl)-N-(propyl)amino)piperidin-1-yl)methyl)-4-(SR)-phenylcyclopentane hydrochloride salt Using essentially the same procedure and aldehyde as in Example 13, but substituting 4-(N-(4-(4-(methyl)benzyloxycarbonyl)-N-(propyl)amino)piperidine hydrochloride, the title compound was prepared.

MS (NH$_3$/ESI): m/z 582 (M+1).

EXAMPLE 13Z 1-(RS)-(N-(Methyl)-N-(phenylcarbonyl)amino)-3-(SR)-((4-(N-(benzyloxycarbonyl)-N-(1-methylprop-1-yl)amino)piperidin-1-yl)methyl)-4-(SR)-phenylcyclopentane hydrochloride salt Using essentially the same procedure and aldehyde as in Example 13, but substituting 4-(N-(4-(benzyloxycarbonyl)-N-(1-methylprop-1-yl)amino)piperidine hydrochloride, the title compound was prepared.

MS (NH$_3$/ESI): m/z 582 (M+1).

EXAMPLE 13AA 1-(RS)-(N-(Methyl)-N-(phenylcarbonyl)amino)-3-(SR)-((4-(N-(benzyloxycarbonyl)-N-(2-methylbut-1-yl)amino)piperidin-1-yl)methyl)-4-(SR)-phenylcyclopentane hydrochloride salt Using essentially the same procedure and aldehyde as in Example 13, but substituting 4-(N-(4-(benzyloxycarbonyl)-N-(2-methylbut-1-yl)amino)piperidine hydrochloride, the title compound was prepared.

MS (NH$_3$/ESI): m/z 596 (M+1).

EXAMPLE 13BB 1-(RS)-(N-(Methyl)-N-(phenylcarbonyl)amino)-3-(SR)-((4-(N-(benzyloxycarbonyl)-N-(3,3-dimethylbut-1-yl)amino)piperidin-1-yl)methyl)-4-(SR)-phenylcyclopentane hydrochloride salt Using essentially the same procedure and aldehyde as in Example 13, but substituting 4-(N-(4-(benzyloxycarbonyl)-N-(3,3-dimethylbut-1-yl)amino)piperidine hydrochloride, the title compound was prepared.

MS (NH$_3$/ESI): m/z 610 (M+1).

EXAMPLE 14

1-(SR)-(N-(Methyl)-N-(phenylcarbonyl)amino)-3-(SR)-((4-(N-(benzyloxycarbonyl)-N-(ethyl)amino)piperidin-1-yl)methyl)-4-(SR)-phenylcyclopentane hydrochloride salt Using essentially the same procedures as in Example 11, Steps B–E but substituting the lower R$_f$ product from Example 11, Step C and benzoyl chloride in Step B, the title compound was prepared.

MS (NH₃/ESI): m/z 554 (M+1).

EXAMPLE 14A 1-(SR)-(N-(Methyl)-N-(phenylcarbonyl)amino)-3-(SR)-((4-(N-(benzylaminocarbonyl)-N-(propyl)amino)piperidin-1-yl)methyl)-4-(SR)-phenylcyclopentane hydrochloride salt Using essentially the same procedure and aldehyde as in Example 14, but substituting 4-(N-(benzylaminocarbonyl)-N-(propyl)amino)piperidine hydrochloride, the title compound was prepared.

MS (NH₃/ESI): m/z 567 (M+1).

EXAMPLE 15

1-(RS)-(N-(Methyl)-N-(t-butoxycarbonyl)amino)-3-(SR)-((4-(N-(benzylaminocarbonyl)-N-(propyl)amino)piperidin-1-yl)methyl)-4-(SR)-phenylcyclopentane Using essentially the same procedures as in Example 11, Step B–E but substituting di-t-butyl dicarbonyl in Step B, the higher $R_f$ product from Step C in Step D, and 4-(N-(benzylaminocarbonyl)-N-(propyl)amino)piperidine hydrochloride in Step E, the title compound was prepared.

MS (NH₃/ESI): m/z 563 (M+1).

EXAMPLE 16

1-(RS)-(N-(Methyl)-N-(2-chlorophenylcarbonyl)amino)-3-(SR)-((4-(N-(benzyloxycarbonyl)-N-(propyl)amino)piperidin-1-yl)methyl)-4-(SR)-phenylcyclopentane Step A: 1-(RS)-(Methylamino)-3-(SR)-((4-(N-(benzyloxycarbonyl)-N-(propyl)amino)piperidin-1-yl)methyl)-4-(SR)-phenylcyclopentane hydrochloride A solution of hydrogen chloride (2.3 mmol) in methanol was prepared by addition of acetyl chloride (0.165 mL, 2.3 mmol) to methanol (10 mL) and aging for 15 min. To this was added 1-(RS)-(N-(methyl)-N-(t-butoxycarbonyl)amino)-3-(SR)-((4-(N-(benzylaminocarbonyl)-N-(propyl)amino)piperidin-1-yl)methyl)-4-(SR)-phenylcyclopentane from Example 15 (135 mg, 0.23 mmol). After 16 h, the volatiles were removed in vacuo to dryness to give the title compound hydrochloride salt.

Step B: 1-(RS)-(N-(Methyl)-N-(2-chlorophenylcarbonyl)amino)-3-(SR)-((4-(N-(benzyloxycarbonyl)-N-(propyl)amino)piperidin-1-yl)methyl)-4-(SR)-phenylcyclopentane hydrochloride To a solution of 1-(RS)-(methylamino)-3-(SR)-((4-(N-(benzyloxycarbonyl)-N-(propyl)amino)piperidin-1-yl)methyl)-4-(SR)-phenylcyclopentane hydrochloride from Step A (5.5 mg, 0.012 mmol) in methylene chloride (1 mL) was added N-methyl morpholine (0.005 mL, 0.035 mmol) and 2-chlorobenzoyl chloride (4 mg, 0.024 mmol). After 16 h, the reaction was concentrated and the residue purified on Prep TLC to afford the free amine of the title compound. This was taken up in ether and excess 1N hydrogen chloride in ether was added. The volatiles were removed under a stream of nitrogen and evaporated to dryness under vacuum.

MS (NH₃/ESI): m/z 601 (M+1).

EXAMPLE 16A 1-(RS)-(N-(Methyl)-N-(1-naphthylsulfonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting 1-naphthylsulfonyl chloride, the title compound was prepared.

MS (NH₃/ESI): m/z 653 (M+1).

EXAMPLE 16B 1-(RS)-(N-(Methyl)-N-(3-chlorophenylcarbonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting 3-chlorobenzoyl chloride, the title compound was prepared.

MS (NH₃/ESI): m/z 601 (M+1).

EXAMPLE 16C 1-(RS)-(N-(Methyl)-N-(4-chlorophenylcarbonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting 4-chlorobenzoyl chloride, the title compound was prepared.

MS (NH₃/ESI): m/z 601 (M+1).

EXAMPLE 16D 1-(RS)-(N-(Methyl)-N-(3-trifluoromethylphenylcarbonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting 3-trifluoromethylbenzoyl chloride, the title compound was prepared.

MS (NH₃/ESI): m/z 635 (M+1).

EXAMPLE 16E 1-(RS)-(N-(Methyl)-N-(4-trifluoromethylphenylcarbonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting 4-trifluoromethylbenzoyl chloride, the title compound was prepared.

MS (NH₃/ESI): m/z 635 (M+1).

EXAMPLE 16F 1-(RS)-(N-(Methyl)-N-(3-methylphenylcarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting 3-methylbenzoyl chloride, the title compound was prepared.

MS (NH$_3$/ESI): m/z 581 (M+1).

EXAMPLE 16G 1-(RS)-(N-(Methyl)-N-(4-methylphenylcarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting 4-methylbenzoyl chloride, the title compound was prepared.

MS (NH$_3$/ESI): m/z 581 (M+1).

EXAMPLE 16H 1-(RS)-(N-(Methyl)-N-(benzylcarbonyl)amino)-3-
(SR)-((4-(N-(benzyloxycarbonyl)-N-(propyl)amino)
piperidin-1-yl)methyl)-4-(SR)-phenylcyclopentane Using essentially the same procedure as in Example 16, Step B but substituting phenylacetyl chloride, the title compound was prepared.

MS (NH$_3$/ESI): m/z 581 (M+1).

EXAMPLE 16I 1-(RS)-(N-(Methyl)-N-(phenethylcarbonyl)amino)-
3-(SR)-((4-(N-(benzyloxycarbonyl)-N-(propyl)
amino)piperidin-1-yl)methyl)-4-(SR)-
phenylcyclopentane Using essentially the same procedure as in Example 16, Step B but substituting dihydrocinnamyl chloride, the title compound was prepared.

MS (NH$_3$/ESI): m/z 595 (M+1).

EXAMPLE 16J 1-(RS)-(N-(Methyl)-N-(methylaminothiocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting methyl isothiocyanate, the title compound was prepared.

MS (NH$_3$/ESI): m/z 536 (M+1).

EXAMPLE 16K 1-(RS)-(N-(Methyl)-N-(dimethylaminocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting dimethylcarbamoyl chloride, the title compound was prepared.

MS (NH$_3$/ESI): m/z 534 (M+1).

EXAMPLE 16L 1-(RS)-(N-(Methyl)-N-(phenylaminocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting phenyl isocyanate, the title compound was prepared.

MS (NH$_3$/ESI): m/z 582 (M+1).

EXAMPLE 16M 1-(RS)-(N-(Methyl)-N-(benzylaminocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting benzyl isocyanate, the title compound was prepared.

MS (NH$_3$/ESI): m/z 596 (M+1).

EXAMPLE 16N 1-(RS)-(N-(Methyl)-N-(benzyloxycarbonyl)amino)-
3-(SR)-((4-(N-(benzyloxycarbonyl)-N-(propyl)
amino)piperidin-1-yl)methyl)-4-(SR)-
phenylcyclopentane Using essentially the same procedure as in Example 16, Step B but substituting benzyl chloroformate, the title compound was prepared.

MS (NH$_3$/ESI): m/z 597 (M+1).

EXAMPLE 16O 1-(RS)-(N-(Methyl)-N-(3-fluorophenylcarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting 3-fluorobenzoyl chloride, the title compound was prepared.

MS (NH$_3$/ESI): m/z 585 (M+1).

EXAMPLE 16P 1-(RS)-(N-(Methyl)-N-(4-fluorophenylcarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting 4-fluorobenzoyl chloride, the title compound was prepared.

MS (NH$_3$/ESI): m/z 585 (M+1).

EXAMPLE 16Q 1-(RS)-(N-(Methyl)-N-(cyclohexylcarbonyl)amino)-
3-(SR)-((4-(N-(benzyloxycarbonyl)-N-(propyl)
amino)piperidin-1-yl)methyl)-4-(SR)-
phenylcyclopentane Using essentially the same procedure as in Example 16, Step B but substituting cyclohexanoyl chloride, the title compound was prepared.

MS (NH$_3$/ESI): m/z 573 (M+1).

EXAMPLE 16R 1-(RS)-(N-(Methyl)-N-(acetylcarbonyl)amino)-3-
(SR)-((4-(N-(benzyloxycarbonyl)-N-(propyl)amino)
piperidin-1-yl)methyl)-4-(SR)-phenylcyclopentane Using essentially the same procedure as in Example 16, Step B but substituting acetyl chloride, the title compound was prepared.

MS (NH$_3$/ESI): m/z 505 (M+1).

EXAMPLE 16S 1-(RS)-(N-(Methyl)-N-(n-hexylcarbonyl)amino)-3-
(SR)-((4-(N-(benzyloxycarbonyl)-N-(propyl)amino)
piperidin-1-yl)methyl)-4-(SR)-phenylcyclopentane Using essentially the same procedure as in Example 16, Step B but substituting n-heptanoyl chloride, the title compound was prepared.

MS (NH$_3$/ESI): m/z 575 (M+1).

EXAMPLE 17

1-(SR)-(N-(Methyl)-N-(t-butoxycarbonyl)amino)-3-
(SR)-((4-(N-(benzylaminocarbonyl)-N-(propyl)
amino)piperidin-1-yl)methyl)-4-(SR)-
phenylcyclopentane Using essentially the same procedures as in Example 11, Step B-E but substituting di-t-butyl dicarbonate in Step B, the lower R$_f$ product from Step C in Step D, and 4-(N-(benzylaminocarbonyl)-N-(propyl)amino)piperidine hydrochloride in Step E, the title compound was prepared.

MS (NH$_3$/ESI): m/z 563 (M+1).

EXAMPLE 18

1-(SR)-(N-(Methyl)-N-(3-chlorophenylcarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedures as in Example 16, Step A–B but substituting 1-(SR)-(N-(methyl)-N-(t-butoxycarbonyl)amino)-3-(SR)-((4-(N-(benzylaminocarbonyl)-N-(propyl)amino)piperidin-1-yl)methyl)-4-(SR)-phenylcyclopentane from Example 17 in Step A and 3-chlorobenzoyl chloride in Step B, the title compound was prepared.

MS (NH$_3$/ESI): m/z 601 (M+1).

EXAMPLE 18A 1-(SR)-(N-(Methyl)-N-(4-chlorophenylcarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting 4-chlorobenzoyl chloride, the title compound was prepared.

MS (NH$_3$/ESI): m/z 601 (M+1).

EXAMPLE 18B 1-(SR)-(N-(Methyl)-N-(cyclohexylcarbonyl)amino)-
3-(SR)-((4-(N-(benzyloxycarbonyl)-N-(propyl)
amino)piperidin-1-yl)methyl)-4-(SR)-
phenylcyclopentane Using essentially the same procedure as in Example 16, Step B but substituting cyclohexanoyl chloride, the title compound was prepared.

MS (NH$_3$/ESI): m/z 573 (M+1).

EXAMPLE 18C 1-(SR)-(N-(Methyl)-N-(n-hexylcarbonyl)amino)-3-
(SR)-((4-(N-(benzyloxycarbonyl)-N-(propyl)amino)
piperidin-1-yl)methyl)-4-(SR)-phenylcyclopentane Using essentially the same procedure as in Example 16, Step B but substituting n-heptanoyl chloride, the title compound was prepared.

MS (NH$_3$/ESI): m/z 575 (M+1).

EXAMPLE 18D 1-(SR)-(N-(Methyl)-N-(methylaminothiocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting methyl isothiocyanate, the title compound was prepared.

MS (NH$_3$/ESI): m/z 536 (M+1).

EXAMPLE 18E 1-(SR)-(N-(Methyl)-N-(benzylaminocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting benzyl isocyanate, the title compound was prepared.

MS (NH$_3$/ESI): m/z 596 (M+1).

EXAMPLE 18F 1-(SR)-(N-(Methyl)-N-(dimethylaminocarbonyl)
amino)-3-(SR)-((4-(N-(benzyloxycarbonyl)-N-
(propyl)amino)piperidin-1-yl)methyl)-4-(SR)-
phenylcyclopentane Using essentially the same procedure as in Example 16, Step B but substituting dimethylcarbamoyl chloride, the title compound was prepared.

MS (NH$_3$/ESI): m/z 534 (M+1).

EXAMPLE 18G 1-(SR)-(N-(Methyl)-N-(methylsulfonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting methylsulfonyl chloride, the title compound was prepared.

MS (NH$_3$/ESI): m/z 540 (M+1).

EXAMPLE 18H 1-(SR)-(N-(Methyl)-N-(benzylcarbonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting phenylacetyl chloride, the title compound was prepared.

MS (NH$_3$/ESI): m/z 580 (M+1).

EXAMPLE 18I 1-(SR)-(N-(Methyl)-N-(iso-butyloxycarbonyl)amino)-3-(SR)-((4-(N-(benzyloxycarbonyl)-N-(propyl)amino)piperidin-1-yl)methyl)-4-(SR)-phenylcyclopentane Using essentially the same procedure as in Example 16, Step B but substituting iso-butyl chloroformate, the title compound was prepared.

MS (NH$_3$/ESI): m/z 563 (M+1).

EXAMPLE 19

1-(RS)-(N-(Methyl)-N-(iso-butyl)amino)-3-(SR)-((4-(N-(benzyloxycarbonyl)-N-(propyl)amino)piperidin-1-yl)methyl)-4-(SR)-phenylcyclopentane hydrochloride Using essentially the same procedure as in Example 11, Step E but substituting iso-butyraldehyde with 1-(RS)-(N-(methyl)amino)-3-(SR)-((4-(N-(benzyloxycarbonyl)-N-(propyl)amino)piperidin-1-yl)methyl)-4-(SR)-phenylcyclopentane, the title compound was prepared.

MS (NH$_3$/ESI): m/z 519 (M+1).

EXAMPLE 19A 1-(RS)-(N-(Methyl)-N-(cyclohexylmethyl)amino)-3-(SR)-((4-(N-(benzyloxycarbonyl)-N-(propyl)amino)piperidin-1-yl)methyl)-4-(SR)-phenylcyclopentane hydrochloride Using essentially the same procedure as in Example 11, Step E but substituting cyclohexane carboxaldehyde with 1-(RS)-(N-(methyl)amino)-3-(SR)-((4-(N-(benzyloxycarbonyl)-N-(propyl)amino)piperidin-1-yl)methyl)-4-(SR)-phenylcyclopentane, the title compound was prepared.

MS (NH$_3$/ESI): m/z 559 (M+1).

EXAMPLE 19B 1-(RS)-(N-(Methyl)-N-(benzyl)amino)-3-(SR)-((4-(N-(benzyloxycarbonyl)-N-(propyl)amino)piperidin-1-yl)methyl)-4-(SR)-phenylcyclopentane hydrochloride Using essentially the same procedure as in Example 11, Step E but substituting benzaldehyde with 1-(RS)-(N-(methyl)amino)-3-(SR)-((4-(N-(benzyloxycarbonyl)-N-(propyl)amino)piperidin-1-yl)methyl)-4-(SR)-phenylcyclopentane, the title compound was prepared.

MS (NH$_3$/ESI): m/z 553 (M+1).

EXAMPLE 19C 1-(RS)-(N-(Methyl)-N-(2-chlorobenzyl)amino)-3-(SR)-((4-(N-(benzyloxycarbonyl)-N-(propyl)amino)piperidin-1-yl)methyl)-4-(SR)-phenylcyclopentane hydrochloride Using essentially the same procedure as in Example 11, Step E but substituting 2-chlorobenzaldehyde with 1-(RS)-(N-(methyl)amino)-3-(SR)-((4-(N-(benzyloxycarbonyl)-N-(propyl)amino)piperidin-1-yl)methyl)-4-(SR)-phenylcyclopentane, the title compound was prepared.

MS (NH$_3$/ESI): m/z 463 (M+1-C$_7$H$_5$Cl).

EXAMPLE 19D 1-(RS)-(N-(Methyl)-N-(3-chlorobenzyl)amino)-3-(SR)-((4-(N-(benzyloxycarbonyl)-N-(propyl)amino)piperidin-1-yl)methyl)-4-(SR)-phenylcyclopentane hydrochloride Using essentially the same procedure as in Example 11, Step E but substituting 3-chlorobenzaldehyde with 1-(RS)-(N-(methyl)amino)-3-(SR)-((4-(N-(benzyloxycarbonyl)-N-(propyl)amino)piperidin-1-yl)methyl)-4-(SR)-phenylcyclopentane, the title compound was prepared.

MS (NH$_3$/ESI): m/z 463 (M+1-C$_7$H$_5$Cl).

EXAMPLE 19E 1-(RS)-(N-(Methyl)-N-(4-chlorobenzyl)amino)-3-(SR)-((4-(N-(benzyloxycarbonyl)-N-(propyl)amino)piperidin-1-yl)methyl)-4-(SR)-phenylcyclopentane hydrochloride Using essentially the same procedure as in Example 11, Step E but substituting 4-chlorobenzaldehyde with 1-(RS)-(N-(methyl)amino)-3-(SR)-((4-(N-(benzyloxycarbonyl)-N-(propyl)amino)piperidin-1-yl)methyl)-4-(SR)-phenylcyclopentane, the title compound was prepared.

MS (NH$_3$/ESI): m/z 463 (M+1-C$_7$H$_5$Cl).

EXAMPLE 20

1-(SR)-((t-Butoxycarbonyl)amino)-3-(SR)-((4-(N-(4-nitrobenzyloxycarbonyl)-N-(allyl)amino)piperidin-1-yl)methyl)-4-(SR)-phenylcyclopentane Step A: Methyl(+−)-trans-4-methylene-2-phenylcyclopentanoate A mixture of methyl trans-cinnamate (5.0 g, 31 mmol), tetrakis(triphenylphosphine)palladium(0) (2.6 g, 2.3 mmol), 1,2-bis(diphenylphosphino)ethane (0.70 g, 1.8 mmol) and 2-((trimethylsilyl)methyl)-2-propen-1-yl acetate (6.90 g, 37 mmol) in THF (60 mL) under argon was heated to reflux for 4 h. An additional aliquot of 2-((trimethylsilyl)methyl)-2-propen-1-yl acetate (3.40 g) was added and the reaction was continued for another 16 h. The volatiles were then removed in vacuo and the residue was purified by FC (10% ethyl acetate in hexanes) to afford the title compound (6.2 g).

NMR (CDCl$_3$) δ: 2.52 (m, 1H), 2.68 (m, 1H), 2.75–2.9 (m, 2H), 2.95 (ddd, 1H), 3.45 (ddd, 1H), 3.57 (s, 3H), 4.92 (m, 2H), 7.15–7.3 (m, 5H).

Step B: (+−)-trans-1-Hydroxymethyl-4-methylene-2-phenylcyclopentane

To a solution of methyl(+−)-trans-4-methylene-2-phenylcyclopentanoate (5.0 g, 23 mmol) from Step A in THF (30 mL) under nitrogen was added dropwise over 10 min 1M lithium aluminum hydride (LAH) in THF (23 mL). After 2 h at RT, the excess LAH was quenched by dropwise addition of ethyl acetate and the reaction was then poured into dilute aq. HCl. The mixture was extracted twice with ether and the organic layers were washed with brine, dried over sodium sulfate, combined and concentrated. The residue was purified by FC (20–30% ethyl acetate in hexanes) to afford the title product (4.5 g) as a white solid.

Step C: (+−)-trans-1-t-Butyldimethylsilyloxymethyl-4-methylene-2-phenylcyclopentane To a solution of (+−)-trans-1-hydroxymethyl-4-methylene-2-phenylcyclopentane from Step B (2.5 g, 13.3 mmol) in methylene chloride (50 mL) was added t-butyldimethylsilyl chloride (3.0 g, 20 mmol) and DIPEA (4.7 mL, 27 mmol). The reaction was stirred at RT for 16 h, poured into dilute aq. HCl and extracted twice with ether. The organic layers were washed with brine, dried over sodium sulfate, combined and concentrated. The residue was purified by FC (5% ethyl acetate in hexanes) to afford the title product. (4.2 g) as a oil.

NMR (CDCl$_3$) δ: −0.04 and −0.05 (2 s, 6H), 0.85 (s, 9H), 2.22 (m, 1H), 2.33 (tq, 1H), 2.48 (tq, 1H), 2.62 (br ddq, 1H), 2.76 (br ddq, 1H), 2.91 (ddd, 1H), 3.45 (dABq, 2H), 4.87 (m, 2H), 7.15–7.3 (m, 5H).

Step D: (+−)-trans-1-t-Butyldimethylsilyloxymethyl-4-oxo-2-phenylcyclopentane

Into a solution of (+−)-trans-1-t-butyldimethylsilyloxymethyl-4-methylene-2-phenylcyclopentane from Step C (2.2 g, 7.3 mmol) in methanol (100 mL) cooled in a dry ice/acetone bath was bubbled ozone until the blue color persisted. The excess ozone was removed with a stream of nitrogen and then dimethylsulfide (5 mL) was added. After 10 min, the bath was removed and the reaction was allowed to warm to RT over 2 h. The volatiles were removed in vacuo and the residue was purified by FC (15–30% ethyl acetate in hexanes) to give the title compound (1.9 g).

NMR (CDCl$_3$) δ: −0.01 and −0.03 (2 s, 6H), 0.86 (s, 9H), 2.2–2.5 (m, 4H), 2.71 (dd, 1H), 3.28 (m, 1H), 3.55 (dABq, 2H), 7.23 (m, 3H), 7.34 (m, 2H).

Step E: 1-(SR)-Benzylamino-3-(SR)-t-butyldimethylsilyloxymethyl-4-(SR)-phenylcyclopentane (Higher R$_f$ isomer) and 1-(RS)-benzylamino-3-(SR)-t-butyldimethylsilyloxymethyl-4-(SR)-phenylcyclopentane (Lower R$_f$ isomer)

To a solution of (+−)-trans-1-t-butyldimethylsilyloxymethyl-4-oxo-2-phenylcyclopentane from Step D (1.4 g, 4.6 mmol) in 1,2-dichloroethane (20 mL) was added benzylamine (1.0 g, 9.2 mmol) and acetic acid (0.55 mL, 9.2 mmol). After 10 min, sodium triacetoxyborohydride (1.95 g, 9.2 mmol) was added in portions and the reaction was stirred at RT for 1 hr. The reaction was quenched into dilute aq. sodium carbonate and the mixture was extracted twice with ethyl acetate. The organic layers were washed with brine, dried over sodium sulfate, combined and concentrated. The residue was purified by FC (15–50% ethyl acetate in hexanes) to separate the title products (1.35 and 0.50 g).

Step F: 1-(SR)-(t-Butoxycarbonyl)amino-3-(SR)-hydroxymethyl-4-(SR)-phenylcyclopentane (Higher R$_f$ isomer) and 1-(RS)-(t-butoxycarbonyl)amino-3-(SR)-hydroxymethyl-4-(SR)-phenylcyclopentane (Lower R$_f$ isomer)

A solution of HCl (6.8 mmol) in methanol (10 mL) was prepared by addition of acetyl chloride (0.50 mL, 6.8 mmol) and aging for 15 min. To this solution was added 1-(SR)-benzylamino-3-(SR)-t-butyldimethylsilyloxymethyl-4-(SR)-phenylcyclopentane (Higher R$_f$ isomer from Step E) (1.35 g, 3.4 mmol). After 2 h, TLC (50% ethyl acetate in hexanes) indicated the silyl had been removed.

To this solution was added 20% palladium hydroxide (150 mg, 50% by wt water), ammonium formate (4.5 g, 68 mmol) and an additional 30 mL of methanol. The reaction was heated at 60° C. for 6 h and RT for 16 h. The reaction was filtered and concentrated. The residue was taken up in water and extracted twice with methylene chloride to remove any remaining benzylamine intermediate. The aqueous layer was made basic with 2N sodium hydroxide and extracted twice with methylene chloride. The organic layers were washed with brine, dried over sodium sulfate, combined and concentrated to afford 460 mg of crude amino-alcohol.

The above product (450 mg, 2.35 mmol) was taken up in methylene chloride (10 mL), cooled in an ice bath and DIPEA (0.82 mL, 4.7 mmol) and di-t-butyl dicarbonate (565 mg, 2.59 mmol) were added. After 1 h, an additional aliquot of di-t-butyl dicarbonate (100 mg) was added. After an additional 1 h, the reaction was poured into dilute aq. HCl and extracted twice with methylene chloride. The organic layers were washed with brine, dried over sodium sulfate, combined and concentrated. The residue was purified by FC (30–40% ethyl acetate in hexanes) to afford the title compound (650 mg) as a white solid.

NMR (CDCl$_3$) δ: 1.43 (s, 9H), 1.45 (m, 1H), 1.9–2.1 (m, 2H), 2.17 (m, 1H), 2.40 (m, 1H), 3.01 (q, 1H), 3.59 (dABq, 2H), 4.20 (br m, 1H), 5.00 (br s, 1H), 7.15–7.3 (m, 5H).

Using essentially the same procedures as above, the lower isomer from Step E (0.50 g, 1.27 mmol) was also converted to the lower R$_f$ title compound (325 mg).

NMR (CDCl$_3$) δ: 1.43 (s, 9H), 1.58 (ddd, 1H), 1.78.1 (ddd, 1H), 2.02 (m, 1H), 2.29 (m, 1H), 2.47 (ddd, 1H), 2.76 (ddd, 1H), 3.54 (dABq, 2H), 4.06 (br m, 1H), 4.62 (br s, 1H), 7.15–7.3 (m, 5H).

Step G: 1-(SR)-(t-Butoxycarbonyl)amino-3-(SR)-formyl-4-(SR)-phenylcyclopentane (Higher R$_f$ isomer) and 1-(RS)-(t-butoxycarbonyl)amino-3-(SR)-formyl-4-(SR)-phenylcyclopentane (Lower R$_f$ isomer)

To a solution of oxalyl chloride (0.500 mL, 5.6 mmol) in methylene chloride (20 mL) at −70° C. was added dropwise DMSO (0.80 mL, 11 mmol). After 15 min, a solution of 1-(SR)-(t-butoxycarbonyl)amino-3-(SR)-hydroxymethyl-4-(SR)-phenylcyclopentane (Higher R$_f$ isomer) from Step F) (650 mg, 2.2 mmol) in methylene chloride (10 mL) was added. The reaction was stirred at −70° C. for 1.5 h and then DIPEA (3.9 mL, 22 mmol) in methylene chloride (5 mL) was added dropwise over 5 min. After a further 10 min, the mixture was allowed to warm to RT for 1 h and then diluted with methylene chloride and poured into dilute aq. HCl. The layers were separated. The aq. layer was reextracted with a second portion of methylene chloride and the organic layers were each washed with brine, dried over sodium sulfate, combined and concentrated in vacuo. The residue was purified by FC (20% ethyl acetate in hexanes) to give the title product (600 mg) as a white solid after vacuum drying.

Using essentially the same procedure as above, material derived from the lower isomer from Step E–F (0.320 g, 1.1 mmol) was also converted to the lower R$_f$ title compound (300 mg).

Step H: 1-(SR)-((t-Butoxycarbonyl)amino)-3-(SR)-((4-(N-(4-nitrobenzyloxycarbonyl)-N-(allyl)amino)piperidin-1-yl)methyl)-4-(SR)-phenylcyclopentane (Higher $R_f$ isomer)

To a solution of 1-((SR)-((t-butoxycarbonyl)amino)-3-(SR)-(formyl)-4-(SR)-phenylcyclopentane (from Step G, derived from Higher $R_f$ isomer in Step E) (30 mg, 0.11 mmol) in 1,2-dichloroethane (3 mL) was added 4-(N-(4-nitrobenzyloxycarbonyl)(N-allyl)amino)piperidine hydrochloride (45 mg, 0.126 mmol) and DIPEA (0.022 mL, 0.126 mmol). After 15 min, sodium triacetoxyborohydride (45 mg, 0.22 mmol) was added and the reaction was stirred at RT for 6 h. The reaction was diluted with methylene chloride, quenched with aq. sodium carbonate and extracted 3 times with methylene chloride. The organic layers were each washed with brine, dried over sodium sulfate, combined and concentrated in vacuo. The residue was purified by Prep TLC eluting with 5% methanol in methylene chloride to give the title product (66 mg) as the free amine.

MS (NH$_3$/ESI): m/z 593 (M+1).

EXAMPLE 21

1-(SR)-((t-Butoxycarbonyl)amino)-3-(SR)-((4-(N-(4-nitrobenzylaminocarbonyl)-N-(allyl)amino)piperidin-1-yl)methyl)-4-(SR)-phenylcyclopentane Using essentially the same procedure as Example 20, Step H, material derived from the higher isomer from Step E–G (0.295 g, 0.83 mmol) was also converted to the title compound (285 mg).

MS (NH$_3$/ESI): m/z 592 (M+1).

EXAMPLE 22

1-(RS)-((t-Butoxycarbonyl)amino)-3-(SR)-((4-(N-(4-nitrobenzylaminocarbonyl)-N-(allyl)amino)piperidin-1-yl)methyl)-4-(SR)-phenylcyclopentane Using essentially the same procedure as Example 20, Step H, material derived from the lower isomer from Step E–G (200 mg, 0.69 mmol) was also converted to the title compound (290 mg).

MS (NH$_3$/ESI): m/z 592 (M+1).

EXAMPLE 23

1-(SS)-((Phenylcarbonyl)amino)-3-(SR)-((4-(N-(4-nitrobenzyloxycarbonyl)-N-(allyl)amino)piperidin-1-yl)methyl)-4-(SR)-phenylcyclopentane Using essentially the same procedure as Example 16, Step A and B, 1-(SS)-((t-butoxycarbonyl)amino)-3-(SR)-((4-(N-(4-nitrobenzyloxycarbonyl)-N-(allyl)amino)piperidin-1-yl)methyl)-4-(SR)-phenylcyclopentane from Example 20, Step H (derived from the higher isomer from Example 20, Step E) was deblocked and acylated with benzoyl chloride to obtain the title compound.

MS (NH$_3$/ESI): m/z 597 (M+1).

EXAMPLE 24

1-(SS)-((Phenylsulfonyl)amino)-3-(SR)-((4-(N-(4-nitrobenzyloxycarbonyl)-N-(allyl)amino)piperidin-1-yl)methyl)-4-(SR)-phenylcyclopentane Using essentially the same procedure as Example 16, Step A and B, 1-(SS)-((t-butoxycarbonyl)amino)-3-(SR)-((4-(N-(4-nitrobenzyloxycarbonyl)-N-(allyl)amino)piperidin-1-yl)methyl)-4-(SR)-phenylcyclopentane from Example 20, Step H (derived from the higher isomer from Example 20, Step E) was deblocked and acylated with phenylsulfonyl chloride to obtain the title compound.

MS (NH$_3$/ESI): m/z 633 (M+1).

EXAMPLE 25

1-(SS)-((Phenylcarbonyl)amino)-3-(SR)-((4-(N-(4-nitrobenzylaminocarbonyl)-N-(allyl)amino)piperidin-1-yl)methyl)-4-(SR)-phenylcyclopentane Using essentially the same procedure as Example 16, Step A and B, 1-(SS)-((t-butoxycarbonyl)amino)-3-(SR)-((4-(N-(4-nitrobenzylaminocarbonyl)-N-(allyl)amino)piperidin-1-yl)methyl)-4-(SR)-phenylcyclopentane from Example 21 (derived from the higher isomer from Example 20, Step E) was deblocked and acylated with benzoyl chloride to obtain the title compound.

MS (NH$_3$/ESI): m/z 596 (M+1).

EXAMPLE 26

1-(SS)-((Phenylsulfonyl)amino)-3-(SR)-((4-(N-(4-nitrobenzylaminocarbonyl)-N-(allyl)amino)piperidin-1-yl)methyl)-4-(SR)-phenylcyclopentane Using essentially the same procedure as Example 16, Step A and B, 1-(SS)-((t-butoxycarbonyl)amino)-3-(SR)-((4-(N-(4-nitrobenzylaminocarbonyl)-N-(allyl)amino)piperidin-1-yl)methyl)-4-(SR)-phenylcyclopentane from Example 20, Step H (derived from the higher isomer from Example 20, Step E) was deblocked and acylated with phenylsulfonyl chloride to obtain the title compound.

MS (NH$_3$/ESI): m/z 632 (M+1).

EXAMPLE 27

1-(RS)-((Phenylcarbonyl)amino)-3-(SR)-((4-(N-(4-nitrobenzylaminocarbonyl)-N-(allyl)amino)piperidin-1-yl)methyl)-4-(SR)-phenylcyclopentane Using essentially the same procedure as Example 16, Step A and B, 1-(RS)-((t-butoxycarbonyl)amino)-3-(SR)-((4-(N-(4-nitrobenzylaminocarbonyl)-N-(allyl)amino)piperidin-1-yl)methyl)-4-(SR)-phenylcyclopentane from Example 22 (derived from the lower isomer from Example 20, Step E) was deblocked and acylated with benzoyl chloride to obtain the title compound.

MS (NH$_3$/ESI): m/z 596 (M+1).

EXAMPLE 28

1-(RS)-((Phenylsulfonyl)amino)-3-(SR)-((4-(N-(4-nitrobenzylaminocarbonyl)-N-(allyl)amino)piperidin-1-yl)methyl)-4-(SR)-phenylcyclopentane Using essentially the same procedure as Example 16, Step A and B, 1-(RS)-((t-butoxycarbonyl)amino)-3-(SR)-((4-(N-(4-nitrobenzylaminocarbonyl)-N-(allyl)amino)piperidin-1-yl)methyl)-4-(SR)-phenylcyclopentane from Example 22, Step H (derived from the lower isomer from Example 20, Step E) was deblocked and acylated with phenylsulfonyl chloride to obtain the title compound.

MS (NH$_3$/ESI): m/z 632 (M+1).

EXAMPLE 29

1-(R)-(N-(Methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane Step A: (+−)-trans-4-Methylene-2-phenylcyclopentanoic acid To a solution of methyl(+−)-trans-4-methylene-2-phenylcyclopentanoate prepared as in Example 20, Step A (28.4 g, 131 mmol) in methanol (400 mL) was added 5N sodium hydroxide (131 mL, 656 mmol). The reaction was heated at 65° C. for 1 h then cooled and concentrated. The residue was taken up diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+)-trans-4-Methylene-2-phenylcyclopentanoic acid, (S)-(−)-α-methylbenzylamine salt and (−)-trans-4-methylene-2-phenylcyclopentanoic acid, (R)-(+)-α-methylbenzylamine salt The crude (+−)-trans-4-methylene-2-phenylcyclopentanoic acid from Step A (assumed 131 mmol) was taken up in 2-propanol (400 mL), warmed to 80° C. and treated with (S)-(−)-α-methylbenzylamine (8.45 mL, 66 mmol). The mixture was stirred while allowed to cool to RT over 16 h and was then cooled to −10° C. for 1 h. The salt was filtered, washed with a small amount of ether to remove 2-propanol and air dried to give 6.442 g of salt. This was recrystallized from 2-propanol to give the title salt (4.713 g), $[\alpha]_D$=+56 (MeOH, c=0.20).

The combined mother liquors from above were concentrated and the residue taken up in water, acidified with 2M hydrochloric acid and extracted twice with methylene chloride. The organic layers were each washed with brine, dried over sodium sulfate, combined and concentrated in vacuo. The residue was taken up in 2-propanol (400 mL), warmed to 80° C. and treated with (R)-(+)-α-methylbenzylamine (9.1 mL, 70 mmol). The mixture was stirred while allowed to cool to RT over 16 h and was then cooled to −10° C. for 1 h. The salt was filtered, washed with a small amount of ether to remove 2-propanol and air dried to give 8.22 g of salt. This was recrystallized from 2-propanol to give the title salt (6.31 g), $[\alpha]_D$=−55 (MeOH, c=0.21).

Step C: (+ and −)-trans-4-Methylene-2-phenylcyclopentanoic acid

Method A

The (+)-trans-4-methylene-2-phenylcyclopentanoic acid, (S)-(−)-α-methylbenzylamine salt from Step B (4.7 g) was suspended in methylene chloride and water and acidified with 2M hydrochloric acid and extracted twice with methylene chloride. The organic layers were each washed with brine, dried over sodium sulfate, combined and concentrated in vacuo to give the title (+) acid (3.1 g), $[\alpha]_D$=+101 (MeOH, c=0.135).

Similarly, the (−)-trans-4-methylene-2-phenylcyclopentanoic acid, (R)-(+)-α-methylbenzylamine salt (6.3 g) was converted to the free (−)-title acid (4.23 g), $[\alpha]_D$=−103 (MeOH, c=0.23).

Method B

Step B1: 1-(S)-(((S)-(−)-4-Benzyl-2-oxazolidin-1-yl)carbonyl)-3-methylene-2-(S)-phenylcyclopentane (higher $R_f$) and 1-(R)-(((S)-(−)-4-benzyl-2-oxazolidin-1-yl)carbonyl)-3-methylene-2-(R)-phenylcyclopentane (lower $R_f$)

A solution of (+−)-trans-4-methylene-2-phenylcyclopentanoic acid (47.5 g, 235 mmol) in ether (1 L) and TEA (36 mL, 260 mmol) was cooled to −10° C. Trimethylacetyl chloride (31.8 mL, 260 mmol) was then added slowly and after stirring at −10° C. for 10 min, the reaction was allowed to warm to 10° C. over 1 h. The reaction was then recooled to −60° C.

To the above solution at −60° C. was added via a canula a solution of (S)-(−)-4-benzyl-2-oxazolidinone (45.8 g, 260 mmol) in THF (500 mL) which had been treated at −50° C. with 2.5 M n-butyl lithium (103 mL, 257 mmol) and aged at −50° C. for 45 min. The reaction was allowed to warm to rt over 16 h. The reaction was diluted with ether (1 L) and quenched with sat'd aqueous ammonium chloride (1 L). The layers were separated and the aqueous layer was reextracted with a second portion of ether. The organic layers were each washed twice with 2N hydrochloric acid, twice with 1N sodium hydroxide and brine, dried over sodium sulfate, combined and concentrated. The residue was purified by chromatography (20% ethyl acetate in hexanes) to give the two diastereomeric products, higher $R_f$ (18.4 g) and lower $R_f$ (17.7 g).

Step B2: (+)-trans-4-Methylene-2-phenylcyclopentanoic acid

A solution of 1-(S)-(((S)-(−)-4-benzyl-2-oxazolidin-1-yl)carbonyl)-3-methylene-2-(S)-phenylcyclopentane (higher $R_f$ product from Step B1) (20.9 g, 58 mmol) in a 3:1 mixture of THF:water (1 L) was cooled to 5° C. Hydrogen peroxide (30%, 39.5 mL, 350 mmol) and lithium hydroxide (4.85 g, 106 mmol) were added and the reaction was stirred for 3.5 h. The excess peroxide was quenched by dropwise addition of sodium sulfite (60 g) in water (1 L) over 1.5 h while maintaining the temperature below 5° C. After stirring for 2 additional hours, most of the THF was removed in vacuo and the aqueous layer was washed 3 times with methylene chloride. The aqueous layer was acidified to pH=2 with conc. HCl and reextracted twice with methylene chloride. The organic layers were washed with brine, dried and concentrated to give the (+) title product, $[\alpha]_D$=+100.5 (MeOH, c=0.207).

Step D: (+ and −)-trans-1-Hydroxymethyl-4-methylene-2-phenylcyclopentane

A solution of (+)-trans-4-methylene-2-phenylcyclopentanoic acid from Step C (4.15 g, 20.5 mmol) in THF (100 mL) under nitrogen was cooled to −7° C. and 1M LAH in THF (31 mL, 31 mmol) was added dropwise over 15. The reaction was allowed to warm to RT over 16 h. The excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title (+) product (3.93 g), $[\alpha]_D$=+50 (MeOH, c=0.20).

Similarly, the (−)-trans-4-methylene-2-phenylcyclopentanoic acid from Step C (4.23 g) was converted to the title (−) alcohol (3.75 g), $[\alpha]_D$=−51 (MeOH, c=0.2).

Step E: (+ and −)-trans-1-t-Butyldimethylsilyloxymethyl-4-oxo-2-phenylcyclopentane Using essentially the same procedure as in Example 20, Step D but substituting the chiral(+)-trans-1-hydroxymethyl-4-methylene-2-phenylcyclopentane from Step D (3.93 g, 21 mmol), the title (+) compound (5.6 g) was prepared, $[\alpha]_D$=+42.3 (MeOH, c=0.18).

Similarly, (−)-trans-1-hydroxymethyl-4-methylene-2-phenylcyclopentane from Step D (3.75 g) was converted to the title (−) alcohol (5.5 g), $[\alpha]_D$=−44.4 (MeOH, c=0.18).

Step F: (+ and −)-trans-1-Hydroxymethyl-4-oxo-2-phenylcyclopentane

A solution of (+)-trans-1-t-butyldimethylsilyloxymethyl-4-methylene-2-phenylcyclopentane from Step E (4.6 g, 15 mmol) in methanol (100 mL) was cooled to −70° C. in a dry-ice acetone bath and ozone was bubbled through until a blue color persisted which was discharged with a stream of nitrogen. Dimethylsulfide (10 mL) was added and water 15 min, the reaction was allowed to warm to RT over 16 h. Since by TLC (20% ethyl acetate in hexanes) indicated that there was significant loss of the silyl as well as dimethylketal formation, the methanol was mostly remove in vacuo.

The residue was diluted with water and treated with sulfuric acid (6 mL) and stirred for 2 h. The mixture was extracted twice with ethyl acetate and the organic layers were washed with brine (containing some sodium bicarbonate), dried over sodium sulfate, combined and concentrated. The residue was purified by FC (15–30% ethyl acetate in hexanes) to give the (+) title ketone/alcohol (2.87 g).

Similarly, (−)-trans-1-t-butyldimethylsilyloxymethyl-4-methylene-2-phenylcyclopentane from Step E (4.48 g) was converted to the title (−) ketone/alcohol (2.86 g).

Step G: 1-(R)-(N-(Methyl)-N-(t-butoxycarbonyl)amino)-3-(S)-(hydroxymethyl)-4-(S)-phenylcyclopentane (Higher $R_f$ isomer) and 1-(S)-(N-(Methyl)-N-(t-butoxycarbonyl)amino)-3-(S)-(hydroxymethyl)-4-(S)-phenylcyclopentane (Lower $R_f$ isomer)

Using essentially the same procedures as in Example 11, Steps A and B but starting with chiral(+)-trans-1-hydroxymethyl-4-oxo-2-phenylcyclopentane from Step F (1.19 g, 6.26 mmol) and using di-t-butyl dicarbonate in place of phenylsulfonyl chloride, the two chiral title C-1 isomeric products (260 mg higher, 215 mg lower, plus mix fractions) were obtained after FC (20% ethyl acetate in hexanes) and were the same as the racemic products from Example 15.

Step H: 1-(R)-(N-(Methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedures as in Example 11, Steps C and D but starting with 1-(R)-(N-(methyl)-N-(t-butoxycarbonyl)amino)-3-(S)-(hydroxymethyl)-4-(S)-phenylcyclopentane (Higher $R_f$ isomer) from Step G (257 mg, 0.84 mmol) and using 4-(N-(4-nitrobenzyloxycarbonyl)-N-(allyl)amino)piperidine hydrochloride, the title compound was obtained and was the same as the racemic product from Example 15, $[\alpha]_D$=+15.9 (MeOH, c=0.21).

MS (NH$_3$/ESI): m/z 607 (M+1).

EXAMPLE 30

1-(S)-(N-(Methyl)-N-(t-butoxycarbonyl)amino)-3-(R)-((4-(N-(4-nitrobenzyloxycarbonyl)-N-(allyl)amino)piperidin-1-yl)methyl)-4-(R)-phenylcyclopentane Step A: 1-(S)-(N-(Methyl)-N-(t-butoxycarbonyl)amino)-3-(R)-(hydroxymethyl)-4-(R)-phenylcyclopentane (Higher $R_f$ isomer) and 1-(R)-(N-(methyl)-N-(t-butoxycarbonyl)amino)-3-(R)-(hydroxymethyl)-4-(R)-phenylcyclopentane (Lower $R_f$ isomer)

Similar to Example 29, Step G, (−)-trans-1-hydroxymethyl-4-oxo-2-phenylcyclopentane from Example 29, Step F (1.16 g, 6.1 mmol) was converted to the chiral title C-1 epimers (330 mg higher, 180 mg lower, plus mixed fractions).

Step B: 1-(S)-(N-(Methyl)-N-(t-butoxycarbonyl)amino)-3-(R)-((4-(N-(4-nitrobenzyloxycarbonyl)-N-(allyl)amino)piperidin-1-yl)methyl)-4-(R)-phenylcyclopentane Similarly to Example 29, Step H, 1-(S)-(N-(methyl)-N-(t-butoxycarbonyl)amino)-3-(R)-(hydroxymethyl)-4-(R)-phenylcyclopentane (Higher $R_f$ isomer from Example 30, Step A) (330 mg, 6 mmol) was converted to the chiral title enantiomer (333 mg), $[\alpha]_D$=−18.7 (MeOH, c=0.225).

MS (NH$_3$/ESI): m/z 607 (M+1).

EXAMPLE 31

1-(S)-(N-(Methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedures as in Example 29, Step G and H, the lower $R_f$ C-1 epimer from Example 29, Step F (215 mg) was converted to the title compound (302 mg).

MS (NH$_3$/ESI): m/z 607 (M+1).

EXAMPLE 32

1-(R)-(N-(Methyl)-N-(t-butoxycarbonyl)amino)-3-(R)-((4-(N-(4-nitrobenzyloxycarbonyl)-N-(allyl)amino)piperidin-1-yl)methyl)-4-(R)-phenylcyclopentane Using essentially the same procedures as in Example 29, Step G and H, the lower $R_f$ C-1 epimer from Example 30, Step A (180 mg) was converted to the title compound (251 mg).

MS (NH$_3$/ESI): m/z 607 (M+1).

EXAMPLE 33

1-(S)-((t-Butoxycarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as Example 20, Step E–H, starting with (+)-trans-1-hydroxymethyl-4-oxo-2-phenylcyclopentane from Example 29, Step F (1.19 g, 6.3 mmol) and using the higher $R_f$ Boc/alcohol epimer (195 mg), the title compound (280 mg) was prepared.

MS (NH$_3$/ESI): m/z 593 (M+1).

EXAMPLE 34

1-(R)-((t-Butoxycarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as Example 20, Step E–H, (+)-trans-1-hydroxymethyl-4-oxo-2-phenylcyclopentane from Example 29, Step F (1.19 g, 6.3 mmol) and using the lower $R_f$ Boc/alcohol epimer (195 mg), the title compound (280 mg) was prepared.

MS (NH$_3$/ESI): m/z 593 (M+1).

EXAMPLE 35A 1-(R)-(N-(Methyl)-N-(methylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t- butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and methylsulfonyl chloride in Step B, the title compound was prepared.

MS (NH$_3$/ESI): m/z 585 (M+1).

EXAMPLE 35B 1-(R)-(N-(Methyl)-N-(phenylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and phenylsulfonyl chloride in Step B, the title compound was prepared.

MS (NH$_3$/ESI): m/z 647 (M+1).

EXAMPLE 35C 1-(R)-(N-(Methyl)-N-(phenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and benzoyl chloride in Step B, the title compound was prepared.

MS (NH$_3$/ESI): m/z 611 (M+1).

EXAMPLE 35D 1-(R)-(N-(Methyl)-N-(3-fluorophenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and 3-fluorobenzoyl chloride in Step B, the title compound was prepared.

MS (NH$_3$/ESI): m/z 629 (M+1).

EXAMPLE 35E 1-(R)-(N-(Methyl)-N-(4-fluorophenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and 4-fluorobenzoyl chloride in Step B, the title compound was prepared.

MS (NH$_3$/ESI): m/z 629 (M+1).

EXAMPLE 35F 1-(R)-(N-(Methyl)-N-(cyclohexylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and cyclohexanoyl chloride in Step B, the title compound was prepared.

MS (NH$_3$/ESI): m/z 617 (M+1).

EXAMPLE 35G 1-(R)-(N-(Methyl)-N-(dimethylaminocarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and dimethylcarbamoyl chloride in Step B, the title compound was prepared.

MS (NH$_3$/ESI): m/z 578 (M+1).

EXAMPLE 35H 1-(R)-(N-(Methyl)-N-(methylaminothiocarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and methyl isothiocyanate in Step B, the title compound was prepared.

MS (NH$_3$/ESI): m/z 580 (M+1).

EXAMPLE 35I 1-(R)-(N-(Methyl)-N-(benzylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 29, Step H in Step A and phenylacetyl chloride in Step B, the title compound was prepared.

MS (NH$_3$/ESI): m/z 625 (M+1).

EXAMPLE 36A 1-(S)-(N-(Methyl)-N-(methylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and methylsulfonyl chloride in Step B, the title compound was prepared.

MS (NH$_3$/ESI): m/z 585 (M+1).

EXAMPLE 36B 1-(S)-(N-(Methyl)-N-(phenylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t- butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and phenylsulfonyl chloride in Step B, the title compound was prepared.

MS (NH$_3$/ESI): m/z 647 (M+1).

EXAMPLE 36C 1-(S)-(N-(Methyl)-N-(phenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and benzoyl chloride in Step B, the title compound was prepared.

MS (NH$_3$/ESI): m/z 611 (M+1).

EXAMPLE 36D 1-(S)-(N-(Methyl)-N-(3-fluorophenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and 3-fluorobenzoyl chloride in Step B, the title compound was prepared.

MS (NH$_3$/ESI): m/z 629 (M+1).

EXAMPLE 36E 1-(S)-(N-(Methyl)-N-(4-fluorophenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and 4-fluorobenzoyl chloride in Step B, the title compound was prepared.

MS (NH$_3$/ESI): mtz 629 (M+1).

EXAMPLE 36F 1-(S)-(N-(Methyl)-N-(cyclohexylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and cyclohexanoyl chloride in Step B, the title compound was prepared.

MS (NH$_3$/ESI): m/z 617 (M+1).

EXAMPLE 36G 1-(S)-(N-(Methyl)-N-(dimethylaminocarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and dimethylcarbamoyl chloride in Step B, the title compound was prepared.

MS (NH$_3$/ESI): m/z 578 (M+1).

EXAMPLE 36H 1-(S)-(N-(Methyl)-N-(methylaminothiocarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and methyl isothiocyanate in Step B, the title compound was prepared.

MS (NH$_3$/ESI): m/z 580 (M+1).

EXAMPLE 36I 1-(S)-(N-(Methyl)-N-(benzylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-(N-(methyl)-N-(t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 31 in Step A and phenylacetyl chloride in Step B, the title compound was prepared.

MS (NH$_3$/ESI): m/z 625 (M+1).

EXAMPLE 37A 1-(S)-((Methylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and methylsulfonyl chloride in Step B, the title compound was prepared.

MS (NH$_3$/ESI): m/z 571 (M+1).

EXAMPLE 37B 1-(S)-((Phenylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)

amino)piperidin-1-yl)methyl)-4-(S)-phenylcyclopentane from Example 33 in Step A and phenylsulfonyl chloride in Step B, the title compound was prepared.

MS (NH$_3$/ESI): m/z 633 (M+1).

EXAMPLE 37C 1-(S)-((Phenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and benzoyl chloride in Step B, the title compound was prepared.

MS (NH$_3$/ESI): m/z 597 (M+1).

EXAMPLE 37D 1-(S)-((3-Fluorophenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and 3-fluorobenzoyl chloride in Step B, the title compound was prepared.

MS (NH$_3$/ESI): m/z 615 (M+1).

EXAMPLE 37E 1-(S)-((4-Fluorophenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and 4-fluorobenzoyl chloride in Step B, the title compound was prepared.

MS (NH$_3$/ESI): m/z 615 (M+1).

EXAMPLE 37F 1-(S)-((Cyclohexylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and cyclohexanoyl chloride in Step B, the title compound was prepared.

MS (NH$_3$/ESI): m/z 603 (M+1).

EXAMPLE 37G 1-(S)-((Dimethylaminocarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and dimethylcarbamoyl chloride in Step B, the title compound was prepared.

MS (NH$_3$/ESI): m/z 564 (M+1).

EXAMPLE 37H 1-(S)-((Methylaminothiocarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and methyl isothiocyanate in Step B, the title compound was prepared.

MS (NH$_3$/ESI): m/z 566 (M+1).

EXAMPLE 37I 1-(S)-((Benzylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(S)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 33 in Step A and phenylacetyl chloride in Step B, the title compound was prepared.

MS (NH$_3$/ESI): m/z 611 (M+1).

EXAMPLE 38A 1-(R)-((Methylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 34 in Step A and methylsulfonyl chloride in Step B, the title compound was prepared.

MS (NH$_3$/ESI): m/z 571 (M+1).

EXAMPLE 38B 1-(R)-((Phenylsulfonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-((t-butoxycarbonyl)amino)-3-(S)-((4-(N-(4-nitrobenzyloxycarbonyl)-N-(allyl)amino)piperidin-1-yl)methyl)-4-(S)-phenylcyclopentane from Example 34 in Step A and phenylsulfonyl chloride in Step B, the title compound was prepared.

MS (NH$_3$/ESI): m/z 633 (M+1).

EXAMPLE 38C 1-(R)-((Phenylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-((t-butoxycarbonyl)

amino)-3-(S)-((4-(N-(4-nitrobenzyloxycarbonyl)-N-(allyl) amino)piperidin-1-yl)methyl)-4-(S)-phenylcyclopentane from Example 34 in Step A and benzoyl chloride in Step B, the title compound was prepared.

MS (NH$_3$/ESI): m/z 597 (M+1).

EXAMPLE 38D 1-(R)-((3-Fluorophenylcarbonyl)amino)-3-(S)-((4-(N-(4-nitrobenzyloxycarbonyl)-N-(allyl)amino) piperidin-1-yl)methyl)-4-(S)-phenylcyclopentane Using essentially the same procedure as in Example 16, Step A and B but substituting 1-(R)-((t-butoxycarbonyl) amino)-3-(S)-((4-(N-(4-nitrobenzyloxycarbonyl)-N-(allyl) amino)piperidin-1-yl)methyl)-4-(S)-phenylcyclopentane from Example 34 in Step A and 3-fluorobenzoyl chloride in Step B, the title compound was prepared.

MS (NH$_3$/ESI): m/z 615 (M+1).

EXAMPLE 38E 1-(R)-((4-Fluorophenylcarbonyl)amino)-3-(S)-((4-(N-(4-nitrobenzyloxycarbonyl)-N-(allyl)amino) piperidin-1-yl)methyl)-4-(S)-phenylcyclopentane Using essentially the same procedure as in Example 16, Step A and B but substituting 1-(R)-((t-butoxycarbonyl) amino)-3-(S)-((4-(N-(4-nitrobenzyloxycarbonyl)-N-(allyl) amino)piperidin-1-yl)methyl)-4-(S)-phenylcyclopentane from Example 34 in Step A and 4-fluorobenzoyl chloride in Step B, the title compound was prepared.

MS (NH$_3$/ESI): m/z 615 (M+1).

EXAMPLE 38F 1-(R)-((Cyclohexylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-((t-butoxycarbonyl) amino)-3-(S)-((4-(N-(4-nitrobenzyloxycarbonyl)-N-(allyl) amino)piperidin-1-yl)methyl)-4-(S)-phenylcyclopentane from Example 34 in Step A and cyclohexanoyl chloride in Step B, the title compound was prepared.

MS (NH$_3$/ESI): m/z 603 (M+1).

EXAMPLE 38G 1-(R)-((Dimethylaminocarbonyl)amino)-3-(S)-((4-(N-(4-nitrobenzyloxycarbonyl)-N-(allyl)amino) piperidin-1-yl)methyl)-4-(S)-phenylcyclopentane Using essentially the same procedure as in Example 16, Step A and B but substituting 1-(R)-((t-butoxycarbonyl) amino)-3-(S)-((4-(N-(4-nitrobenzyloxycarbonyl)-N-(allyl) amino)piperidin-1-yl)methyl)-4-(S)-phenylcyclopentane from Example 34 in Step A and dimethylcarbamoyl chloride in Step B, the title compound was prepared.

MS (NH$_3$/ESI): m/z 564 (M+1).

EXAMPLE 38H 1-(R)-((Methylaminothiocarbonyl)amino)-3-(S)-((4-(N-(4-nitrobenzyloxycarbonyl)-N-(allyl)amino) piperidin-1-yl)methyl)-4-(S)-phenylcyclopentane Using essentially the same procedure as in Example 16, Step A and B but substituting 1-(R)-((t-butoxycarbonyl) amino)-3-(S)-((4-(N-(4-nitrobenzyloxycarbonyl)-N-(allyl) amino)piperidin-1-yl)methyl)-4-(S)-phenylcyclopentane from Example 34 in Step A and methyl isothiocyanate in Step B, the title compound was prepared.

MS (NH$_3$/ESI): m/z 566 (M+1).

EXAMPLE 38I 1-(R)-((Benzylcarbonyl)amino)-3-(S)-((4-(N-(4-nitrobenzyloxycarbonyl)-N-(allyl)amino)piperidin-1-yl)methyl)-4-(S)-phenylcyclopentane Using essentially the same procedure as in Example 16, Step A and B but substituting 1-(R)-((t-butoxycarbonyl) amino)-3-(S)-((4-(N-(4-nitrobenzyloxycarbonyl)-N-(allyl) amino)piperidin-1-yl)methyl)-4-(S)-phenylcyclopentane from Example 34 in Step A and phenylacetyl chloride in Step B, the title compound was prepared.

MS (NH$_3$/ESI): m/z 611 (M+1).

EXAMPLE 39

1-(RS and SR)-(N-(Benzenesulfonyl)-N-(phenyl) amino)-3-(SR)-((4-(N-(benzyloxycarbonyl)-N-(ethyl)amino)piperidin-1-yl)methyl)-4-(SR)-phenylcyclopentane hydrochloride salt The following example illustrates the use of a 4-sulfamylbenzoyl AM resin (Novabiochem, cat #01-64-0121) to prepare the title compound and is based on the procedures of G. W. Kenner, et al., *J. Chem. Soc., Chem. Comm.*, 1971, 636.

Step A: Loading of the resin with (+−)-trans-4-oxo-2-phenylcyclopentanoic acid

To a solution of (+−)-trans-4-oxo-2-phenylcyclopentanoic acid (2.35 g, 11.5 mmol) from Example 42, Step A and DMAP (70 mg, 0.57 mmol) in 1:1 methylene chloride:THF (23 mL) was added DIC (0.90 mL, 5.7 mmol). The reaction was aged at rt for 10 min and was then added to the resin (1.0 g, 1.15 mmol/g) which had been pre-treated with 1:1 methylene chloride:THF to swell the beads. DIPEA (1.0 mL, 5.7 mmol) was added and the reaction was gently mixed at rt for 3 h. The resin was filtered, washed with solvent and retreated with another aliquot of acid for 3 h. The resin was washed again and air dried before use in the next step.

Step B: Reductive amination with aniline

A solution of aniline (0.054 mL, 0.57 mmol) and acetic acid (0.033 mL, 0.57 mmol) in methylene chloride (1 mL) was added to the resin (50 mg, 0.057 mmol) from Step A. Sodium triacetoxyborohydride (0.122 g, 0.57 mmol) was added and the reaction was gently mixed at rt for 16 h. The resin was then washed with solvent and used in the next step.

Step C: Sulfonylation with benzenesulfonyl chloride

A solution of benzene sulfonyl chloride (0.051 mL, 0.4 mmol) in methylene chloride (1 mL) was added to the resin (50 mg, 0.057 mmol) from Step B. DIPEA (0.105 mL, 0.6 mmol) in methylene chloride (1 mL) was added and the reaction was gently mixed at rt for 16 h. The resin was then washed with solvent and used in the next step.

Step D: Activation and cleavage from the resin with an amine. 1-(RS and SR)-(N-(Benzenesulfonyl)-N-(phenyl) amino)-3-(SR)-((4-(N-(benzyloxycarbonyl)-N-(ethyl) amino)piperidin-1-yl)carbonyl)-4-(SR)-phenylcyclopentane TFA salt The resin from Step C (50 mg, 0.057 mmol) was treated twice with 1:1 2.0 M trimethylsilyldiazomethane in hexanes:THF (1 mL) for 2 h. The resin was washed with THF and then treated with 4-(N-(benzyloxycarbonyl)-N-(ethyl)

amino)piperidine (30 mg, 0.11 mmol) in THF (1 mL) at rt for 16 h. The resin was filtered off, the solution was evaporated under nitrogen and the residue was taken up in 70% acetonitrile in water. The sample was purified on a Gilson Combinatorial Chromatography system using a 9.4 mm×25 cm Zorbax SB-C18 column with a 0.1% TFA acetonitrile/water gradient. The fractions were collected based on the UV absorption and analyzed by mass spec to identify the product fractions. These were combined and evaporated to afford the title compound (4.1 mg).

MS (NH$_3$/ESI): m/z 666 (M+1).

Step E: Reduction of the amide with borane-dimethyl sulfide. 1-(RS and SR)-(N-(Benzenesulfonyl)-N-(phenyl) amino)-3-(SR)-((4-(N-(benzyloxycarbonyl)-N-(ethyl) amino)piperidin-1-yl)methyl)-4-(SR)-phenylcyclopentane hydrochloride salt A solution of 0.5 M borane-dimethyl sulfide in dioxane (0.25 mL) was added to the product of Step D and the reaction was heated at 50° C. for 3 h. The volatiles were removed in vacuo and the residue was taken up in a 1% HCl in methanol solution (1 mL). After 16 h at 50° C., HPLC/MS indicated that the reaction was complete and clean of impurities. The volatiles were removed in vacuo to give the title compound.

MS (NH$_3$/ESI): m/z 652 (M+1).

EXAMPLE 40

Using essentially the same procedure as in Example 39, but substituting the appropriate aniline or benzylamine in Step B, the following compounds 40A–E were prepared. The final products and/or penultimate amides were purified by HPLC and analyzed by HPLC/MS for purity and the correct molecular weights.

EXAMPLE 40A 1-(RS and SR)-(N-(Benzenesulfonyl)-N-(4-(2-methoxyphenyl)phenyl)amino)-3-(SR)-((4-(N-(benzyloxycarbonyl)-N-(ethyl)amino)piperidin-1-yl) methyl)-4-(SR)-phenylcyclopentane

EXAMPLE 40B 1-(RS and SR)-(N-(Benzenesulfonyl)-N-(3-methoxyphenyl)amino)-3-(SR)-((4-(N-(benzyloxycarbonyl)-N-(ethyl)amino)piperidin-1-yl) methyl)-4-(SR)-phenylcyclopentane

EXAMPLE 40C 1-(RS and SR)-(N-(Benzenesulfonyl)-N-(2-methylphenyl)amino)-3-(SR)-((4-(N-(benzyloxycarbonyl)-N-(ethyl)amino)piperidin-1-yl) methyl)-4-(SR)-phenylcyclopentane

EXAMPLE 40D 1-(RS and SR)-(N-(Benzenesulfonyl)-N-(I-naphthyl)amino)-3-(SR)-((4-(N-(benzyloxycarbonyl)-N-(ethyl)amino)piperidin-1-yl) methyl)-4-(SR)-phenylcyclopentane

EXAMPLE 40E 1-(RS and SR)-(N-(Benzenesulfonyl)-N-(benzyl) amino)-3-(SR)-((4-(N-(benzyloxycarbonyl)-N-(ethyl)amino)piperidin-1-yl)methyl)-4-(SR)-phenylcyclopentane

EXAMPLE 41

Using essentially the same procedure as in Example 39, but substituting methylamine in Step B and the appropriate substituted sulfonyl chloride in Step C, the following compounds 41A–K were prepared. The final products and penultimate amides were purified by HPLC and analyzed by HPLC/MS for purity and the correct molecular weights.

EXAMPLE 41A 1-(RS and SR)-(N-(Benzenesulfonyl)-N-(methyl) amino)-3-(SR)-((4-(N-(benzyloxycarbonyl)-N-(ethyl)amino)piperidin-1-yl)methyl)-4-(SR)-phenylcyclopentane

EXAMPLE 41B 1-(RS and SR)-(N-(1-Naphthylsulfonyl)-N-(methyl) amino)-3-(SR)-((4-(N-(benzyloxycarbonyl)-N-(ethyl)amino)piperidin-1-yl)methyl)-4-(SR)-phenylcyclopentane

EXAMPLE 41C 1-(RS and SR)-(N-(2-Naphthylsulfonyl)-N-(methyl) amino)-3-(SR)-((4-(N-(benzyloxycarbonyl)-N-(ethyl)amino)piperidin-1-yl)methyl)-4-(SR)-phenylcyclopentane

EXAMPLE 41D 1-(RS and SR)-(N-(3-Chlorobenzenesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41E 1-(RS and SR)-(N-(4-Chlorobenzenesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41F 1-(RS and SR)-(N-(2-Chlorobenzenesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41G 1-(RS and SR)-(N-(2-(1-Naphthyl)ethylsulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41H 1-(RS and SR)-(N-(4-t-Butylbenzenesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41I 1-(RS and SR)-(N-(4-Trifluoromethoxybenzenesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41J 1-(RS and SR)-(N-(Methanesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 41K 1-(RS and SR)-(N-(3,4-Dichlorobenzenesulfonyl)-N-(methyl)amino)-3-(SR)-((4-(N-(benzyloxycarbonyl)-N-(ethyl)amino)piperidin-1-yl)methyl)-4-(SR)-phenylcyclopentane

EXAMPLE 42

1-(RS or SR)-(N-(Methyl)-N-(cyclohexyl)amino)-3-(SR)-((4-(N-(benzyloxycarbonyl)-N-(ethyl)amino)piperidin-1-yl)methyl)-4-(SR)-phenylcyclopentane TFA salt Step A: (+−)-trans-4-Oxo-2-phenylcyclopentanoic acid A solution of 1-(SR)-3-methylene-4-(SR)-phenylcyclopentanoic acid (84.8 g, 0.42 mol) from Example 20, Step B in methanol (2.5 L) was cooled to −70° C. in a dry-ice acetone bath. Ozone was bubbled through the solution until the blue color persisted. Excess ozone was removed with a stream of nitrogen and dimethyl sulfide (125 mL, 1.68 mol) was added. The mixture was then allowed to warm to rt over 16 h. Most of the methanol was removed in vacuo and the residue was taken up in ethyl acetate and washed twice with water and brine, dried over sodium sulfate and concentrated. The residue was triturated with hexanes and the solid was filtered and dried to afford the title compound (61.4 g).

Step B: 3-(SR)-((4-(N-(Benzyloxycarbonyl)-N-(ethyl)amino)piperidin-1-yl)carbonyl)-4-(SR))-phenylcyclopentan-1-one To a solution of (+−)-trans-4-oxo-2-phenylcyclopentanoic acid (0.20 g, 0.1 mmol) and 4-(N-(benzyloxycarbonyl)-N-(ethyl)amino)piperidine (0.36 g, 0.12 mmol) in methylene chloride (12 mL) was added EDC (0.225 g, 0.12 mmol), DIPEA (0.205 mL, 0.12 mmol) and a cat. amount of DMAP. The reaction was stirred a rt for 2 h and was then diluted with methylene chloride and washed with 1N HCl, 1N NaOH and brine, dried over sodium sulfate and evaporated to dryness. The sample was essentially clean product by HPLC/MS.

Step C: 1-(RS and SR)-(N-(Methyl)-N-(cyclohexyl)amino)-3-(SR)-((4-(N-(benzyloxycarbonyl)-N-(ethyl)amino)piperidin-1-yl)carbonyl)-4-(SR)-phenylcyclopentane To a solution of 3-(SR)-((4-(N-(benzyloxycarbonyl)-N-(ethyl)amino)piperidin-1-yl)carbonyl)-4-(SR)-phenylcyclopentan-1-one (0.030 g, 0.067 mmol) from Step B and N-methylaminocyclohexane (0.076 mL, 0.67 mmol) in 1,2-dichloroethane (3 mL) was added acetic acid (0.038 mL, 0.67 mmol) and sodium triacetoxyborohydride (0.142 g, 0.67 mmol). The reaction was stirred at rt for 16 h and then diluted with methylene chloride and quenched with 1N NaOH. The mixture was washed with 1N NaOH, 1N HCl and brine, dried over sodium sulfate and evaporated to dryness. The sample was purified by HPLC and the fractions containing the title compound by HPLC/MS were combined and evaporated.

Step D: 1-(RS and SR)-(N-(Methyl)-N-(cyclohexyl)amino)-3-(SR)-((4-(N-(benzyloxycarbonyl)-N-(ethyl)amino)piperidin-1-yl)methyl)-4-(SR)-phenylcyclopentane TFA salt A solution of 1-(RS and SR)-(N-(methyl)-N-(cyclohexyl)amino)-3-(SR)-((4-(N-(benzyloxycarbonyl)-N-(ethyl)amino)piperidin-1-yl)carbonyl)-4-(SR)-phenylcyclopentane obtained in Step C and 2M borane-dimethyl sulfide in THF (0.027 mL, 0.054 mmol) in dioxane (0.6 mL) was heated at 50° C. for 3 h. The volatiles were removed under a stream of nitrogen and the residue was taken up in 1% HCl in methanol (1 mL) and heated at 50° C. for 16 h. The volatiles were removed in vacuo to dryness. The residue was purified by HPLC during which the 2 diastereomers at C-1 were separated. The fractions containing the title compounds by HPLC/MS were combined and evaporated.

EXAMPLE 43

Using essentially the same procedure as in Example 42, but substituting a primary cycloalkylamine or substituted cycloalkylamine in Step C, the following C-1 amino compounds 43A–I were prepared. The final products and penultimate amides were each purified by HPLC and analyzed by HPLC/MS for purity and the correct molecular weights. In these cases, the C-1 diastereomers were not separated.

EXAMPLE 43A 1-(RS and SR)-(Cyclohexylamino)-3-(SR)-((4-(N-(benzyloxycarbonyl)-N-(ethyl)amino)piperidin-1-yl)methyl)-4-(SR)-phenylcyclopentane

EXAMPLE 43B 1-(RS and SR)-(2-(Cyclohexyl)cyclohexylamino)-3-(SR)-((4-(N-(benzyloxycarbonyl)-N-(ethyl)amino)piperidin-1-yl)methyl)-4-(SR)-phenylcyclopentane

EXAMPLE 43C 1-(RS and SR)-(3,3,5-Trimethylcyclohexylamino)-3-(SR)-((4-(N-(benzyloxycarbonyl)-N-(ethyl)amino)piperidin-1-yl)methyl)-4-(SR)-phenylcyclopentane

EXAMPLE 43D 1-(RS and SR)-(4-t-Butylcyclohexylamino)-3-(SR)-((4-(N-(benzyloxycarbonyl)-N-(ethyl)amino)piperidin-1-yl)methyl)-4-(SR)-phenylcyclopentane

EXAMPLE 43E 1-(RS and SR)-(4-Phenylcyclohexylamino)-3-(SR)-((4-(N-(benzyloxycarbonyl)-N-(ethyl)amino)piperidin-1-yl)methyl)-4-(SR)-phenylcyclopentane

EXAMPLE 43F 1-(RS and SR)-(spiro(cyclohexyl-1,4'-cyclohex-1'-yl)amino)-3-(SR)-((4-(N-(benzyloxycarbonyl)-N-(ethyl)amino)piperidin-1-yl)methyl)-4-(SR)-phenylcyclopentane

EXAMPLE 43G 1-(RS and SR)-(Cyclopentylamino)-3-(SR)-((4-(N-(benzyloxycarbonyl)-N-(ethyl)amino)piperidin-1-yl)methyl)-4-(SR)-phenylcyclopentane

EXAMPLE 43H 1-(RS and SR)-(Cyclopropylamino)-3-(SR)-((4-(N-(benzyloxycarbonyl)-N-(ethyl)amino)piperidin-1-yl)methyl)-4-(SR)-phenylcyclopentane

EXAMPLE 43I 1-(RS and SR)-(Cycloheptylamino)-3-(SR)-((4-(N-(benzyloxycarbonyl)-N-(ethyl)amino)piperidin-1-yl)methyl)-4-(SR)-phenylcyclopentane

EXAMPLE 44

1-(RS and SR)-(N-(Acetyl)-N-(cyclohexyl)amino)-3-(SR)-((4-(N-(benzyloxycarbonyl)-N-(ethyl)amino)piperidin-1-yl)methyl)-4-(SR)-phenylcyclopentane To a solution of 1-(RS and SR)-(cyclohexylamino)-3-(SR)-((4-(N-(benzyloxycarbonyl)-N-(ethyl)amino)piperidin-1-yl)methyl)-4-(SR)-phenylcyclopentane (prepared as in Example 43A) in methylene chloride (2 mL) was added acetic anhydride (0.17 mL, 1.67 mmol) and pyridine (0.17 mL, 2 mmol). The reaction was stirred at rt for 16 h. It was then diluted with methylene chloride and quenched with 1N NaOH. The mixture was washed with 1N NaOH and brine, dried over sodium sulfate and evaporated to dryness. The sample was purified by HPLC and the fractions containing the title compound by HPLC/MS were combined and evaporated.

EXAMPLE 45

Using essentially the same procedures as in Example 42 and 44, but substituting a cycloalkylamine or substituted cycloalkylamine in Example 42, Step C and acetic anhydride, methanesulfonyl chloride or methyl chloroformate in Example 44, the following compounds 45A–L were prepared. In the carbamate cases, the acylation reaction with methyl chloroformate could also be done prior to the borane-dimethyl sulfide reduction step. The final products and penultimate amides were each purified by HPLC and analyzed by HPLC/MS for purity and the correct molecular weights. In these cases, the C-1 diastereomers were not separated.

EXAMPLE 45A 1-(RS and SR)-(N-(Methoxycarbonyl)-N-(cyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45B 1-(RS and SR)-(N-(Methanesulfonyl)-N-(cyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45C 1-(RS and SR)-(N-(Acetyl)-N-(2-cyclohexylcyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45D 1-(RS and SR)-(N-(Methoxycarbonyl)-N-(2-cyclohexylcyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45E 1-(RS and SR)-(N-(Acetyl)-N-(3,3,5-trimethylcyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45F 1-(RS and SR)-(N-(Methoxycarbonyl)-N-(3,3,5-trimethylcyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45G 1-(RS and SR)-(N-(Acetyl)-N-(4-t-butylcyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45H 1-(RS and SR)-(N-(Methanesulfonyl)-N-(4-phenylcyclohexyl)amino)-3-(SR)-((4-(N-(benzyloxycarbonyl)-N-(ethyl)amino)piperidin-1-yl)methyl)-4-(SR)-phenylcyclopentane

EXAMPLE 45I 1-(RS and SR)-(N-(Methanesulfonyl)-N-(spiro(cyclohexyl-1,4'-cyclohex-1'-yl)amino)-3-(SR)-((4-(N-(benzyloxycarbonyl)-N-(ethyl)amino)piperidin-1-yl)methyl)-4-(SR)-phenylcyclopentane

EXAMPLE 45J 1-(RS and SR)-(N-(Methanesulfonyl)-N-(cyclopropyl)amino)-3-(SR)-((4-(N-(benzyloxycarbonyl)-N-(ethyl)amino)piperidin-1-yl)methyl)-4-(SR)-phenylcyclopentane

EXAMPLE 45K 1-(RS and SR)-(N-(Methanesulfonyl)-N-(cycloheptyl)amino)-3-(SR)-((4-(N-(benzyloxycarbonyl)-N-(ethyl)amino)piperidin-1-yl)methyl)-4-(SR)-phenylcyclopentane

EXAMPLE 45L 1-(RS and SR)-(N-(Methanesulfonyl)-N-(cyclopentyl)amino)-3-(SR)-((4-(N-(benzyloxycarbonyl)-N-(ethyl)amino)piperidin-1-yl)methyl)-4-(SR)-phenylcyclopentane

EXAMPLE 46

Using essentially the same procedure as in Example 42, but substituting a secondary cyclic amine in Step C, the following compounds 46A–C were prepared and afforded the correct MS results after automated HPLC purification.

EXAMPLE 46A 1-(RS and SR)-(Decahydroquinolin-1-yl)-3-(SR)-((4-(N-(benzyloxycarbonyl)-N-(ethyl)amino)piperidin-1-yl)methyl)-4-(SR)-phenylcyclopentane

EXAMPLE 46B 1-(RS and SR)-(Duodecahydrocarbazol-1-yl)-3-(SR)-((4-(N-(benzyloxycarbonyl)-N-(ethyl)amino)piperidin-1-yl)methyl)-4-(SR)-phenylcyclopentane

EXAMPLE 46C 1-(RS and SR)-(1-Aza-2-methyl-6-hydroxy-[4.4.0]-bicyclodecan-1-yl)-3-(SR)-((4-(N-(benzyloxycarbonyl)-N-(ethyl)amino)piperidin-1-yl)methyl)-4-(SR)-phenylcyclopentane

EXAMPLE 47

1-(RS and SR)-(cis-1,3-Diaza-2-oxo-[3.4.0]-bicyclononan-1-yl)-3-(SR)-((4-(N-(benzyloxycarbonyl)-N-(ethyl)amino)piperidin-1-yl)methyl)-4-(SR)-phenylcyclopentane Step A: 1-(RS and SR)-(cis-(2-aminocyclohexyl)amino)-3-(SR)-((4-(N-(benzyloxycarbonyl)-N-(ethyl)amino)piperidin-1-yl)carbonyl)-4-(SR)-phenylcyclopentane Using essentially the same procedures as in Example 42, Steps A–C, but substituting cis-1,2-diaminocyclohexane in Step C, the title compound was prepared.

Step B: 1-(RS and SR)-(cis-1,3-Diaza-2-oxo-[3.4.0]-bicyclononan-1-yl)-3-(SR)-((4-(N-(benzyloxycarbonyl)-N-(ethyl)amino)piperidin-1-yl)carbonyl)-4-(SR)-phenylcyclopentane The product from Step A was taken up in methylene chloride (2 mL) and cooled to −10° C. DIPEA (0.039 mL, 0.22 mmol) was added followed by 1.9M phosgene in toluene (0.070 mL, 0.11 mmol). The reaction was stirred at rt for 30 min and were then diluted with methylene chloride and quenched with 1N NaOH. The layers were separated and the organic layer was washed with brine, dried and evaporated. The residue was purified by HPLC to give the title compound.

Step C: 1-(RS and SR)-(cis-1,3-Diaza-2-oxo-[3.4.0]-bicyclononan-1-yl)-3-(SR)-((4-(N-(benzyloxycarbonyl)-N-(ethyl)amino)piperidin-1-yl)methyl)-4-(SR)-phenylcyclopentane The product from Step B was treated with 2M borane-dimethyl sulfide in THF (0.111 mL, 0.22 mmol) in dioxane (2 mL) at 50° C. for 16 h. The reaction was evaporated and the residue was taken up in 1% TFA in methanol (2 mL) and warmed at 50° C. for 16 h. The volatiles were removed under a stream of nitrogen to give the title compound which was essentially pure by HPLC/MS.

EXAMPLE 48

Using essentially the same procedures as in Example 47, but substituting the appropriate diamine in Step A, the following compounds 48A–C were prepared. The final products and/or penultimate amides were each purified by HPLC and analyzed by HPLC/MS for purity and the correct molecular weights. In these cases, the C-1 diastereomers were not separated.

EXAMPLE 48A 1-(RS and SR)-(trans-1,3-Diaza-2-oxo-[3.4.0]-bicyclononan-1-yl)-3-(SR)-((4-(N-(benzyloxycarbonyl)-N-(ethyl)amino)piperidin-1-yl)methyl)-4-(SR)-phenylcyclopentane

EXAMPLE 48B 1-(RS and SR)-(3-Aza-4-methyl-1-oxa-2-oxo-[3.3.0]-bicyclooctan-3-yl)-3-(SR)-((4-(N-(benzyloxycarbonyl)-N-(ethyl)amino)piperidin-1-yl)methyl)-4-(SR)-phenylcyclopentane

EXAMPLE 48C 1-(RS and SR)-(Spiro(cyclopentyl-1,3'-(2'-oxazolidon-3-yl))-3-(SR)-((4-(N-(benzyloxycarbonyl)-N-(ethyl)amino) piperidin-1-yl)methyl)-4-(SR)-phenylcyclopentane

EXAMPLE 49

1-(RS and SR)-(cis-1,3-Diaza-2-thia-2,2-dioxo-[3.4.0]-bicyclononan-1-yl)-3-(SR)-((4-(N-(benzyloxycarbonyl)-N-(ethyl)amino)piperidin-1-yl)methyl)-4-(SR)-phenylcyclopentane Using essentially the same procedures as in Example 47, but substituting cis-1,2-diaminocyclohexane in Step A and substituting sulfonyl chloride in Step B, the title compound was prepared. The final product and penultimate amide were each purified by HPLC and analyzed by HPLC/MS for purity and the correct molecular weights. In this case, the C-1 diastereomers were not separated.

EXAMPLE 50

1-(RS)-(N-(Benzoyl)-N-(methyl)amino)-3-(SR)-((4-(N-(benzyloxycarbonyl)-N-(ethyl)amino)piperidin-1-yl)methyl)-4-(SR)-phenylcyclopentane TFA salt Step A: Methyl 1-(SR)-4-((RS and SR)-(N-(methyl))amino)-2-(SR)-phenylcyclopentanoate Methyl(+−)-trans-4-oxo-2-phenylcyclopentanoate (6.4 g, 29.3 mmol) from Example 1, Step B, (or ozonolysis of methyl(+−)-trans-4-meyhylene-2-phenylcyclopentane from Example 20, Step A as in Example 42, Step A) methylamine (2M in tetrahydrofuran, 16.4 mL, 32.8 mmol) and acetic acid (1.87 mL, 32.7 mmol) were combined in 1,2-dichloroethane (150 mL). Sodium triacetoxyborohydride (6.95 g, 32.8 mmol) was added in one portion to the vigorously stirred solution. After 18 hours at ambient temperature, the suspension was diluted with dichloromethane (100 mL) and vigorously stirred as the pH was adjusted to pH 10–11 with 1N NaOH. The layers were separated and the organic layers were washed twice with brine, dried over sodium sulfate and concentrated to afford the crude title compound (5.8 g) which was essentially the same as Example 11, Step A.

Step B: Methyl 1-(SR)-4-(RS and SR)-(N-(methyl)-N-(benzoyl)amino)-2-(SR)-phenylcyclopentanoate Methyl 1-(SR)-4-((RS and SR)-(N-(methyl))amino)-2-(SR)-phenylcyclopentanoate (5.8g, 24.9 mmol) from Step A was dissolved in dichloromethane (100 mL). Benzoyl chloride (3.5 mL, 30.1 mmol) and N,N-diisopropylethylamine (10.4 mL, 59.7 mmol) were added sequentially. After 3 hours, the organic layers were washed sequentially with 1N NaOH, 1N HCl and brine, then dried over sodium sulfate and concentrated to afford the crude title compound (4.4 g) which was essentially the same as Example 11, Step B.

Step C: 1-(RS)-(N-(Methyl)-N-(benzoyl)amino)-3-(SR)-(hydroxymethyl)-4-(SR)-phenylcyclopentane (Higher $R_f$ isomer) and 1-(SR)-(N-(methyl)-N-(benzoyl)amino)-3-(SR)-(hydroxymethyl)-4-(SR)-phenylcyclopentane (Lower $R_f$ isomer)

Methyl 1-(SR)-4-(RS and SR)-(N-(methyl)-N-(benzoyl)amino)-2-(SR)-phenylcyclopentanoate (4.4 g, 13.0 mmol) from Step B was dissolved in tetrahydrofuran (15 mL) and chilled to −10° C. Lithium borohydride (2M in THF, 13 mL, 26 mmol) was added slowly via syringe and the bath was removed. After 24 hours, the reaction was quenched by the cautious addition of 1N HCl. The organic layers were partitioned between ethyl ether and water and the layers were separated. The organic layers were washed sequentially with 1N NaOH and brine, then dried over sodium sulfate and concentrated. The diastereomers were separated using a Biotage Flash 40 chromatography apparatus. A gradient of 50% ethyl acetate in hexanes increasing to 60% ethyl acetate was used to elute the compounds. The higher $R_f$ diastereomer weighed 1.26 g and the lower diastereomer weighed 2.0 g. The remaining steps of this Example were performed using the higher separated diastereomer) which was the same as Example 11, Step C.

Step D: 1-(RS)-(N-(Methyl)-N-(benzoyl)amino)-3-(SR)-(formyl)-4-(SR)-phenylcyclopentane (Higher $R_f$ isomer)

Oxalyl chloride (0.884 mL, 10.2 mmol) was dissolved in dichloromethane (30 mL) and chilled to −78°. Dimethylsulfoxide (1.44 mL, 10.3 mmol) was added slowly and the solution was aged 15 minutes. A solution of 1-(RS)-(N-(methyl)-N-(benzoyl)amino)-3-(SR)-(hydroxymethyl)-4-(SR)-phenylcyclopentane (1.26 g, 4.1 mmol), the higher $R_f$ isomer from Step C, in methylene chloride (3 mL) was added slowly and the solution was aged for one hour. N,N-diisopropylethylamine (7.09 mL, 40.7 mmol) was added to the solution. After aging 10 minutes at −78°, the bath was removed and the solution was warmed to ambient temperature over one hour. The organic layers were washed sequentially with 1N HCl, water and brine, then dried over sodium sulfate and concentrated to afford the crude title compound which was essentially the same as Example 11, Step D.

Step E: 1-(RS)-(N-(Methyl)-N-(benzoyl)amino)-3-(SR)-((4-(N-(benzyloxycarbonyl)-N-(ethyl)amino)piperidin-1-yl)methyl)-4-(SR)-phenylcyclopentane hydrochloride salt To a 13×100 mm threaded vial was added 4-(N-(benzyloxycarbonyl)-N-(ethyl)amino)piperidine TFA salt (0.093 mmol). A solution of 1-(RS)-(N-(methyl)-N-(benzoyl)amino)-3-(SR)-(formyl)-4-(SR)-phenylcyclopentane (19 mg, 0.062 mmol) from Step D (derived from the higher $R_f$ isomer in Step C) and acetic acid (0.006 mL, 0.1 mmol) in 1,2-dichloroethane (1 mL) was added to the vial. Sequentially, N,N-diisopropylethylamine (0.022 mL, 0.126 mmol) and a solution of sodium triacetoxyborohydride (26 mg, 0.123 mmol) in 1,2-dichloroethane (2 mL) were added. The vial was sealed with a septum cap, gently shaken and stored at ambient temperature. After 18 hours, solvent was removed by a stream of warm nitrogen and the residue was redissolved in 80% acetonitrile in water. The sample was purified on a Gilson Combinatorial Chromatography system using a 9.4 mm×25 cm Zorbax SB-C18 column. Fractions were collected based on the UV absorption and analyzed by mass spec to identify the title compound fractions. These were combined and evaporated.

MS (NH$_3$/ESI): m/z 554 (M+1).

EXAMPLE 51

Using essentially the same procedures as in Example 50, Step E, but using each of a 7×10 matrix of individual piperidines in Step E, a library of 70 racemic samples with the following R and R' substitutions were prepared as the separated 1,3-trans diastereomers at the cyclopentyl C-1 position. Each sample was purified on a Gilson Combinatorial Chromatography system using a 9.4 mm×25 cm Zorbax SB-C18 column. Fractions were collected based on the UV absorption and analyzed by mass spec to identify the title compound fractions. These were combined and evaporated. The 70 piperidines were each individually prepared as described below in Procedure 10.

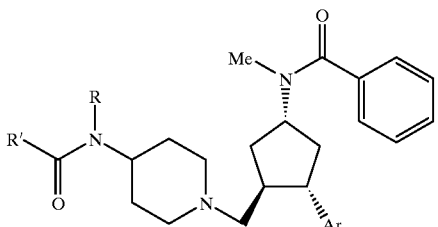

R=

Methyl
Ethyl
n-Propyl
n-Butyl
Allyl
Cyclopropylmethyl
2-Methylcycloprop-1-yl

R'=

Benzyloxy
4-Nitrobenzyloxy
2-Phenyleth-1-yloxy
2-(4-Nitrophenyl)eth-1-yloxy
Benzylamino
4-Nitrobenzylamino
2-Phenyleth-1-yl
2-(4-Nitrophenyl)eth-1-yl
Phenoxymethyl
4-Nitrophenoxymethyl

EXAMPLE 52

Using essentially the same procedures as in Example 50 and 51, but substituting the lower $R_f$ isomer from Example 50, Step C, a library of 70 racemic compounds with the following R and R' substitutions were prepared as the separated 1,3-cis diastereomers at the cyclopentyl C-1 position. Each sample was purified on a Gilson Combinatorial Chromatography system using a 9.4 mm×25 cm Zorbax SB-C18 column. Fractions were collected based on the UV absorption and analyzed by mass spec to identify the title compound fractions. These were combined and evaporated. The 70 piperidines were each individually prepared as described below in Procedure 10.

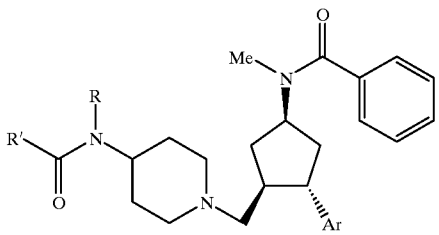

R=

Methyl
Ethyl
n-Propyl
n-Butyl
Allyl
Cyclopropylmethyl
2-Methylcycloprop-1-yl

R'=

Benzyloxy
4-Nitrobenzyloxy
2-Phenyleth-1-yloxy
2-(4-Nitrophenyl)eth-1-yloxy
Benzylamino
4-Nitrobenzylamino
2-Phenyleth-1-yl
2-(4-Nitrophenyl)eth-1-yl
Phenoxymethyl
4-Nitrophenoxymethyl

EXAMPLE 53

Using essentially the same procedures as in Example 50 and 51, but substituting cyclohexylamine in Example 50, Step A, substituting methyl chloroformate in Step B, using a mixture of isomers from Step C in Step D and using a 7×10 matrix of piperidines in Step E, a library of 70 racemic compounds with the following R and R' substitutions were prepared as a mixture of isomers at the cyclopentyl C-1 position. Each sample was purified on a Gilson Combinatorial Chromatography system using a 9.4 mm×25 cm Zorbax SB-C18 column. Fractions were collected based on the UV absorption and analyzed by mass spec to identify the title compound fractions. These were combined and evaporated. The 70 piperidines were each individually prepared as described below in Procedure 10.

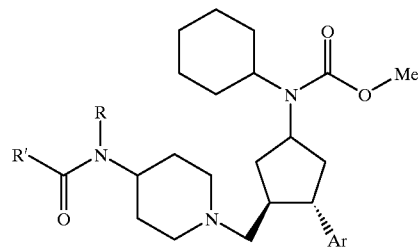

R=

Methyl
Ethyl
n-Propyl
n-Butyl
Allyl
Cyclopropylmethyl
2-Methylcycloprop-1-yl

R'=

Benzyloxy
4-Nitrobenzyloxy
2-Phenyleth-1-yloxy
2-(4-Nitrophenyl)eth-1-yloxy
Benzylamino
4-Nitrobenzylamino
2-Phenyleth-1-yl
2-(4-Nitrophenyl)eth-1-yl
Phenoxymethyl
4-Nitrophenoxymethyl

EXAMPLE 54

1-(RS and/or SR)-(N-(Methyl)-N-(benzoyl)amino)-3-(SR)-((4-(N-(4-nitrobenzyloxycarbonyl)-N-(allyl)amino)piperidin-1-yl)methyl)-4-(SR)-(3-thienyl) cyclopentane hydrochloride salt

Step A: Methyl 3-(3-thienyl)acrylate

A suspension of potassium t-butoxide (61.5 g, 0.55 mol) in THF (800 mL) was cooled in an ice bath and trimethylphosphonoacetate (98 mL, 0.60 mol) in THF (100 mL) was slowly added. After 45 min, thiophene 3-carboxaldehyde (50 mL, 0.55 mol) in THF (100 mL) was slowly added while stirred in the ice bath. The mixture was allowed to warm to rt and stirred for 16 h. The reaction was quenched with 5% sulfuric acid (300 mL) and extracted twice with ether. The organic layers were each washed with brine, dried over magnesium sulfate, combined and concentrated. The residue was purified by FC (10% ethyl acetate in hexanes) and then crystallized from hexanes to give the title compound (71.3 g).

$^1$H-NMR (500 MHz, CDCl$_3$): δ 3.77 (s, 3H), 6.25 (d, 1H, J=15.5 Hz), 7.26 (m, 1H), 7.30 (m, 1H), 7.46 (m, 1H), 7.66 (d, 1H, J=15.5 Hz).

$^{13}$C NMR (CDCl$_3$): δ 51.43, 117.27, 124.98, 126.80, 127.98, 137.34, 138.13, 167.42

Step B: Methyl(+−)-trans-4-methylene-2-(3-thienyl)cyclopentanoate

A mixture of methyl 3-(3-thienyl)acrylate (10.0 g, 59.5 mmol), tetrakis(triphenylphosphine)palladium(0) (5.15 g, 5.6 mmol), 1,2-bis(diphenylphosphino)ethane (1.35 g, 3.4 mmol) and 2-((trimethylsilyl)methyl)-2-propen-1-yl acetate (20 g, 107 mmol) in THF (125 mL) under argon was heated to reflux for 24 h. The volatiles were then removed in vacuo and the residue was purified by FC (5% ethyl acetate in hexanes) to afford the title compound (11.4 g).

MS (CI) m/e 222 (M$^+$).

Step C: (+−)-trans-1-Hydroxymethyl-4-methylene-2-(3-thienyl)cyclopentane

To a solution of methyl(+−)-trans-4-methylene-2-(3-thienyl)cyclopentanoate (6.0 g, 27 mmol) prepared as in Step B in THF (70 mL) under nitrogen and cooled to −10° C. was added dropwise over 15 min 1M lithium aluminum hydride (LAH) in THF (54 mL). After 1 h, the bath was removed and the reaction was stirred at rt for 3 h. The reaction was cooled in an ice/methanol bath and the excess LAH was quenched by dropwise addition of water/1N potassium hydroxide/water and the salts were removed by filtration through celite. The filtrate was then poured into dilute aq. HCl. The mixture was extracted twice with ether and the organic layers were washed with brine, dried over sodium sulfate, combined and concentrated to afford the crude title product (4.09 g).

$^1$H-NMR (500 MHz, CDCl$_3$): δ 2.21–2.30 (m, 2H), 2.42–2.53 (m, 2H), 2.68 (m, 1H), 2.77 (m, 1H), 3.03 (m, 1H), 3.49 and 3.65 (ABX, 2H, J$_{AB}$=11.0 Hz, J$_{AX}$=6.5 Hz, J$_{BX}$=4.5 Hz), 4.92 (br s, 1H).

$^{13}$C NMR (CDCl$_3$): δ 36.0, 41.49, 42.91, 49.11, 64.69, 105.90, 119.72, 125.63, 126.61, 144.84, 149.78.

MS (ESI) m/e 195 (M$^+$+1).

Step D: (+−)-trans-1-Hydroxymethyl-4-oxo-2-(3-thienyl)cyclopentane

Using essentially the same procedures as in Example 29, Steps E and F, but substituting (+−)-trans-1-hydroxymethyl-4-methylene-2-(3-thienyl)cyclopentane from Step C, the title compound can be obtained.

Step E: 1-(RS and/or SR)-(N-(Methyl)-N-(t-butoxycarbonyl)amino)-3-(SR)-((4-(N-(4-nitrobenzyloxycarbonyl)-N-(allyl)amino)piperidin-1-yl)methyl)-4-(SR)-(3-thienyl)cyclopentane Using essentially the same procedures as in Example 29, Steps G and H, but substituting (+−)-trans-1-hydroxymethyl-4-oxo-2-(3-thienyl)cyclopentane from Step D, the title compound(s) can be obtained.

Step F: 1-(RS and/or SR)-(N-(Methyl)-N-(benzoyl)amino)-3-(SR)-((4-(N-(4-nitrobenzyloxycarbonyl)-N-(allyl)amino)piperidin-1-yl)methyl)-4-(SR)-(3-thienyl)cyclopentane hydrochloride salt Using essentially the same procedures as in Example 16, Steps A and B, but substituting 1-(RS and/or SR)-(N-(methyl)-N-(t-butoxycarbonyl)amino)-3-(SR)-((4-(N-(4-nitrobenzyloxycarbonyl)-N-(allyl)amino)piperidin-1-yl)methyl)-4-(SR)-(3-thienyl)cyclopentane from Step E, the title compound(s) (or other substituted acyl or sulfonyl derivatives) can be obtained.

EXAMPLE 55

Using essentially the same procedures as in Examples 50–53, but substituting a 4-substituted piperidine from Procedures 1–10 in Example 50, Step E and/or a substituted benzoyl or sulfonyl chloride in Example 50, Step B, a variety of 1-(RS and/or SS)-(N-(substituted-benzoyl)-N-(methyl)amino)-3-(SR)-((4-(substituted)piperidin-1-yl)methyl)-4-(SR)-phenylcyclopentane and 1-(RS and/or SS)-(N-(substituted-phenylsulfonyl)-N-(methyl)amino)-3-(SR)-((4-(substituted)piperidin-1-yl)methyl)-4-(SR)-phenylcyclopentane final compounds can be prepared.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

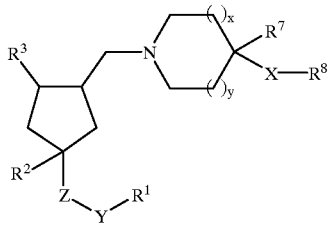

wherein:

X is selected from:
—(CO)NR$^9$—, —NR$^9$(CO)—, —O(CO)NR$^9$—, —NR$^9$(CO)O—, and —NR$^9$(CO)NR$^{10}$—,
where R$^9$ is independently selected from: hydrogen, $C_{1-10}$ alkyl, $C_{3-8}$ cycloalkyl, $C_{1-6}$ alkyl-$C_{3-6}$ cycloalkyl, $C_{2-10}$ alkenyl, $C_{2-10}$ alkynyl, benzyl, phenyl, or naphthyl, which is unsubstituted or substituted with 1–3 substituents where the substituents are independently selected from: halo, hydroxy, $C_{1-6}$ alkyl, $C_{1-3}$ alkoxy, phenyl and trifluoromethyl,
and where R$^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl,
or where R$^9$ and R$^{10}$ may be joined together to form a 5–8 membered ring which may be unsubstituted or substituted with halo, $C_{1-3}$ alkyl, and $C_{1-3}$ alkoxy;

Y is selected from:
a single bond, —(CO)—, —(CO)O—, —SO$_2$—, —SO$_2$NR$^9$—, —$C_{1-10}$ alkyl-, —(CO)NR$^9$—, and —(CS)NR$^9$—;

Z is selected from:
a single bond, —NR$^9$—, —O—, and —$C_{1-10}$ alkyl-;

R$^1$ is selected from:
phenyl, naphthyl, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, or $C_{1-4}$ alkyl-phenyl, which is unsubstituted or substituted with 1–3 substituents where the substituents are independently selected from: halo, $C_{1-3}$ alkyl, $C_{1-3}$ alkoxy, trifluoromethoxy and trifluoromethyl,
or when Z is —NR$^9$—, then R$^9$ and R$^1$ may be joined together to form a 5–8 membered alkyl or heterocycle ring which may be unsubstituted or substituted with halo, $C_{1-3}$ alkyl, and $C_{1-3}$ alkoxy;

R$^2$ is selected from:
(1) hydrogen, and
(2) hydroxy,
or R$^2$ and Z may be joined together to form a double bond;

R$^3$ is selected from the group consisting of:
phenyl and thienyl, which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —CO$_2$R$^9$,
(g) —NR$^9$R$^{10}$; and
(h) —CONR$^9$R$^{10}$;

R$^7$ is selected from:
(1) hydrogen,
(2) $C_{1-6}$ alkyl, which is unsubstituted or substituted with 1–4 substituents where the substituents are independently selected from: hydroxy, cyano, and halo,
(3) hydroxy, and
(4) halo;

R$^8$ is selected from:
$C_{1-10}$ alkyl, $C_{3-6}$ cycloalkyl, $C_{2-10}$ alkenyl, $C_{2-10}$ alkynyl, phenyl, $C_{1-6}$ alkyl-phenyl, $C_{1-6}$ alkyl-$C_{3-6}$ cycloalkyl, $C_{1-4}$ alkyl-O-phenyl, $C_{1-4}$ alkyl-O-$C_{1-4}$ alkyl-phenyl, which is unsubstituted or substituted with 1–7 of R$^{12}$ where
R$^{12}$ is independently selected from:
(a) halo,
(b) cyano,
(c) hydroxy,
(d) $C_{1-6}$ alkyl, which is unsubstituted or substituted with 1–5 of R$^{13}$ where R$^{13}$ is independently selected from: halo, cyano, hydroxy, $C_{1-6}$ alkoxy, —CO$_2$H, —CO$_2$($C_{1-6}$ alkyl), phenyl, trifluoromethyl, and —NR$^9$R$^{10}$,
(e) —O—$C_{1-6}$ alkyl, which is unsubstituted or substituted with 1–5 of R$^{13}$,
(f) —CF$_3$,
(g) —CHF$_2$,
(h) —CH$_2$F,
(i) —NO$_2$,
(j) phenyl,
(k) —CO$_2$R$^9$,
(l) tetrazolyl,
(m) —NR$^9$R$^{10}$,
(n) —NR$^9$—COR$^{10}$,
(o) —NR$^9$—CO$_2$R$^{10}$,
(p) —CO—NR$^9$R$^{10}$,
(q) —OCO—NR$^9$R$^{10}$,
(r) —NR$^9$CO—NR$^9$R$^{10}$,
(s) —S(O)$_m$—R$^9$, wherein m is an integer selected from 0, 1 and 2,
(t) —S(O)$_2$—NR$^9$R$^{10}$,
(u) —NR$^9$S(O)$_2$—R$^{10}$,
(v) —NR$^9$S(O)$_2$—NR$^9$R$^{10}$,
(w) 1-naphthyl, and
(x) 2-naphthyl;

x is an integer selected from 0, 1 and 2, and y is an integer selected from 0, 1 and 2, with the proviso that the sum of x and y is 2;

or a pharmaceutically acceptable salt thereof or an individual diastereomer thereof.

2. A compound of claim 1, wherein
X is selected from:
—(CO)NR$^9$—, —NR$^9$(CO)—, —O(CO)NR$^9$—, —NR$^9$(CO)O—, and —NR$^9$(CO)NR$^{10}$—,
where R$^9$ is independently selected from: hydrogen, $C_{1-10}$ alkyl, $C_{3-8}$ cycloalkyl, $C_{1-6}$ alkyl-$C_{3-6}$ cycloalkyl, $C_{2-10}$ alkenyl, $C_{2-10}$ alkynyl, benzyl or phenyl, which is unsubstituted or substituted with 1–3 substituents where the substituents are independently selected from: halo, $C_{1-6}$ alkyl, $C_{1-3}$ alkoxy, phenyl and trifluoromethyl,
and where R$^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl, Y is selected from:
a single bond, —(CO)—, —(CO)O—, —SO$_2$—, —C$_{1-10}$ alkyl-, —(CO)NR$^9$—, and —(CS)NR$^9$—;

Z is selected from:
a single bond, —NR$^9$—, —O—, and —C$_{1-10}$ alkyl-; and

R$^1$ is selected from:
phenyl, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, or $C_{1-4}$ alkyl-phenyl, which is unsubstituted or substituted with 1–3 substituents where the substituents are independently selected from: halo, $C_{1-3}$ alkyl, $C_{1-3}$ alkoxy, trifluoromethoxy and trifluoromethyl, or a pharmaceutically acceptable salts thereof or an individual diastereomers thereof.

3. A compound of claim 2, wherein Y is selected from a single bond, —(CO)—, —(CS)NR$^9$—, —(CO)O—, —SO$_2$—, and —(CO)NR$^9$—;

R$^9$ is independently selected from hydrogen and $C_{1-6}$ alkyl; and

Z is selected from a single bond, —O—, and —NR$^9$—;
or a pharmaceutically acceptable salt thereof or an individual diastereomer thereof.

4. A compound of claim 1, wherein x is 1 and y is 1;
or a pharmaceutically acceptable salt thereof or an individual diastereomer thereof.

5. A compound of claim 1, wherein X is selected from:
—NR$^9$(CO)O— and —NR$^9$(CO)NR$^{10}$—,
where R$^9$ is independently selected from hydrogen, $C_{1-10}$ alkyl, $C_{2-10}$ alkenyl, and $C_{1-6}$ alkyl-$C_{3-6}$ cycloalkyl,
where R$^{10}$ is independently selected from hydrogen and $C_{1-6}$ alkyl, or where R$^9$ and R$^{10}$ may be joined together to form a 5–8 membered ring which is unsubstituted;
or a pharmaceutically acceptable salt thereof or an individual diastereomer thereof.

6. A compound of claim 5, wherein that X is selected from:
—NR$^9$(CO)O—, and —NR$^9$(CO)NH—,
where R$^9$ is independently selected from methyl, ethyl, n-propyl, allyl, and —CH$_2$-cyclopropyl;
or a pharmaceutically acceptable salt thereof or an individual diastereomer thereof.

7. A compound of claim 1, wherein Y is selected from a single bond, —(CO)—, —(CS)NR$^9$—, —(CO)O—, —SO$_2$—, and —(CO)NR$^9$—, where R$^9$ is independently selected from hydrogen and $C_{1-6}$ alkyl;
or a pharmaceutically acceptable salt thereof or an individual diastereomer thereof.

8. A compound of claim 1, wherein Z is selected from a single bond, —O—, and —NR$^9$—, where R$^9$ is independently selected from hydrogen, $C_{1-6}$ alkyl, $C_{3-8}$ cycloalkyl, phenyl, and $C_{1-6}$ alkyl-phenyl, which is unsubstituted or substituted with 1–3 substituents where the substituents are independently selected from: halo, $C_{1-3}$ alkyl, $C_{1-3}$ alkoxy, phenyl and trifluoromethyl;
or a pharmaceutically acceptable salt thereof or an individual diastereomer thereof.

9. A compound of claim 1, wherein R$^1$ is selected from $C_{1-10}$ alkyl, cyclohexyl, phenyl, $C_{1-2}$ alkyl-phenyl, and CH$_2$-cyclohexyl, which is unsubstituted or substituted with 1–3 substituents where the substituents are independently selected from: halo, $C_{1-3}$ alkyl, $C_{1-3}$ alkoxy, trifluoromethoxy and trifluoromethyl;

or a pharmaceutically acceptable salt thereof or an individual diastereomer thereof.

10. A compound of claim 9, wherein R$^1$ is selected from methyl, iso-butyl, tert-butyl, hexyl, cyclohexyl, CH$_2$-cyclohexyl, phenyl, and $C_{1-2}$ alkyl-phenyl, wherein the phenyl is unsubstituted or substituted with 1–3 substituents where the substituents are independently selected from: chloro, fluoro, methyl, tert-butyl, trifluoromethoxy and trifluoromethyl;

or a pharmaceutically acceptable salt thereof or an individual diastereomer thereof.

11. A compound of claim 1, wherein R$^2$ is hydrogen;
or a pharmaceutically acceptable salt thereof or an individual diastereomer thereof.

12. A compound of claim 1, wherein R$^3$ is selected from the group consisting of phenyl and thienyl, which may be unsubstituted or substituted with 1–5 substituents where the substituents are independently selected from:

(a) fluoro, (b) chloro, (c) trifluoromethyl, (d) hydroxy, and (e) $C_{1-3}$ alkyl;

or a pharmaceutically acceptable salt thereof or an individual diastereomer thereof.

13. A compound of claim 12, wherein R$^3$ is selected from the group consisting of phenyl, which may be unsubstituted or substituted with 1–5 substituents where the substituents are independently selected from:

(a) fluoro, and (b) chloro; and unsubstituted thienyl;

or a pharmaceutically acceptable salt thereof or an individual diastereomer thereof.

14. A compound of claim 13, wherein R$^3$ is unsubstituted phenyl, (3-fluoro)phenyl or 3-thienyl or a pharmaceutically acceptable salt thereof or an individual diastereomer thereof.

15. A compound of claim 1, wherein R$^7$ is hydrogen;

or a pharmaceutically acceptable salts thereof or an individual diastereomers thereof.

16. A compound of claim 1, wherein R$^8$ is selected from $C_{1-6}$ alkyl, $C_{3-6}$ cycloalkyl, —CH$_2$-cyclohexyl, phenyl, and —CH$_2$-phenyl, wherein the phenyl is unsubstituted or substituted with 1–5 substituents where the substituents are independently selected from:

(a) halo, (b) —NO$_2$, (c) —CF$_3$, (d) —C$_{1-6}$ alkyl, and (e) phenyl;

or a pharmaceutically acceptable salt thereof or an individual diastereomer thereof.

17. A compound of claim 1, which is selected from the group consisting of:

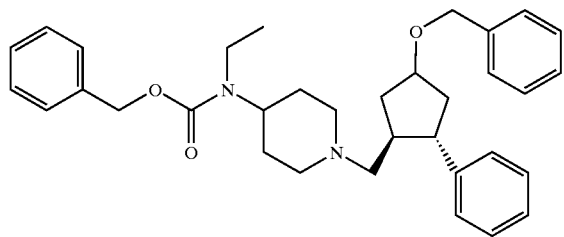
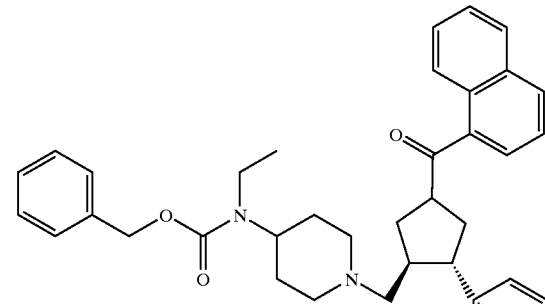
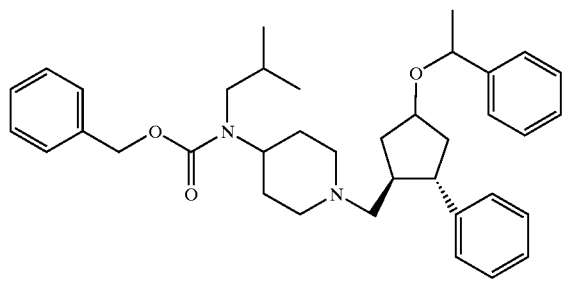
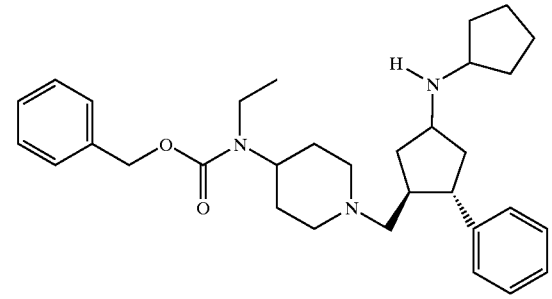
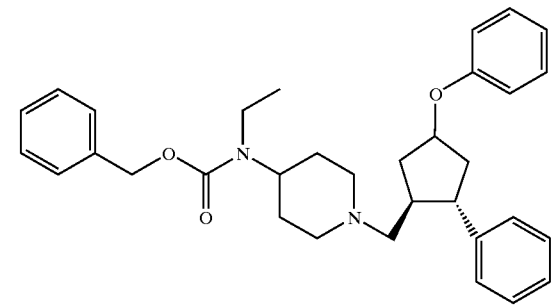
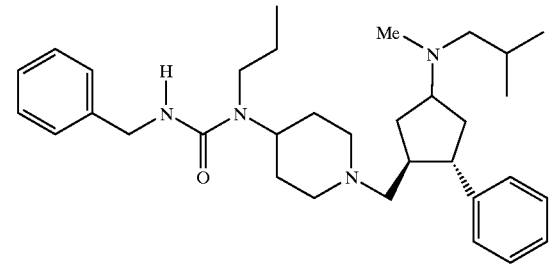
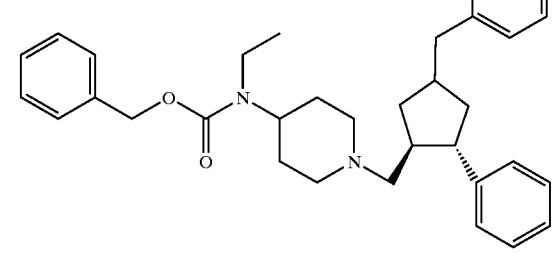
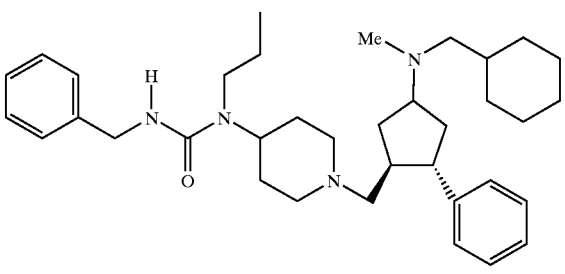
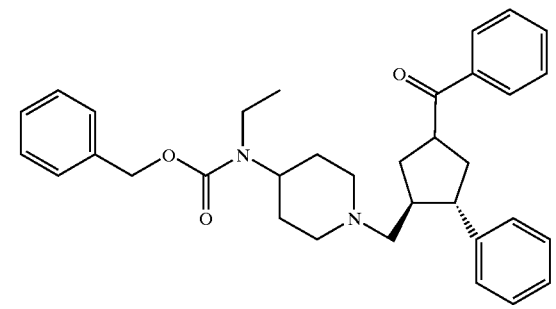
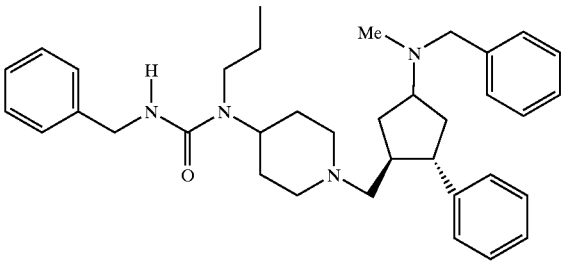
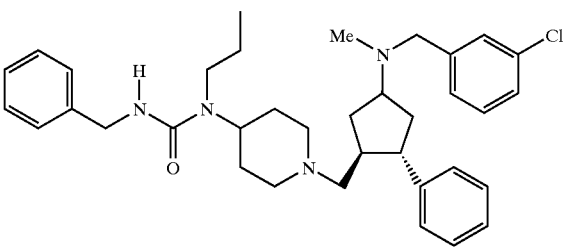

131
-continued
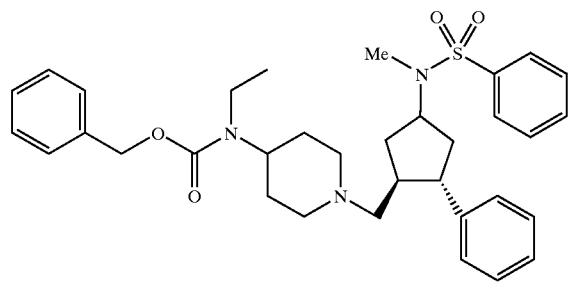
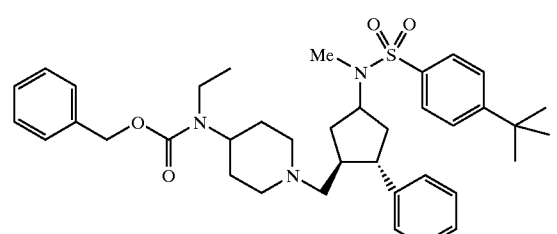
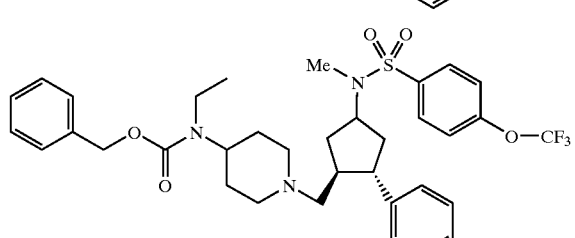
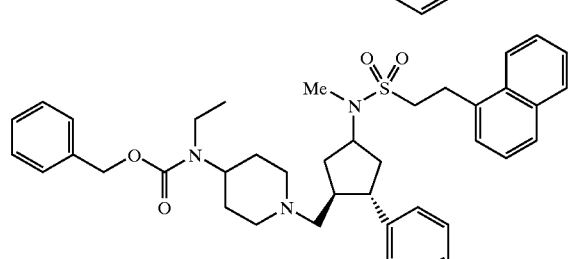
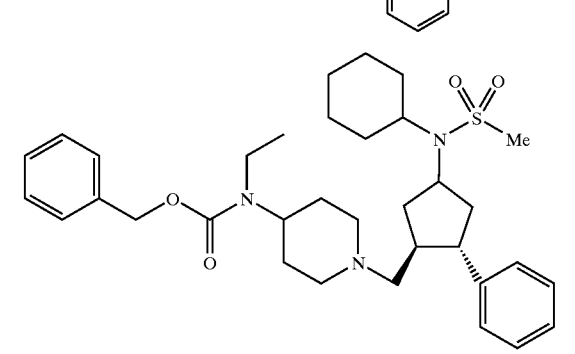
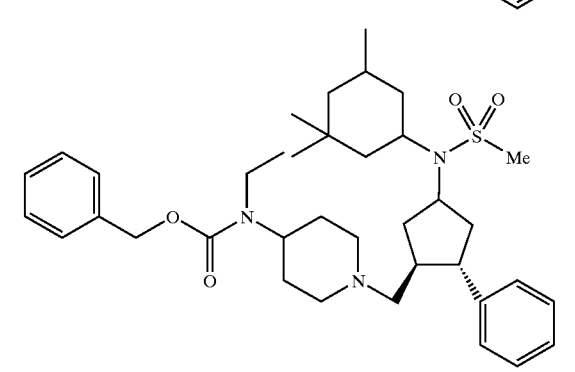
132
-continued
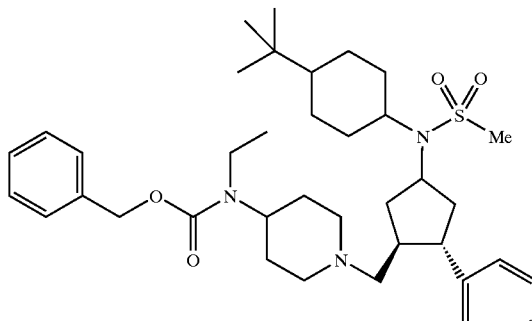
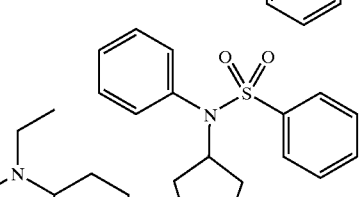
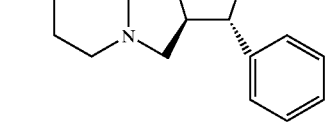
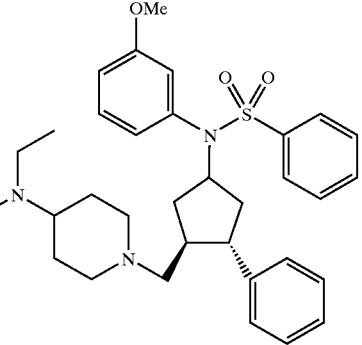
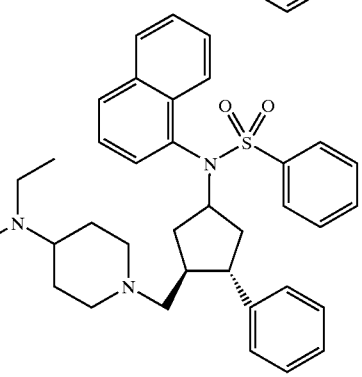
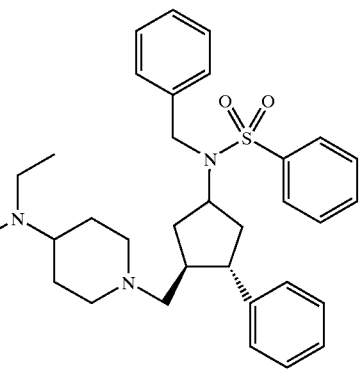

133
-continued
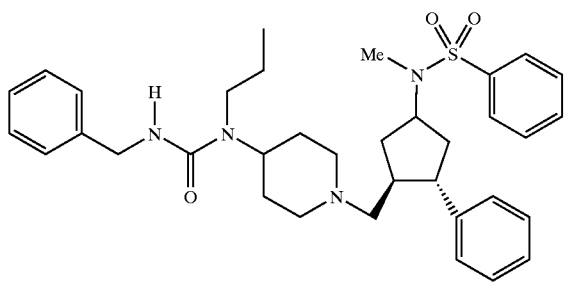
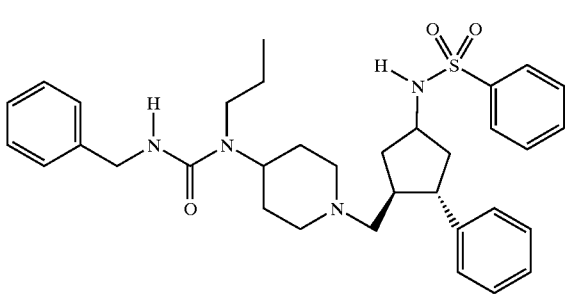
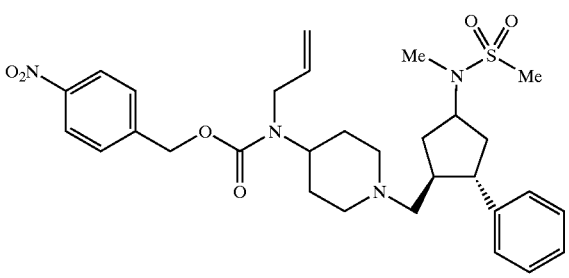
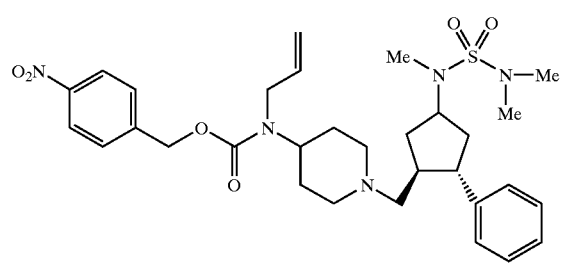
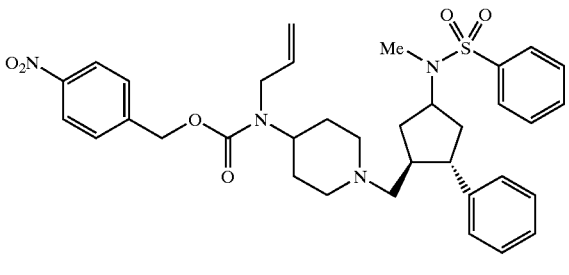
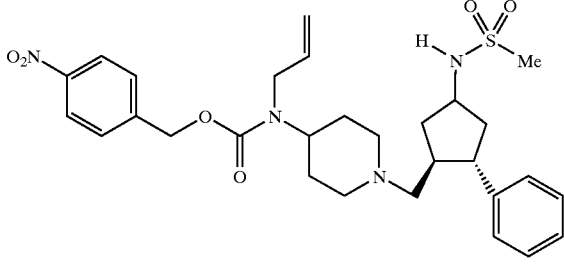
134
-continued
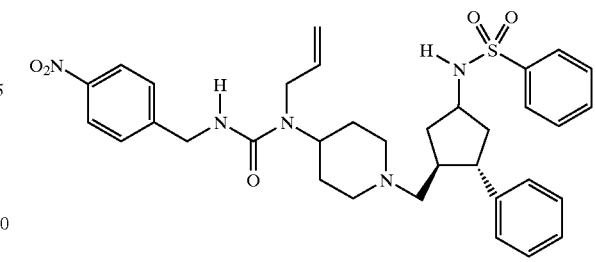
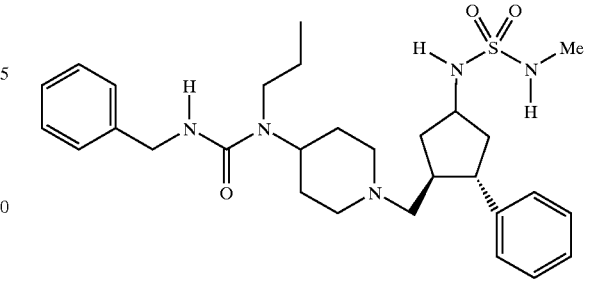
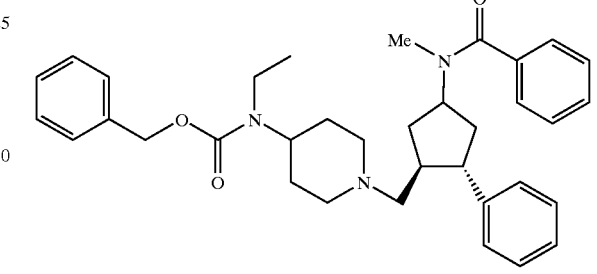
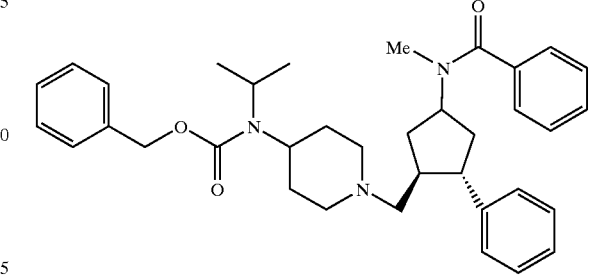
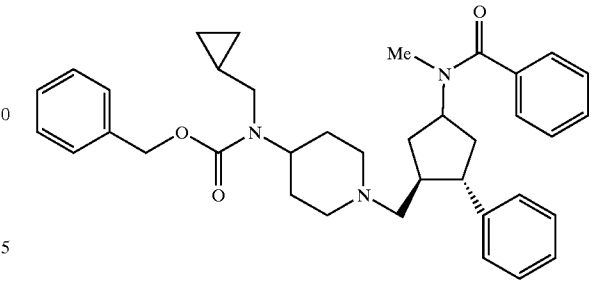
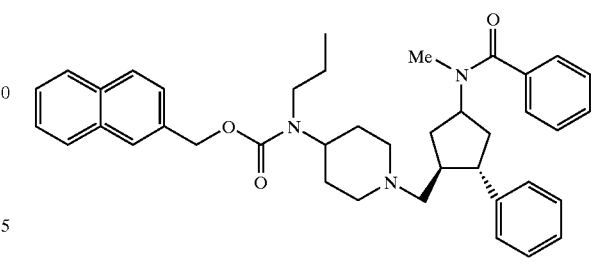

135
-continued
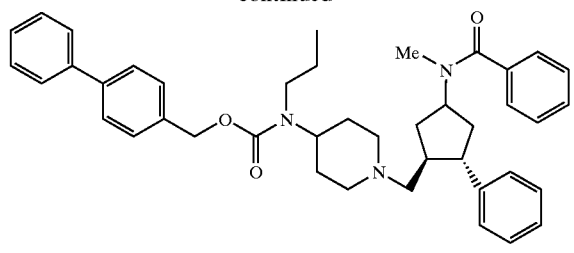
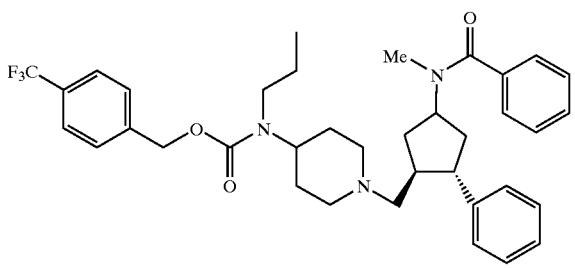
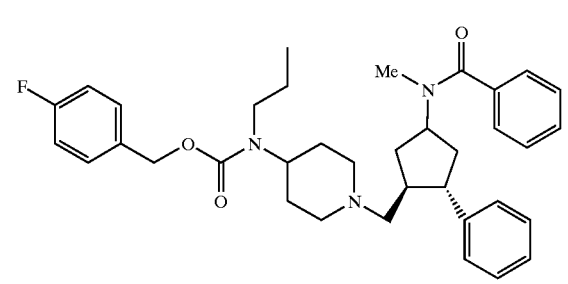
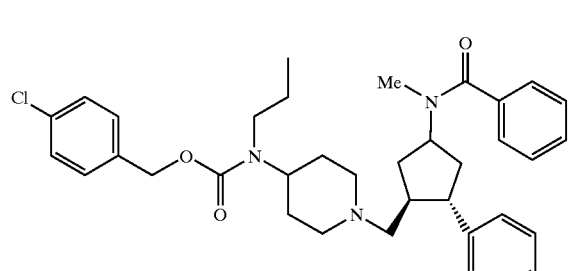
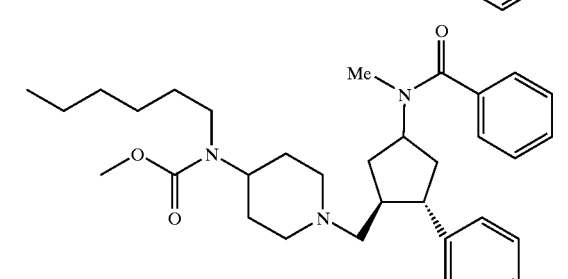
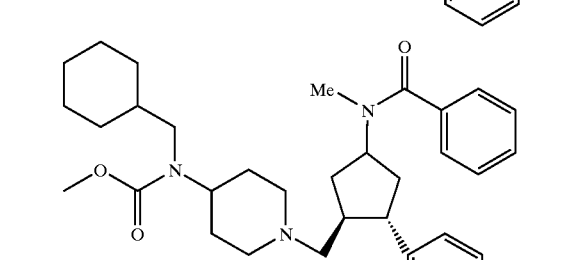
136
-continued
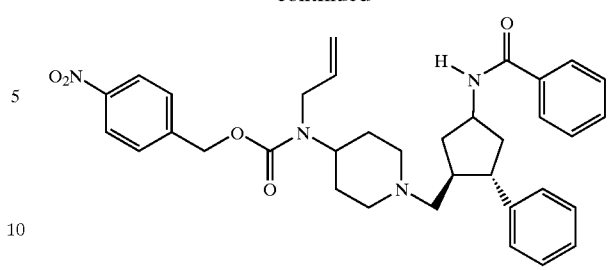
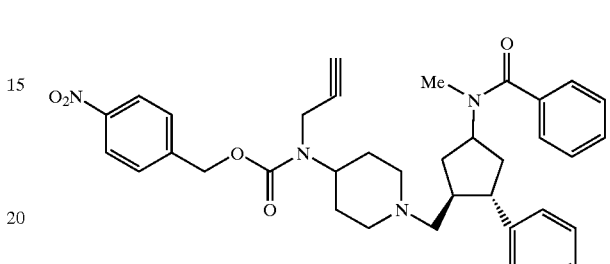
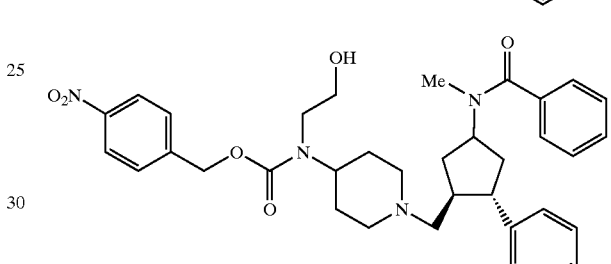
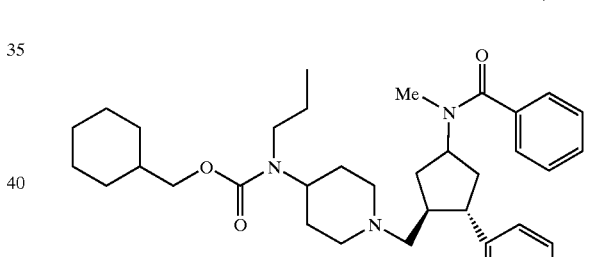
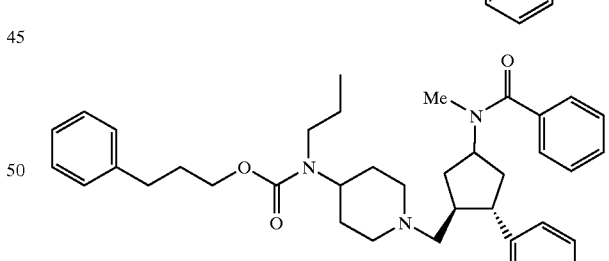
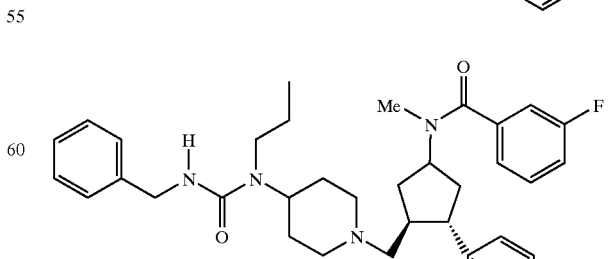

137
-continued
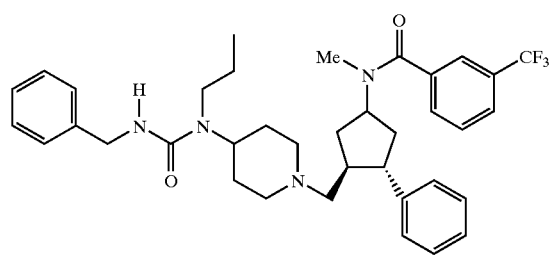
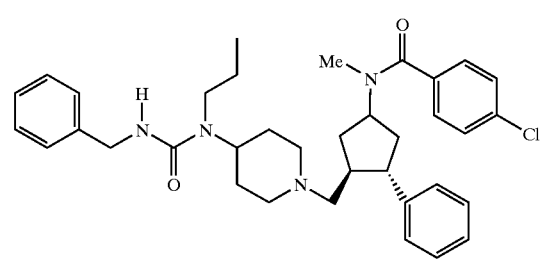
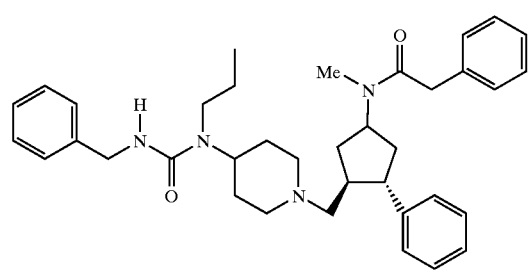
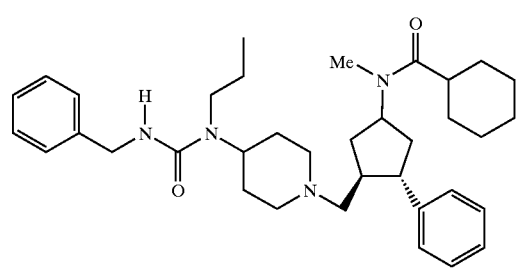
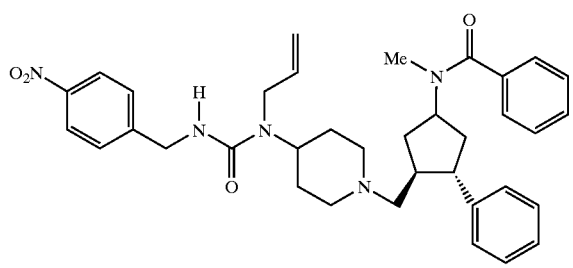
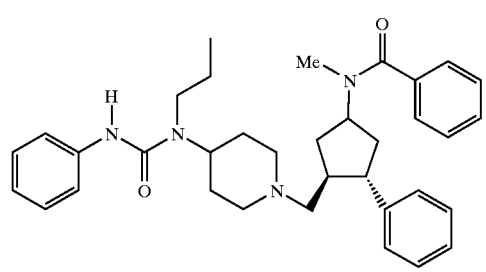
138
-continued
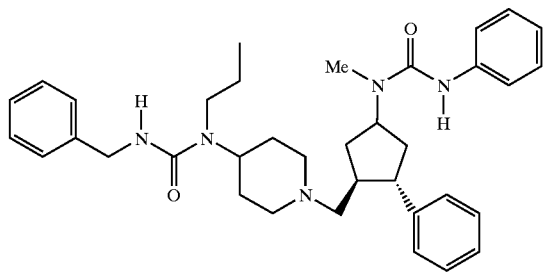
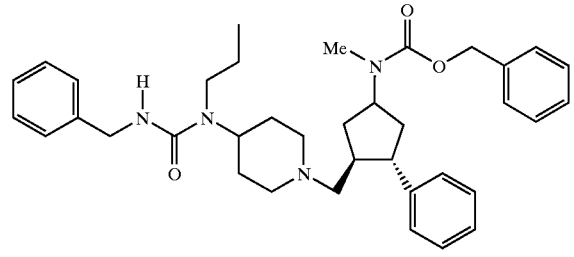
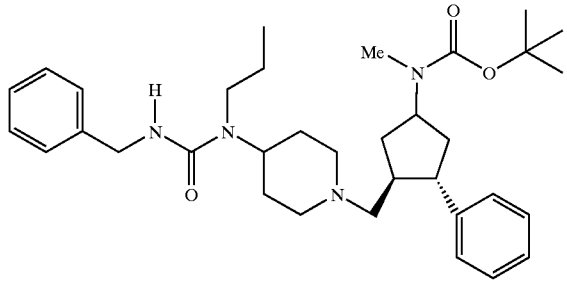
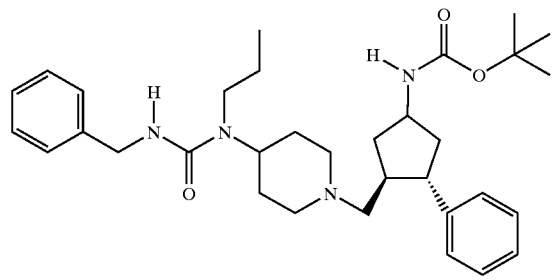
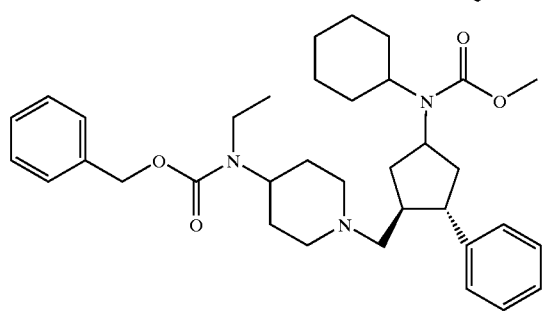
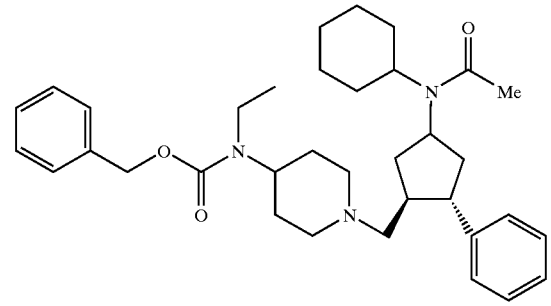

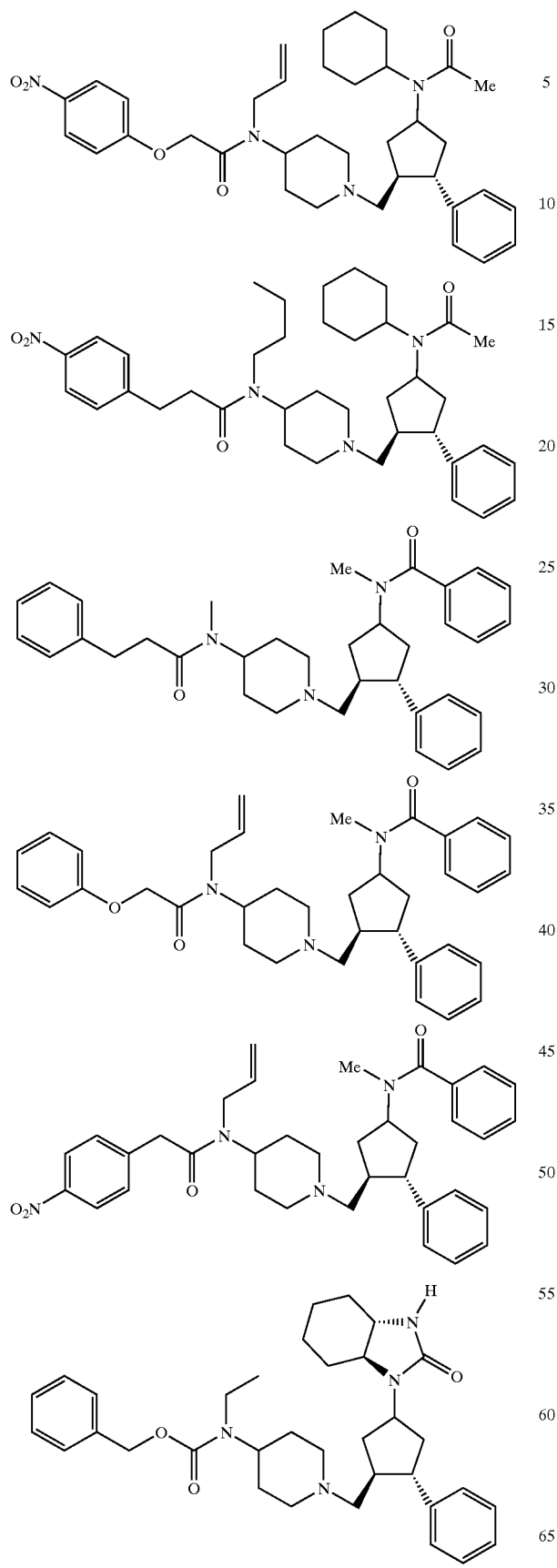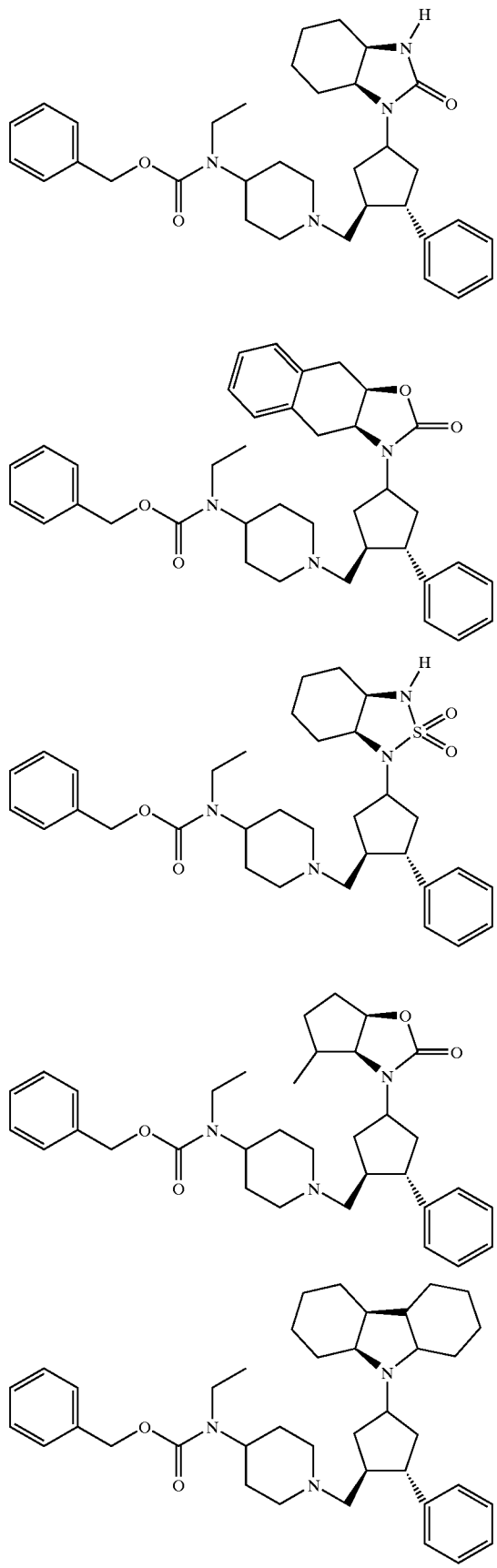

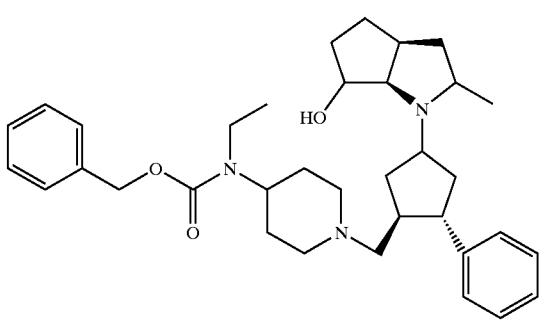

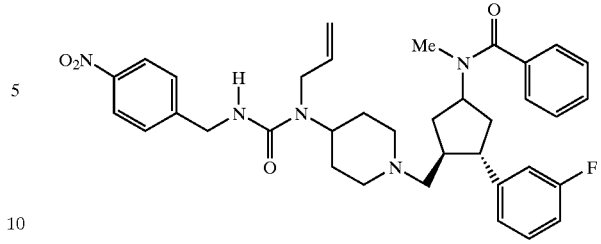

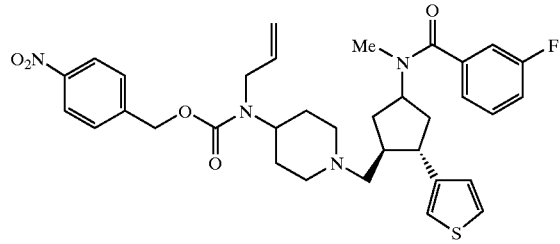

and pharmaceutically acceptable salts thereof and individual diastereomers thereof.

18. A pharmaceutical composition which comprises an inert carrier and a compound of claim 1 or a pharamaceutically acceptable salt thereof or an individual diastereomer thereof.

19. A method for modulation of CCR-3 or CCR-5 chemokine receptor activity in a mammal in need thereof to treat asthma, allergic rhinitis, dermatitus, conjunctivitis, atherosclerosis or rheumatoid arthritis, which comprises the administration of an effective amount of the compound of claim 1 or a pharmaceutically acceptable salt thereof or an individual diastereomer thereof.

20. A method for treating infection by HIV, delaying of the onset of AIDS, or treating AIDS comprising the administration to a patient of an effective amount of the compound of claim 1 or a pharmaceutically acceptable salt thereof or an individual diastereomer thereof.

* * * * *